United States Patent
Yin et al.

(10) Patent No.: US 12,098,204 B2
(45) Date of Patent: Sep. 24, 2024

(54) HUMANIZED ANTI-HUMAN PD-L1 MONOCLONAL ANTIBODY AND PREPARATION METHOD THEREFOR AND USE THEREOF

(71) Applicant: NANJING GENSCRIPT BIOTECH CO., LTD., Jiangsu (CN)

(72) Inventors: Liusong Yin, Jiangsu (CN); Tielin Zhou, Jiangsu (CN); Zhuo Fang, Jiangsu (CN); Yanling Mi, Jiangsu (CN); Chunchen Wu, Jiangsu (CN)

(73) Assignee: Nanjing Genscript Biotech Co., Ltd., Jiangsu (CN)

( * ) Notice: Subject to any disclaimer, the term of this patent is extended or adjusted under 35 U.S.C. 154(b) by 762 days.

(21) Appl. No.: 17/309,252

(22) PCT Filed: Nov. 15, 2019

(86) PCT No.: PCT/CN2019/118799
§ 371 (c)(1),
(2) Date: May 12, 2021

(87) PCT Pub. No.: WO2020/098785
PCT Pub. Date: May 22, 2020

(65) Prior Publication Data
US 2022/0073618 A1    Mar. 10, 2022

(30) Foreign Application Priority Data

Nov. 16, 2018    (CN) .......................... 201811366935.6

(51) Int. Cl.
*C07K 16/28*    (2006.01)
*A61K 39/00*    (2006.01)
*A61P 35/00*    (2006.01)

(52) U.S. Cl.
CPC .......... *C07K 16/2827* (2013.01); *A61P 35/00* (2018.01); *A61K 2039/507* (2013.01); *C07K 2317/24* (2013.01); *C07K 2317/33* (2013.01); *C07K 2317/76* (2013.01); *C07K 2317/92* (2013.01)

(58) Field of Classification Search
CPC ................................................. C07K 16/2827
See application file for complete search history.

(56) References Cited

U.S. PATENT DOCUMENTS 11,155,626 B2 * 10/2021 Zhu ..................... A61K 39/395
11,560,431 B2 * 1/2023 Kovacevich ........... A61K 45/06
2022/0135687 A1 * 5/2022 Yang .................. C07K 16/2827
                                                          424/133.1

FOREIGN PATENT DOCUMENTS

| CN | 102892785 A | 1/2013 |
| CN | 108239149 A | 7/2018 |
| CN | 108752476 A | 11/2018 |
| WO | 2017220989 A1 | 12/2017 |
| WO | 2018127711 A1 | 7/2018 |
| WO | 2019129211 A1 | 7/2019 |

OTHER PUBLICATIONS

Almagro & Fransson, Frontiers in Bioscience 13:1619-33 (Year: 2008).*
Brown et al., J. Immunol., 156(9):3285-91 (Year: 1996).*
Rodig. N. et al., "Endothelial expression of PD-LI and PD-L2 down-regulates CD8+ T cell activation and cytolysis", European Journal of Immunology, vol. 33, pp. 3117-3126 (2003).
International Search Report issued Feb. 13, 2020 from International Application No. PCT/CN2019/118799 (English Translation).

* cited by examiner

*Primary Examiner* — Jessica H Roark
(74) *Attorney, Agent, or Firm* — Ice Miller LLP

(57) ABSTRACT

The present invention relates to a humanized anti-human PD-L1 monoclonal antibody, and a preparation method and use thereof. The humanized anti-human PD-L1 monoclonal antibody provided in the present invention has high affinity and specificity for PD-L1, stimulates T cells to secrete cytokines, and specifically relieves the negative immune regulation by PD-L1. The effect of this antibody is not achieved by directly blocking the interaction between PD-1 and PD-L1, presenting a new mechanism of immune checkpoint regulation. Therefore, the functional humanized anti-human PD-L1 monoclonal antibody provided in the present invention activates T cells by regulating the PD-L1 signaling pathway, thereby achieving the purpose of tumor immunotherapy.

15 Claims, 26 Drawing Sheets
Specification includes a Sequence Listing.

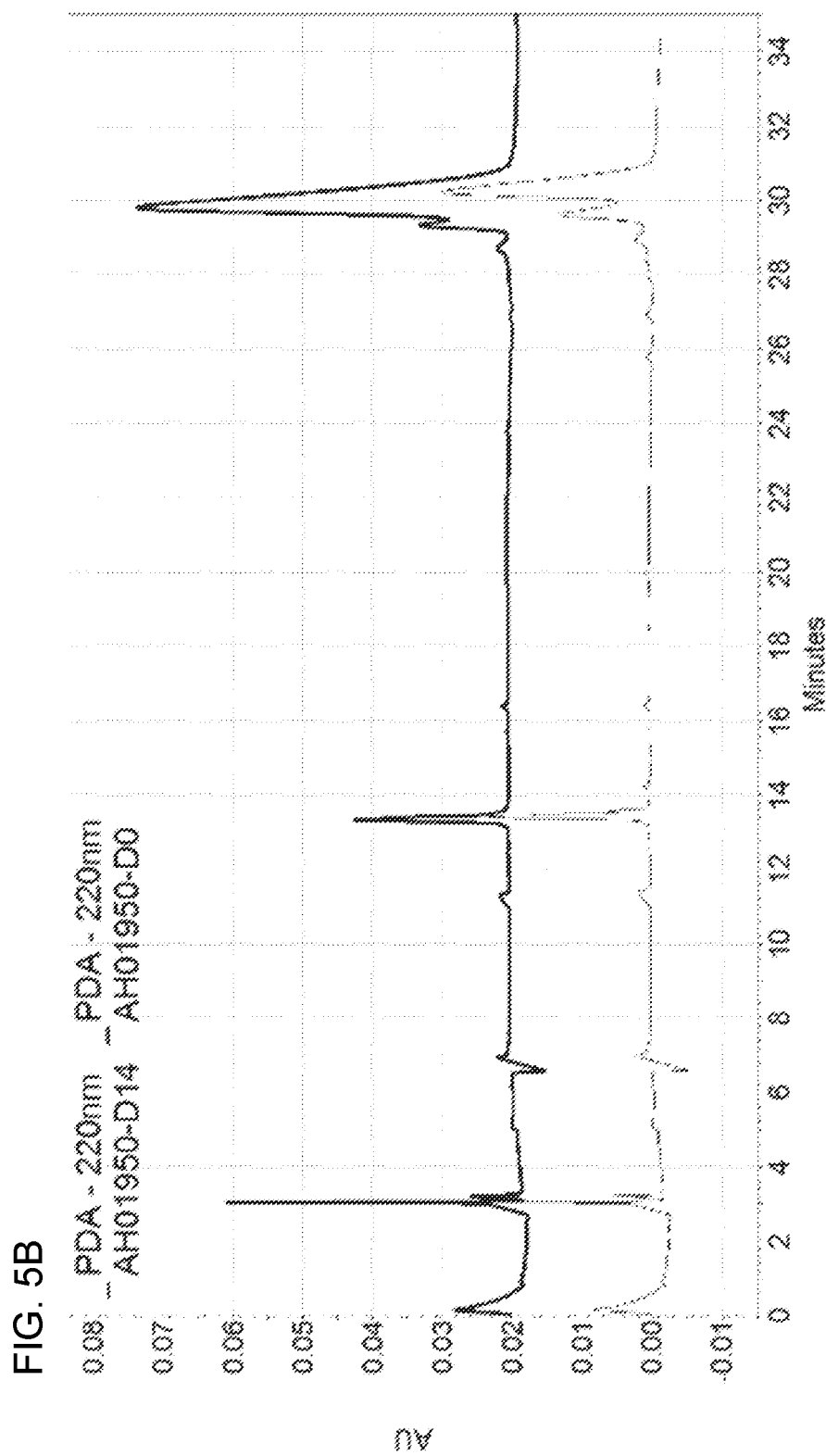

HUMANIZED ANTI-HUMAN PD-L1 MONOCLONAL ANTIBODY AND PREPARATION METHOD THEREFOR AND USE THEREOF

CROSS-REFERENCE TO RELATED APPLICATIONS

This application is a Section 371 of International Application No. PCT/CN2019/118799, filed on Nov. 15, 2019, which published in the Chinese language on May 22, 2020 under International Publication No. WO 2020/098785 A1, which claims priority to Chinese Application No. 201811366935.6, filed on Nov. 16, 2018, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "065824.10US1 Sequence Listing" and a creation date of May 20, 2024 and having a size of 28.7 kb. The sequence listing submitted via EFS-Web is part of the specification and is herein incorporated by reference in its entirety.

BACKGROUND

Technical Field

The present invention relates to the field of tumor immunotherapy and molecular immunology, and particularly to a humanized anti-human PD-L1 monoclonal antibody. The present invention also relates to a preparation method and use of the humanized anti-human PD-L1 monoclonal antibody.

Related Art

Adaptive immune system in humans defends against external infections and internal diseases through two major mechanisms including humoral immunity (mediated by B cells) and cellular immunity (mediated by T cells). As an important member in the immune system, T cells play an important role in tumor immunotherapy. For treatments with traditional cytokine-based drugs to the recently rising immune checkpoint inhibitors, the purpose of eliminating tumors is achieved by directly or indirectly activating T cells (Esther et al, physiol, 25(2):85-101, 2010; and Drew, Nature Reviews Cancer 12:252-264, 2012).

T cell activation requires two signals. The first signal, also known as a primary stimulatory signal, is achieved by the TCR recognizing a specific antigen presented by the MHC, and this signal is antigen specific. In addition, the activation of T cells is also regulated by a secondary stimulatory signal, also known as a costimulatory signal or a co-inhibitory signal to regulate the T cell activity (Jennifer et al, Annu Rev Immunol, 27:591-619, 2009). Such immunostimulatory or inhibitory molecules are called immune checkpoints. Immune checkpoint therapy is to control the T cell activity by regulating the costimulatory or co-inhibitory signal, allowing highly active T cells to kill tumor cells to achieve the purpose of cancer treatment (Suzanne et. al, Cancer Cell 27(4): 450-461, 2015). The anti-tumor mechanism of these drugs is different from any previous drugs. They do not simply target tumor or simply regulate immune cells, but specifically target key immune escape mechanism in the tumor microenvironment, and control and eliminate tumors by improving the tumor immune microenvironment. Therefore, the successful development of this therapy allows the tumor immunology to have an unprecedented progress, and bring great innovations and far-reaching impacts to the future tumor immunology and clinical research.

Programmed death receptor 1 (PD-1) is an important immunosuppressive molecule that is a member belonging to the CD28/PD-L1 family of T cell regulators. Antibody drugs against PD-1 are available at present, including Merck's Keytruda marketed in 2014 and Bristol-Myers Squibb's Opdivo marketed in 2015. The drugs directed against PD-1/PD-L1 target have milestone events continuously. In 2017, Opdivo was ranked in TOP 10 for the first time, and Keytruda was ranked in TOP 20 for the first time. The sales of the two antibody drugs in 2017 were 5.686 billion $ and 3.809 billion $ respectively.

Programmed death receptor-ligand 1 (PD-L1) is one of the ligands of PD-1 (the other ligand is PD-L2). PD-L1 is the type I transmembrane protein with a size of about 40 kDa, and is also an important immune checkpoint molecule like PD-1. The PD-L1 ligand is quite tumor specific, induces expression in the tumor microenvironment, and participates in the immune regulation in the tumor microenvironment. The binding of PD-L1 and PD-1 transmits a co-inhibitory signal to reduce the activity and proliferation of T cells, thereby prompting tumor cells to escape the monitoring and killing by T cells (Dong et al, Nat Med; 8:793-800, 2002). Blocking the PD-L1 ligand or PD-1 receptor can repair the ongoing tumor immune response. This therapy directs against the key molecular mechanism in tumor immune escape, so it can target a variety of tumors with a good therapeutic effect and few side effect.

PD-L1 monoclonal antibody drugs can specifically block the binding of PD-1 and PD-L1 to weaken or block the transduction of a negative regulatory signal for T cells by PD-L1, and enhance the immune response of T cells to various antigens. At present, the PD-L1 monoclonal antibody drug has been used in clinical trials to treat a variety of human cancers, including non-small cell lung cancer, melanoma, colorectal cancer, renal cell carcinoma, ovarian cancer, prostate cancer, gastric cancer, and breast cancer (Julie et al. al., N Engl Med 366:2455-2465, 2012).

The first PD-L1 anti-cancer antibody drug, PD-L1 antibody drug atezolizumab (trade name Tecentriq) for the treatment of advanced bladder cancer available from Genentech under Roche, was approved for marketing by FDA on May 19, 2016. This indicates that the immune checkpoint is successful and feasible in the clinical phases of tumor immunotherapy. Moreover, with the preclinical trials to verify the ability of monoclonal antibodies against different immunomodulatory factors in the combined treatment of cancers (Mace et al, Journal for ImmunoTherapy of cancer 3:366, 2015; and Lussier et al, Journal for ImmunoTherapy of Cancer 3: 21, 2015), the PD-L1 monoclonal antibody is combined with monoclonal antibodies of different immunosuppressive molecules or small molecule compounds to form a combination therapy used in the clinical trial for different cancers.

There are currently three PD-L1 monoclonal antibody drugs available on the market, which are approved for different indications. Immune checkpoint inhibiting monoclonal antibodies also have different extents of side effects in the human body, including induction of immunogenicity in some patients, and excessive suppression of checkpoint signaling to cause autoimmune diseases (Claire et al, JAMA Oncol, 2(10): 1346-1353, 2016), and different PD-L1 monoclonal antibodies will have varying degrees of developability. Therefore, there is still a need to develop new functional antibodies that can block the binding of PD-L1 to PD-1 protein.

SUMMARY

In one aspect, the present invention provides a humanized anti-human PD-L1 monoclonal antibody or a functional fragment thereof, which can specifically bind to PD-L1, and is characterized in that it relieves the immunosuppression by indirectly blocking the interaction between PD1 and PD-L1.

In some embodiments, the humanized anti-human PD-L1 monoclonal antibody or a functional fragment thereof comprises a heavy chain variable region having an amino acid sequence selected from amino acid sequences having at least 80% sequence identity to SEQ ID NO:9, SEQ ID NO:10, SEQ ID NO:11, SEQ ID NO:12, SEQ ID NO:13, SEQ ID NO:14, SEQ ID NO: 15 or SEQ ID NO:16.

In another aspect, the present invention provides a humanized anti-human PD-L1 monoclonal antibody or a functional fragment thereof, which comprises a heavy chain variable region having an amino acid sequence selected from amino acid sequences having at least 80% sequence identity to SEQ ID NO:9, SEQ ID NO: 10, SEQ ID NO: 11, SEQ ID NO: 12, SEQ ID NO: 13, SEQ ID NO: 14, SEQ ID NO:15 or SEQ ID NO: 16.

In some embodiments, the heavy chain variable region has an amino acid sequence selected from amino acid sequences having at least 81%, 82%, 83%, 84%, 85%, 86%, 87%, 88%, 89%, 90%, 91%, 92%, 93%, 94%, 95%, 96%, 97%, 98% or 99% sequence identity to SEQ ID NO:9, SEQ ID NO:10, SEQ ID NO:11, SEQ ID NO:12, SEQ ID NO:13, SEQ ID NO:14, SEQ ID NO:15 or SEQ ID NO:16.

The present invention provides a humanized anti-human PD-L1 monoclonal antibody or a functional fragment thereof, which comprises a heavy chain variable region, having an amino acid sequence selected from amino acid sequences having at least 80% sequence identity to SEQ ID NO:9, SEQ ID NO: 10, SEQ ID NO: 11, SEQ ID NO: 12, SEQ ID NO: 13, SEQ ID NO: 14, SEQ ID NO:15 or SEQ ID NO:16; and a light chain variable region, having an amino acid sequence selected from amino acid sequences having at least 80% sequence identity to SEQ ID NO:17, SEQ ID NO:18, SEQ ID NO:19, SEQ ID NO:20, SEQ ID NO:21, SEQ ID NO:22, SEQ ID NO:23 or SEQ ID NO:24.

In some embodiments, the heavy chain variable region has an amino acid sequence selected from amino acid sequences having at least 81%, 82%, 83%, 84%, 85%, 86%, 87%, 88%, 89%, 90%, 91%, 92%, 93%, 94%, 95%, 96%, 97%, 98% or 99% sequence identity to SEQ ID NO:9, SEQ ID NO:10, SEQ ID NO:11, SEQ ID NO: 12, SEQ ID NO:13, SEQ ID NO: 14, SEQ ID NO:15 or SEQ ID NO:16.

In some embodiments, the light chain variable region has an amino acid sequence selected from amino acid sequences having at least 81%, 82%, 83%, 84%, 85%, 86%, 87%, 88%, 89%, 90%, 91%, 92%, 93%, 94%, 95%, 96%, 97%, 98% or 99% sequence identity to SEQ ID NO:17, SEQ ID NO: 18, SEQ ID NO:19, SEQ ID NO:20, SEQ ID NO:21, SEQ ID NO:22, SEQ ID NO:23 or SEQ ID NO:24.

In some embodiments, the heavy chain variable region has an amino acid sequence selected from amino acid sequences having a substitution(s), insertion(s) or deletion(s) of up to 20 amino acid residues in the sequence as shown in SEQ ID NO:9, SEQ ID NO: 10, SEQ ID NO:11, SEQ ID NO:12, SEQ ID NO:13, SEQ ID NO:14, SEQ ID NO:15 or SEQ ID NO:16. In some embodiments, the heavy chain variable region has an amino acid sequence selected from amino acid sequences having a substitution(s), insertion(s) or deletion(s) of 1, 2, 3, 4, 5, 6, 7, 8, 9 or 10 amino acid residues in the sequence as shown in SEQ ID NO:9, SEQ ID NO:10, SEQ ID NO:11, SEQ ID NO: 12, SEQ ID NO: 13, SEQ ID NO: 14, SEQ ID NO: 15 or SEQ ID NO: 16.

In some embodiments, the heavy chain variable region has an amino acid sequence selected from amino acid sequences having up to 20 conservative amino acid substitutions in the sequence as shown in SEQ ID NO:9, SEQ ID NO: 10, SEQ ID NO: 11, SEQ ID NO: 12, SEQ ID NO: 13, SEQ ID NO:14, SEQ ID NO:15 or SEQ ID NO:16. In some embodiments, the heavy chain variable region has an amino acid sequence selected from amino acid sequences having up to 20, 18, 16, 14, 12, 10, 8, 6, 4, 2 or 1 conservative amino acid substitution(s) in the sequence as shown in SEQ ID NO:9, SEQ ID NO: 10, SEQ ID NO:11, SEQ ID NO: 12, SEQ ID NO: 13, SEQ ID NO: 14, SEQ ID NO:15 or SEQ ID NO:16.

In some embodiments, the light chain variable region has an amino acid sequence selected from amino acid sequences having a substitution, insertion or deletion of up to 20 amino acid residues in the sequence as shown in SEQ ID NO:17, SEQ ID NO:18, SEQ ID NO:19, SEQ ID NO:20, SEQ ID NO:21, SEQ ID NO:22, SEQ ID NO:23 or SEQ ID NO:24. In some embodiments, the light chain variable region has an amino acid sequence selected from amino acid sequences having a substitution(s), insertion(s) or deletion(s) of 1, 2, 3, 4, 5, 6, 7, 8, 9 or 10 amino acid residues in the sequence as shown in SEQ ID NO:17, SEQ ID NO:18, SEQ ID NO:19, SEQ ID NO:20, SEQ ID NO:21, SEQ ID NO:22, SEQ ID NO:23 or SEQ ID NO:24.

In some embodiments, the light chain variable region has an amino acid sequence selected from amino acid sequences having up to 20 conservative amino acid substitutions in the sequence as shown in SEQ ID NO:17, SEQ ID NO:18, SEQ ID NO:19, SEQ ID NO:20, SEQ ID NO:21, SEQ ID NO:22, SEQ ID NO:23 or SEQ ID NO:24. In some embodiments, the light chain variable region has an amino acid sequence selected from amino acid sequences having up to 20, 18, 16, 14, 12, 10, 8, 6, 4, 2 or 1 conservative amino acid substitution(s) in the sequence as shown in SEQ ID NO: 17, SEQ ID NO: 18, SEQ ID NO: 19, SEQ ID NO:20, SEQ ID NO:21, SEQ ID NO:22, SEQ ID NO:23 or SEQ ID NO:24.

In an embodiment, the heavy chain variable region has an amino acid sequence selected from SEQ ID NO:9, SEQ ID NO: 10, SEQ ID NO:11, SEQ ID NO: 12, SEQ ID NO: 13, SEQ ID NO: 14, SEQ ID NO:15 or SEQ ID NO:16.

In an embodiment, the light chain variable region has an amino acid sequence selected from SEQ ID NO:17, SEQ ID NO: 18, SEQ ID NO: 19, SEQ ID NO:20, SEQ ID NO:21, SEQ ID NO:22, SEQ ID NO:23 or SEQ ID NO:24.

In an embodiment, the heavy chain variable region has an amino acid sequence selected from SEQ ID NO:9, SEQ ID NO: 10, SEQ ID NO: 11, SEQ ID NO: 12, SEQ ID NO: 13, SEQ ID NO: 14, SEQ ID NO:15 or SEQ ID NO:16; and the light chain variable region has an amino acid sequence selected from SEQ ID NO:17, SEQ ID NO: 18, SEQ ID NO: 19, SEQ ID NO:20, SEQ ID NO:21, SEQ ID NO:22, SEQ ID NO:23 or SEQ ID NO:24.

In some embodiments, the humanized anti-human PD-L1 monoclonal antibody or a functional fragment thereof has a heavy chain variable region and a light chain variable region selected from a combination of a heavy chain variable region having an amino acid sequence that is at least 80% identical to SEQ ID NO:9, and a light chain variable region having an amino acid sequence that is at least 80% identical to SEQ ID NO:17;
a heavy chain variable region having an amino acid sequence that is at least 80% identical to SEQ ID NO:10, and a light chain variable region having an amino acid sequence that is at least 80% identical to SEQ ID NO:18;
a heavy chain variable region having an amino acid sequence that is at least 80% identical to SEQ ID NO:11, and a light chain variable region having an amino acid sequence that is at least 80% identical to SEQ ID NO:19;
a heavy chain variable region having an amino acid sequence that is at least 80% identical to SEQ ID NO:12, and a light chain variable region having an amino acid sequence that is at least 80% identical to SEQ ID NO:20;
a heavy chain variable region having an amino acid sequence that is at least 80% identical to SEQ ID NO:13, and a light chain variable region having an amino acid sequence that is at least 80% identical to SEQ ID NO:21;
a heavy chain variable region having an amino acid sequence that is at least 80% identical to SEQ ID NO:14, and a light chain variable region having an amino acid sequence that is at least 80% identical to SEQ ID NO:22;
a heavy chain variable region having an amino acid sequence that is at least 80% identical to SEQ ID NO:15, and a light chain variable region having an amino acid sequence that is at least 80% identical to SEQ ID NO:23; or
a heavy chain variable region having an amino acid sequence that is at least 80% identical to SEQ ID NO:16, and a light chain variable region having an amino acid sequence that is at least 80% identical to SEQ ID NO:24.

In some preferred embodiment, the humanized anti-human PD-L1 monoclonal antibody or a functional fragment thereof has a heavy chain variable region and a light chain variable region selected from a combination of
  a heavy chain variable region having an amino acid sequence that is at least 85%, 90%, 92%, 94%, 95%, 96%, 97%, 98%, or 99% identical to SEQ ID NO:9, and a light chain variable region having an amino acid sequence that is at least 85%, 90%, 92%, 94%, 95%, 96%, 97%, 98%, or 99% identical to SEQ ID NO:17;
  a heavy chain variable region having an amino acid sequence that is at least 85%, 90%, 92%, 94%, 95%, 96%, 97%, 98%, or 99% identical to SEQ ID NO:10, and a light chain variable region having an amino acid sequence that is at least 85%, 90%, 92%, 94%, 95%, 96%, 97%, 98%, or 99% identical to SEQ ID NO:18;
  a heavy chain variable region having an amino acid sequence that is at least 85%, 90%, 92%, 94%, 95%, 96%, 97%, 98%, or 99% identical to SEQ ID NO:11, and a light chain variable region having an amino acid sequence that is at least 85%, 90%, 92%, 94%, 95%, 96%, 97%, 98%, or 99% identical to SEQ ID NO:19;
  a heavy chain variable region having an amino acid sequence that is at least 85%, 90%, 92%, 94%, 95%, 96%, 97%, 98%, or 99% identical to SEQ ID NO:12, and a light chain variable region having an amino acid sequence that is at least 85%, 90%, 92%, 94%, 95%, 96%, 97%, 98%, or 99% identical to SEQ ID NO:20;
  a heavy chain variable region having an amino acid sequence that is at least 85%, 90%, 92%, 94%, 95%, 96%, 97%, 98%, or 99% identical to SEQ ID NO:13, and a light chain variable region having an amino acid sequence that is at least 85%, 90%, 92%, 94%, 95%, 96%, 97%, 98%, or 99% identical to SEQ ID NO:21;
  a heavy chain variable region having an amino acid sequence that is at least 85%, 90%, 92%, 94%, 95%, 96%, 97%, 98%, or 99% identical to SEQ ID NO:14, and a light chain variable region having an amino acid sequence that is at least 85%, 90%, 92%, 94%, 95%, 96%, 97%, 98%, or 99% identical to SEQ ID NO:22;
  a heavy chain variable region having an amino acid sequence that is at least 85%, 90%, 92%, 94%, 95%, 96%, 97%, 98%, or 99% identical to SEQ ID NO:15, and a light chain variable region having an amino acid sequence that is at least 85%, 90%, 92%, 94%, 95%, 96%, 97%, 98%, or 99% identical to SEQ ID NO:23; or
  a heavy chain variable region having an amino acid sequence that is at least 85%, 90%, 92%, 94%, 95%, 96%, 97%, 98%, or 99% identical to SEQ ID NO:16, and a light chain variable region having an amino acid sequence that is at least 85%, 90%, 92%, 94%, 95%, 96%, 97%, 98%, or 99% identical to SEQ ID NO:24.

In an embodiment, the humanized anti-human PD-L1 monoclonal antibody or a functional fragment thereof has a heavy chain variable region and a light chain variable region selected from a combination of
  a heavy chain variable region as shown in SEQ ID NO:9 and a light chain variable region as shown in SEQ ID NO:17;
  a heavy chain variable region as shown in SEQ ID NO: 10 and a light chain variable region as shown in SEQ ID NO:18;
  a heavy chain variable region as shown in SEQ ID NO: 11 and a light chain variable region as shown in SEQ ID NO:19;
  a heavy chain variable region as shown in SEQ ID NO:12 and a light chain variable region as shown in SEQ ID NO:20;
  a heavy chain variable region as shown in SEQ ID NO: 13 and a light chain variable region as shown in SEQ ID NO:21;
  a heavy chain variable region as shown in SEQ ID NO:14 and a light chain variable region as shown in SEQ ID NO:22;
  a heavy chain variable region as shown in SEQ ID NO:15 and a light chain variable region as shown in SEQ ID NO:23;
  a heavy chain variable region as shown in SEQ ID NO:16 and a light chain variable region as shown in SEQ ID NO:24; or amino acid sequences having up to 20, 18, 16, 14, 12, 10, 8, 6, 4, 2 or 1 conservative amino acid substitution(s) in each group of the foregoing sequences.

In an embodiment, the humanized anti-human PD-L1 monoclonal antibody or a functional fragment thereof has a heavy chain variable region and a light chain variable region selected from a combination of
  a heavy chain variable region as shown in SEQ ID NO:9 and a light chain variable region as shown in SEQ ID NO:17;
  a heavy chain variable region as shown in SEQ ID NO:10 and a light chain variable region as shown in SEQ ID NO:18;

a heavy chain variable region as shown in SEQ ID NO:11
and a light chain variable region as shown in SEQ ID NO:19;
a heavy chain variable region as shown in SEQ ID NO:12
and a light chain variable region as shown in SEQ ID NO:20;
a heavy chain variable region as shown in SEQ ID NO:13
and a light chain variable region as shown in SEQ ID NO:21;
a heavy chain variable region as shown in SEQ ID NO: 14
and a light chain variable region as shown in SEQ ID NO:22;
a heavy chain variable region as shown in SEQ ID NO: 15
and a light chain variable region as shown in SEQ ID NO:23; or
a heavy chain variable region as shown in SEQ ID NO:16
and a light chain variable region as shown in SEQ ID NO:24.

In a preferred embodiment, the humanized anti-human PD-L1 monoclonal antibody or a functional fragment thereof has a heavy chain variable region and a light chain variable region selected from a combination of
a heavy chain variable region as shown in SEQ ID NO:9
and a light chain variable region as shown in SEQ ID NO:17;
a heavy chain variable region as shown in SEQ ID NO: 12
and a light chain variable region as shown in SEQ ID NO:20;
a heavy chain variable region as shown in SEQ ID NO: 14
and a light chain variable region as shown in SEQ ID NO:22;
a heavy chain variable region as shown in SEQ ID NO:15
and a light chain variable region as shown in SEQ ID NO:23; or
amino acid sequences having up to 20, 18, 16, 14, 12, 10, 8, 6, 4, 2 or 1 conservative amino acid substitution(s) in each group of the foregoing sequences.

In a further preferred embodiment, the humanized anti-human PD-L1 monoclonal antibody or a functional fragment thereof has a heavy chain variable region and a light chain variable region selected from a combination of
a heavy chain variable region as shown in SEQ ID NO:9
and a light chain variable region as shown in SEQ ID NO:17;
a heavy chain variable region as shown in SEQ ID NO:12
and a light chain variable region as shown in SEQ ID NO:20;
a heavy chain variable region as shown in SEQ ID NO: 14
and a light chain variable region as shown in SEQ ID NO:22; or
a heavy chain variable region as shown in SEQ ID NO: 15
and a light chain variable region as shown in SEQ ID NO:23.

In a preferred embodiment, the humanized anti-human PD-L1 monoclonal antibody or a functional fragment thereof has a heavy chain variable region and a light chain variable region selected from a combination of
a heavy chain variable region as shown in SEQ ID NO:9
and a light chain variable region as shown in SEQ ID NO:17;
a heavy chain variable region as shown in SEQ ID NO: 12
and a light chain variable region as shown in SEQ ID NO:20; or
amino acid sequences having up to 20, 18, 16, 14, 12, 10, 8, 6, 4, 2 or 1 conservative amino acid substitution(s) in each group of the foregoing sequences.

In a further preferred embodiment, the humanized anti-human PD-L1 monoclonal antibody or a functional fragment thereof has a heavy chain variable region and a light chain variable region selected from a combination of
a heavy chain variable region as shown in SEQ ID NO:9
and a light chain variable region as shown in SEQ ID NO: 17; or
a heavy chain variable region as shown in SEQ ID NO: 12
and a light chain variable region as shown in SEQ ID NO:20.

In some embodiments, the humanized anti-human PD-L1 monoclonal antibody of the present invention or a functional fragment thereof has a dissociation constant $K_D$ from PD-L1 of less than about 3 nM. In another embodiment, the humanized anti-human PD-L1 monoclonal antibody or a functional fragment thereof has a dissociation constant $K_D$ from PD-L1 of less than about 2 nM, about 1.9 nM, about 1.8 nM, about 1.7 nM, about 1.6 nM, about 1.5 nM, about 1.4 nM, about 1.3 nM, about 1.2 nM, about 1.1 nM, about 1 nM, about 0.9 nM, about 0.8 nM, or about 0.7 nM. In a preferred embodiment, the humanized anti-human PD-L1 monoclonal antibody or a functional fragment thereof has a dissociation constant $K_D$ from PD-L1 of less than about 1 nM, about 0.9 nM, about 0.8 nM, or about 0.7 nM. In an embodiment, the humanized anti-human PD-L1 monoclonal antibody or a functional fragment thereof has a dissociation constant $K_D$ from PD-L1 of about 3 nM to about 0.8 nM. In a preferred embodiment, the humanized anti-human PD-L1 monoclonal antibody or a functional fragment thereof has a dissociation constant $K_D$ from PD-L1 of about 2 nM to about 1 nM. In another preferred embodiment, the humanized anti-human PD-L1 monoclonal antibody or a functional fragment thereof has a dissociation constant $K_D$ from PD-L1 of about 1 nM to about 0.8 nM.

In some embodiments, the humanized anti-human PD-L1 monoclonal antibody of the present invention or a functional fragment thereof specifically relieves the negative immune regulation by PD-L1 and activates T cells to secrete cytokines.

The present invention provides a humanized anti-human PD-L1 monoclonal antibody or a functional fragment thereof, which can specifically bind to PD-L1, and is characterized in that it relieves the immunosuppression by indirectly blocking the interaction between PD1 and PD-L1. In some embodiments, the humanized anti-human PD-L1 monoclonal antibody or a functional fragment thereof can activate T cells to secrete cytokines. In some embodiments, the humanized anti-human PD-L1 monoclonal antibody or a functional fragment thereof can activate T cells to secrete IL-2. In other embodiments, the humanized anti-human PD-L1 monoclonal antibody or a functional fragment thereof can activate T cells to secrete IFN-γ.

In some embodiments, the humanized anti-human PD-L1 monoclonal antibody or a functional fragment thereof includes a heavy chain variable region having an amino acid sequence selected from amino acid sequences having at least 80% sequence identity to SEQ ID NO:9, SEQ ID NO:10, SEQ ID NO:11, SEQ ID NO:12, SEQ ID NO:13, SEQ ID NO:14, SEQ ID NO: 15 or SEQ ID NO:16; and a light chain variable region having an amino acid sequence selected from amino acid sequences having at least 80% sequence identity to SEQ ID NO:17, SEQ ID NO:18, SEQ ID NO:19, SEQ ID NO:20, SEQ ID NO:21, SEQ ID NO:22, SEQ ID NO:23 or SEQ ID NO:24.

In an embodiment, the humanized anti-human PD-L1 monoclonal antibody or a functional fragment thereof has a heavy chain variable region and a light chain variable region selected from a combination of
- a heavy chain variable region as shown in SEQ ID NO:9 and a light chain variable region as shown in SEQ ID NO:17;
- a heavy chain variable region as shown in SEQ ID NO:10 and a light chain variable region as shown in SEQ ID NO:18;
- a heavy chain variable region as shown in SEQ ID NO:11 and a light chain variable region as shown in SEQ ID NO:19;
- a heavy chain variable region as shown in SEQ ID NO:12 and a light chain variable region as shown in SEQ ID NO:20;
- a heavy chain variable region as shown in SEQ ID NO:13 and a light chain variable region as shown in SEQ ID NO:21;
- a heavy chain variable region as shown in SEQ ID NO:14 and a light chain variable region as shown in SEQ ID NO:22;
- a heavy chain variable region as shown in SEQ ID NO: 15 and a light chain variable region as shown in SEQ ID NO:23;
- a heavy chain variable region as shown in SEQ ID NO: 16 and a light chain variable region as shown in SEQ ID NO:24; or
- amino acid sequences having up to 20, 18, 16, 14, 12, 10, 8, 6, 4, 2 or 1 conservative amino acid substitution(s) in each group of the foregoing sequences.

In a preferred embodiment, the humanized anti-human PD-L1 monoclonal antibody or a functional fragment thereof has a heavy chain variable region and a light chain variable region selected from a combination of
- a heavy chain variable region as shown in SEQ ID NO:9 and a light chain variable region as shown in SEQ ID NO:17;
- a heavy chain variable region as shown in SEQ ID NO:10 and a light chain variable region as shown in SEQ ID NO:18;
- a heavy chain variable region as shown in SEQ ID NO:11 and a light chain variable region as shown in SEQ ID NO:19;
- a heavy chain variable region as shown in SEQ ID NO: 12 and a light chain variable region as shown in SEQ ID NO:20;
- a heavy chain variable region as shown in SEQ ID NO: 13 and a light chain variable region as shown in SEQ ID NO:21;
- a heavy chain variable region as shown in SEQ ID NO: 14 and a light chain variable region as shown in SEQ ID NO:22;
- a heavy chain variable region as shown in SEQ ID NO:15 and a light chain variable region as shown in SEQ ID NO:23; or
- a heavy chain variable region as shown in SEQ ID NO:16 and a light chain variable region as shown in SEQ ID NO:24.

In another preferred embodiment, the humanized anti-human PD-L1 monoclonal antibody or a functional fragment thereof has a heavy chain variable region and a light chain variable region selected from a combination of
- a heavy chain variable region as shown in SEQ ID NO:9 and a light chain variable region as shown in SEQ ID NO:17;
- a heavy chain variable region as shown in SEQ ID NO: 12 and a light chain variable region as shown in SEQ ID NO:20; or
- amino acid sequences having up to 20, 18, 16, 14, 12, 10, 8, 6, 4, 2 or 1 conservative amino acid substitution(s) in each group of the foregoing sequences.

In a further preferred embodiment, the humanized anti-human PD-L1 monoclonal antibody or a functional fragment thereof has a heavy chain variable region and a light chain variable region selected from a combination of
- a heavy chain variable region as shown in SEQ ID NO:9 and a light chain variable region as shown in SEQ ID NO:17 or
- a heavy chain variable region as shown in SEQ ID NO: 12 and a light chain variable region as shown in SEQ ID NO:20.

In any of the foregoing embodiments, the humanized anti-human PD-L1 monoclonal antibody or a fragment thereof provided in the present invention may include 1, 2, 3, 4 or 5 conservative amino acid substitution(s). Preferably, the antibody of the present invention or a fragment thereof include 1, 2, or 3 conservative amino acid substitution(s).

The humanized anti-human PD-L1 monoclonal antibody or a fragment thereof provided in the present invention may include a heavy chain constant region of human IgG1, IgG2, IgG3 or IgG4 or a variant thereof. In some embodiments, the humanized anti-human PD-L1 monoclonal antibody or a functional fragment thereof has a light chain further comprising a constant region of human κ, or λ chain or a variant thereof.

The humanized anti-human PD-L1 monoclonal antibody or a fragment thereof provided in the present invention is a monoclonal antibody, a single-domain antibody, scFv, a Fab fragment, a Fv fragment, a F(ab)' fragment, F(ab')2 fragment, a bispecific antibody, an immunoconjugate or a combination thereof.

In any of the foregoing embodiments, the humanized anti-human PD-L1 monoclonal antibody or a fragment thereof provided in the present invention may include a human heavy chain constant region, or a variant thereof having up to 20 conservative amino acid substitutions; and/or a human light chain constant region or a variant thereof having up to 20 conservative amino acid substitutions. In some embodiments, the variant may have up to 10 conservative amino acid substitutions. In some embodiments, the variant may have up to 5 conservative amino acid substitutions. In some embodiments, the variant may have up to 3 conservative amino acid substitutions.

In an embodiment, the present invention provides an isolated polynucleotide, which encodes the humanized anti-human PD-L1 monoclonal antibody of the present invention or a functional fragment thereof.

In an embodiment, the polynucleotide comprises a heavy chain coding sequence encoding the heavy chain variable region of the humanized anti-human PD-L1 monoclonal antibody of the present invention, and a light chain coding sequence encoding the light chain variable region of the humanized anti-human PD-L1 monoclonal antibody of the present invention.

In another aspect, the present invention provides an expression vector comprising the polynucleotide.

In another aspect, the present invention provides a host cell comprising the expression vector.

In an embodiment, the host cell is HEK293-6E cells.

In another aspect, the present invention provides use of the humanized anti-human PD-L1 monoclonal antibody or a functional fragment thereof, the polynucleotide, the expression vector or the host cell in the preparation of an anti-tumor drug.

In another aspect, the present invention provides use of the humanized anti-human PD-L1 monoclonal antibody or a functional fragment thereof, the polynucleotide, the expression vector or the host cell in the treatment of tumors.

In another aspect, the present invention provides the humanized anti-human PD-L1 monoclonal antibody or a functional fragment thereof, the polynucleotide, the expression vector or the host cell useful in the treatment of tumors.

In another aspect, the present invention provides an anti-tumor pharmaceutical composition, which comprises an effective amount of the humanized anti-human PD-L1 monoclonal antibody or a functional fragment thereof, and a pharmaceutically acceptable carrier.

In an embodiment, the present invention provides a method for enhancing an anti-tumor response in a subject in need thereof, which comprises administering to the subject a therapeutically effective amount of the humanized anti-human PD-L1 monoclonal antibody of the present invention or a functional fragment thereof. In another embodiment, the present invention provides a method for alleviating tumors or inhibiting the growth of tumor cells in a subject in need thereof, which comprises administering to the subject a therapeutically effective amount of the humanized anti-human PD-L1 monoclonal antibody of the present invention or a functional fragment thereof. In another embodiment, the present invention provides a method for treating tumors in a subject in need thereof, which comprises administering to the subject a therapeutically effective amount of the humanized anti-human PD-L1 monoclonal antibody of the present invention or a functional fragment thereof.

The tumor in the present invention is selected from the group consisting of: lymphoma, leukemia, melanoma, glioma, breast cancer, lung cancer, bowel cancer, bone cancer, ovarian cancer, bladder cancer, kidney cancer, liver cancer, stomach cancer, testicular cancer, salivary gland cancer, thyroid cancer, thymic cancer, epithelial cancer, head or neck cancer, gastric cancer, pancreatic cancer or a combination thereof, preferably breast cancer, lung cancer, gastric cancer, bowel cancer, kidney cancer, melanoma, bladder cancer and pancreatic cancer, and further preferably colon cancer, pancreatic cancer, gastric cancer, non-small cell lung cancer, melanoma, bladder cancer and kidney cancer.

In some embodiments, the antibody or a fragments thereof disclosed herein can be administered to a subject by at least one route selected from the group consisting of parenteral, subcutaneous, intramuscular, intravenous, intraarticular, intrabronchial, intraabdominal, intracapsular, intrachondral, intracavitary, intracoelomic, intracerebellar, intraventricular, intracolic, intracervical, intragastric, intrahepatic, intramyocardial, intraosseous, intrapelvic, intrapericardial, intraperitoneal, intrapleural, intraprostatic, intrapulmonary, intrarectal, intrarenal, intraretinal, intraspinal, intrasynovial, intrathoracic, intratympanic, intrauterine, intravesical, intravitreal, bolus injection, subconjunctival, transvaginal, transrectal, transbuccal, sublingual, intranasal, intratumor and transdermal.

In some embodiments, the humanized anti-human PD-L1 monoclonal antibody or a functional fragment thereof disclosed in the present invention can be administered to a subject in need thereof in combination with one or more additional therapeutic agent(s). In some embodiments, the antibody and a fragment thereof can be administered to the subject before, during, and/or after the administration of the additional therapeutic agent to the subject. In some embodiments, the additional therapeutic agent is a chemotherapeutic agent, a radiotherapeutic agent, a cytokine, an anti-angiogenic drug, an antibody or a fragment thereof, or any other additional therapeutic agents that are useful in the treatment of the disease to be treated. In some embodiments, when administered together whether concurrently or sequentially, the humanized anti-human PD-L1 monoclonal antibody or a functional fragment thereof and another therapeutic agent show a therapeutically synergistic effect. In some embodiments, the humanized anti-human PD-L1 monoclonal antibody or a functional fragment thereof and the additional therapeutic agent are administered in separate preparations. In some other embodiments, the humanized anti-human PD-L1 monoclonal antibody or a functional fragment thereof and the additional therapeutic agent are administered in the same preparation. In some embodiments, the humanized anti-human PD-L1 monoclonal antibody or a functional fragment thereof provided in the present invention enhances the immunomodulatory effect of one or more additional therapeutic agent(s). In other embodiments, the one or more additional therapeutic agents enhance the effect of the humanized anti-human PD-L1 monoclonal antibody or a functional fragment thereof.

In some embodiments, the humanized anti-human PD-L1 monoclonal antibody or a functional fragment thereof is used in combination with other immune checkpoint inhibitors to synergistically stimulate the immune response. In some other embodiments, the combination of the humanized anti-human PD-L1 monoclonal antibody or a functional fragment thereof and the immune checkpoint antibody capable of blocking the interaction between PD-1 and PD-L1 synergistically stimulates the immune response. In some embodiments, the humanized anti-human PD-L1 monoclonal antibody or a functional fragment thereof is used in combination with another PD-L1 antibody to synergistically stimulate the immune response. In some other embodiments, the humanized anti-human PD-L1 monoclonal antibody or a functional fragment thereof is used in combination with another PD-1 antibody to synergistically stimulate the immune response. In a specific embodiment, the humanized anti-human PD-L1 monoclonal antibody or a functional fragment thereof is used in combination with atezolizumab (trade name: Tecentriq) to synergistically stimulate the immune response, to activate T cells to secrete cytokines. In a specific embodiment, the combination of the humanized anti-human PD-L1 monoclonal antibody or a functional fragment thereof with atezolizumab synergistically stimulates the immune response, to activate T cells to secrete IL-2. In a specific embodiment, the combination of the humanized anti-human PD-L1 monoclonal antibody or a functional fragment thereof with atezolizumab synergistically stimulates the immune response, to activate T cells to secrete IFN-γ.

In some embodiments, the humanized anti-human PD-L1 monoclonal antibody or a functional fragment thereof is used in combination with other immune checkpoint inhibitors to synergistically inhibit the tumor growth. In some embodiments, the humanized anti-human PD-L1 monoclonal antibody or a functional fragment thereof is used in combination with another PD-L1 antibody to synergistically inhibit the tumor growth. In some other embodiments, the humanized anti-human PD-L1 monoclonal antibody or a functional fragment thereof is used in combination with another PD-1 antibody to synergistically inhibit the tumor growth. In some specific embodiments, the humanized anti-human PD-L1 monoclonal antibody or a functional fragment thereof is used in combination with atezolizumab to synergistically inhibit the tumor growth. In some other specific embodiments, the humanized anti-human PD-L1 monoclonal antibody or a functional fragment thereof is used in combination with pembrolizumab (trade name Keytruda) to synergistically inhibit the tumor growth. In some embodiments, a low dose of the humanized anti-human PD-L1 monoclonal antibody or a functional fragment thereof is used in combination with a low dose of another PD-L1 antibody or PD-1 antibody to synergistically inhibit the tumor growth. The tumor is selected from colon cancer, pancreatic cancer, gastric cancer, non-small cell lung cancer, melanoma, bladder cancer and kidney cancer, and preferably colon cancer.

In another aspect, the present invention provides a method for preparing the humanized anti-human PD-L1 monoclonal antibody or a functional fragment thereof, which comprises (1) humanizing the murine antibody, and obtaining variable region coding sequences of the light chain and the heavy chain of the humanized anti-human PD-L1 monoclonal antibody or a functional fragment thereof; and (2) using the variable region coding sequences in recombinant antibody production to obtain the functional humanized anti-human PD-L1 monoclonal antibody or a functional fragment thereof.

The present invention provides a suppression relieving antibody against PD-L1, which enhances the immune response of T cells to various antigens for tumor immunotherapy. The effect of this antibody is not achieved by directly blocking the interaction between PD-1 and PD-L1, presenting a new mechanism of immune checkpoint regulation.

The humanized anti-human PD-L1 monoclonal antibody provided in the present invention has high affinity and specificity for PD-L1, and can stimulate T cells to secrete cytokines, for example, specifically relieve the negative immune regulation by PD-L1 and activate T cells to secrete cytokines. Therefore, the functional humanized anti-human PD-L1 monoclonal antibody provided in the present invention can activate T cells by regulating the PD-L1 signaling pathway, thereby achieving the purpose of tumor immunotherapy.

BRIEF DESCRIPTION OF THE DRAWINGS

FIGS. 5A-5D show the thermal stability analysis of purified monoclonal antibodies, specifically thermal stability analysis by nr-SDS of humanized anti-human PD-L1 monoclonal antibodies (treated at 40° C. for 2 weeks), including AH01946-0/14 days (FIG. 5A), AH01950-0/14 days (FIG. 5B), AH01963-0/14 days (FIG. 5C), and AH02029-0/14 days (FIG. 5D);

DETAILED DESCRIPTION

Figure 1B:
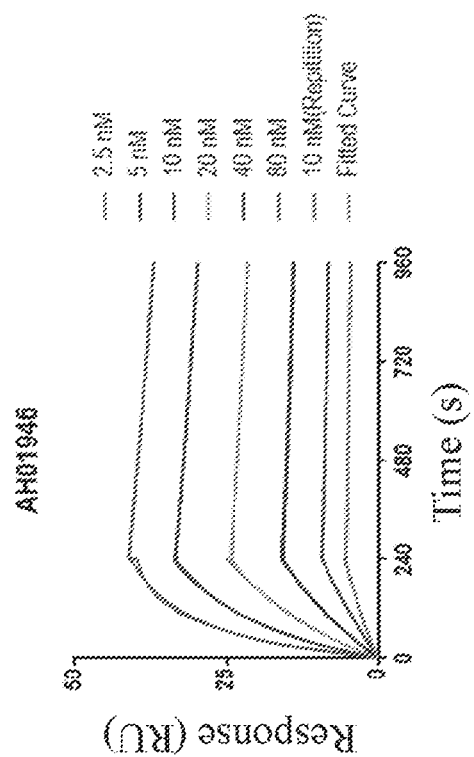
FIGS. 1A-1I show the affinity determination of humanized anti-human PD-L1 monoclonal antibodies, including: a chimeric antibody (FIG. 1A), AH01946 (FIG. 1B), AH01947 (FIG. 1C), AH01950 (FIG. 1D), AH01963 (FIG. 1E), AH01964 (FIG. 1F), AH02029 (FIG. 1G), AH02030 (FIG. 1H), and AH02033 (FIG. 1I)
Figure 1D:
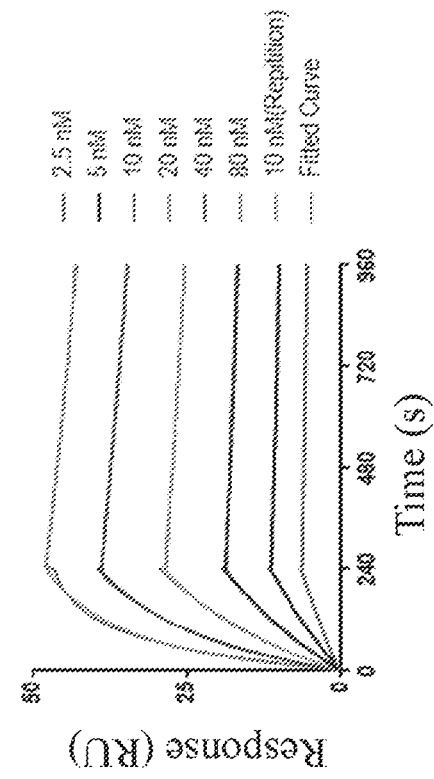
Figure 1A:
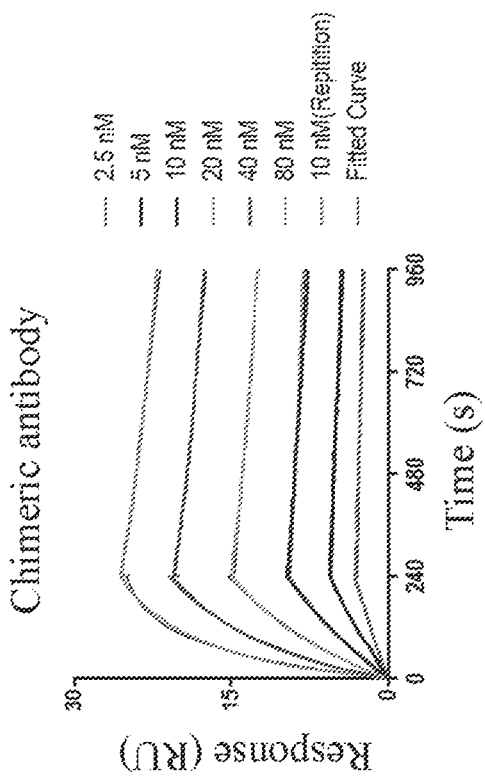
Figure 1C:
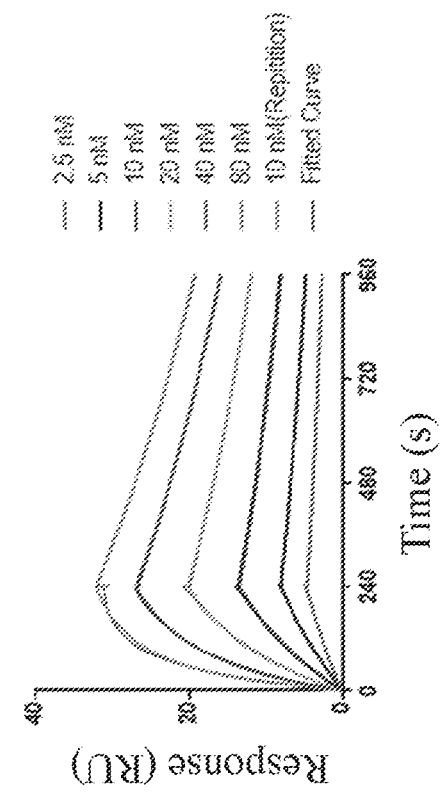
Figure 1E:
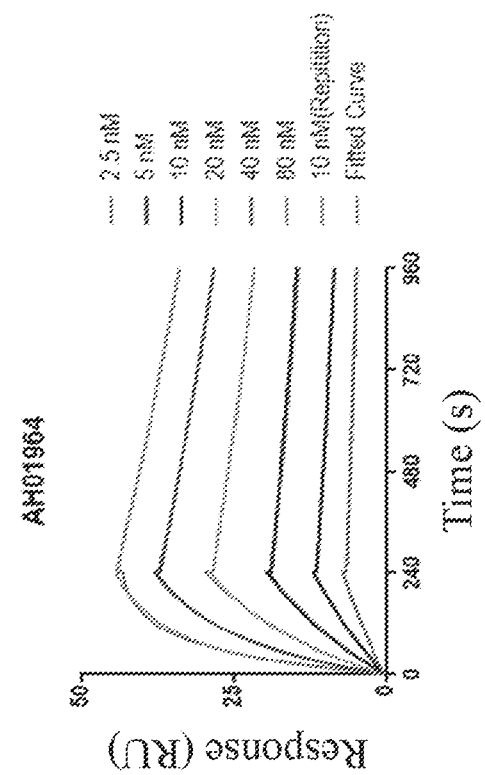
Figure 1F:
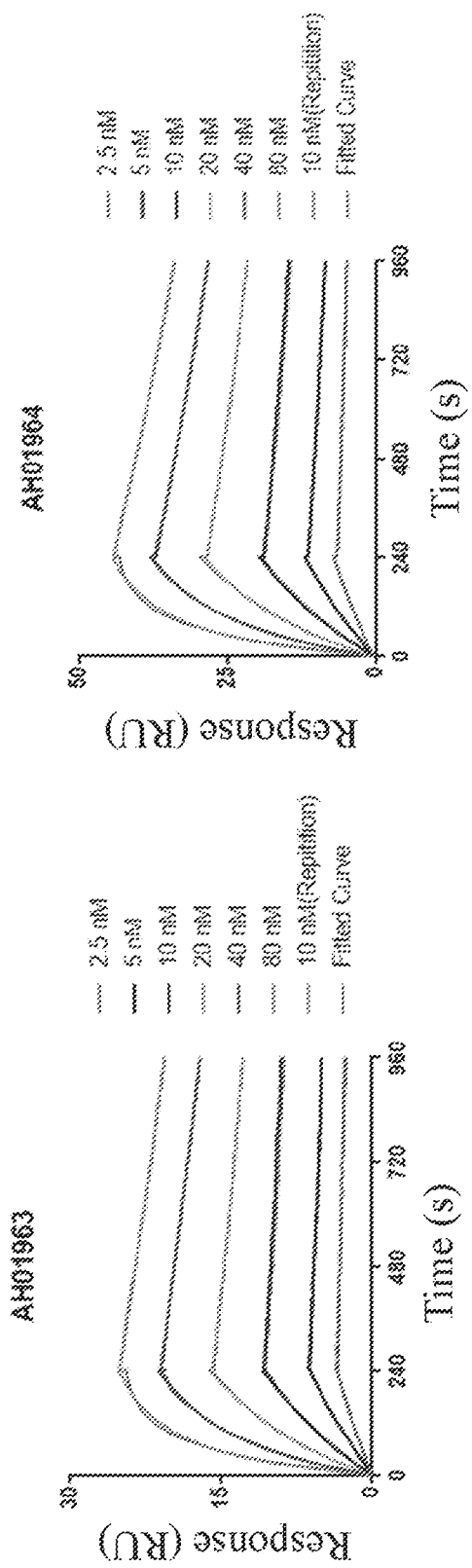
Figure 1G:
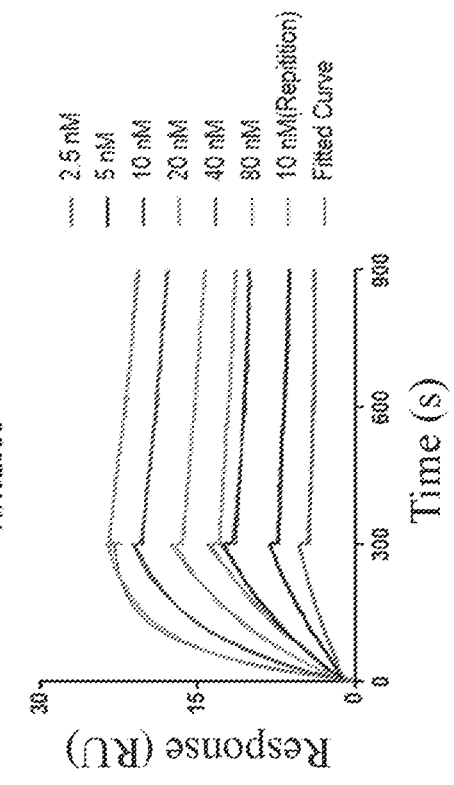
Figure 1H:
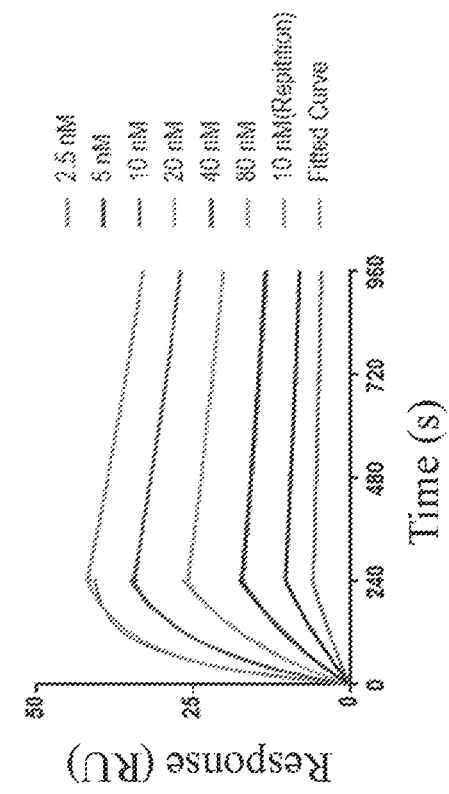
Figure 1I:
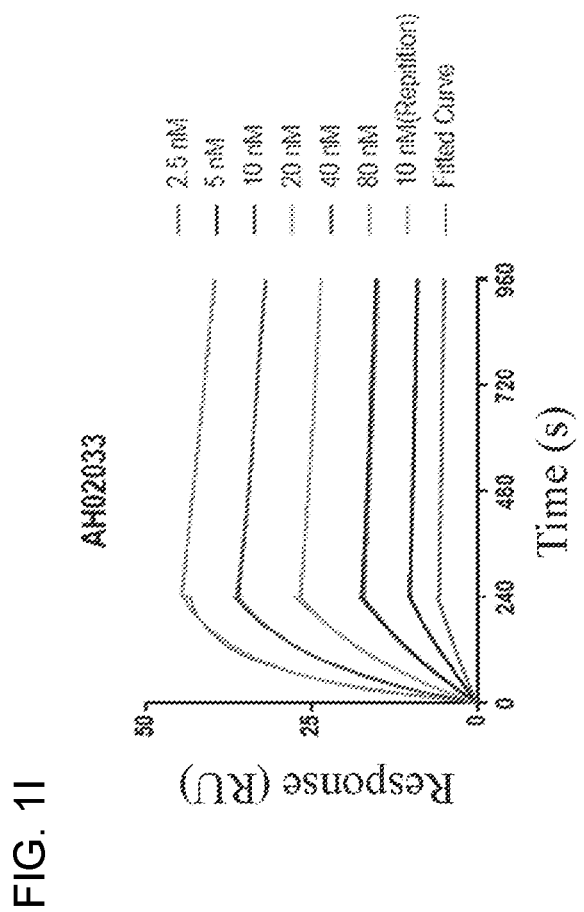
Figure 2A:
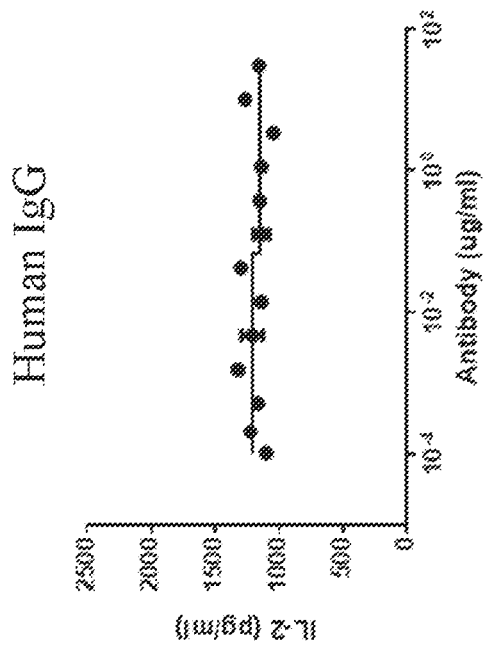
FIGS. 2A-2F show the detection of cell activity function in the presence of humanized anti-human PD-L1 monoclonal antibodies, including specifically the positive control antibody Tecentriq (FIG. 2A), the negative control antibody human IgG (FIG. 2B), AH01946 (FIG. 2C), AH01950 (FIG. 2D), AH01963 (FIG. 2E), and AH02029 (FIG. 2F)
Figure 2B:
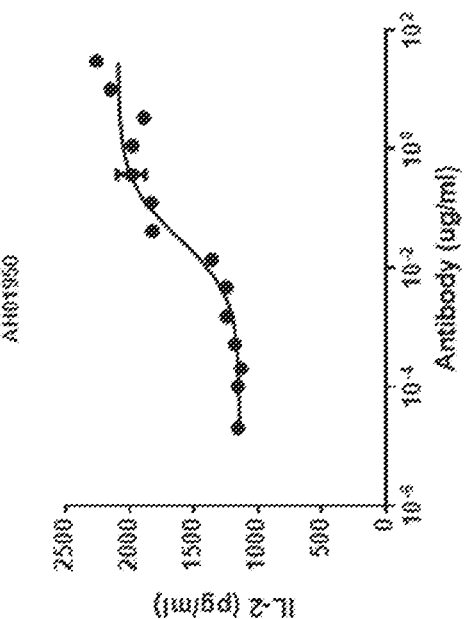
Figure 2C:
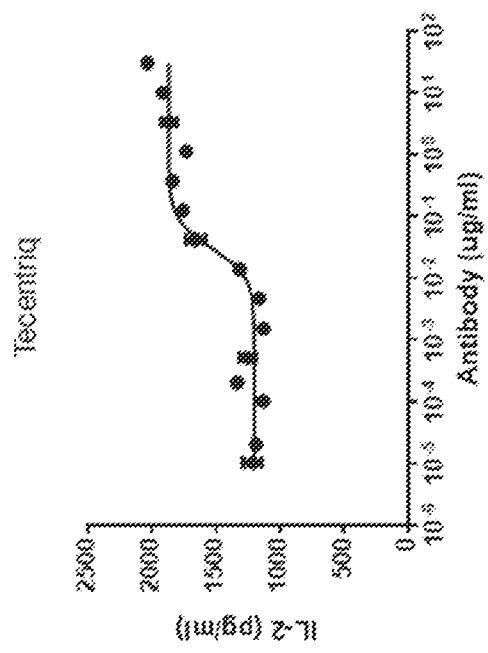
Figure 2D:
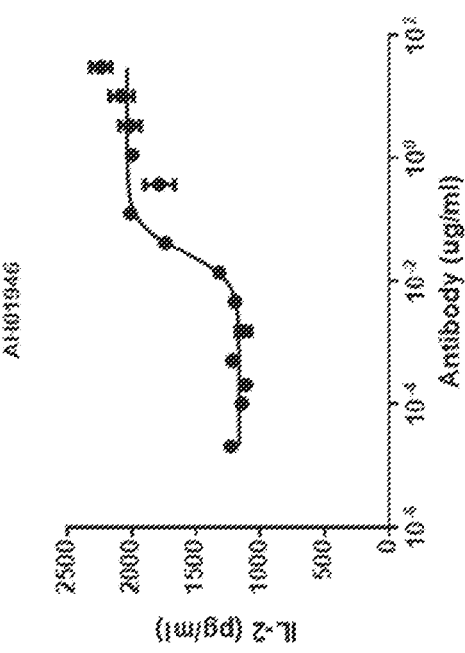
Figure 2F:
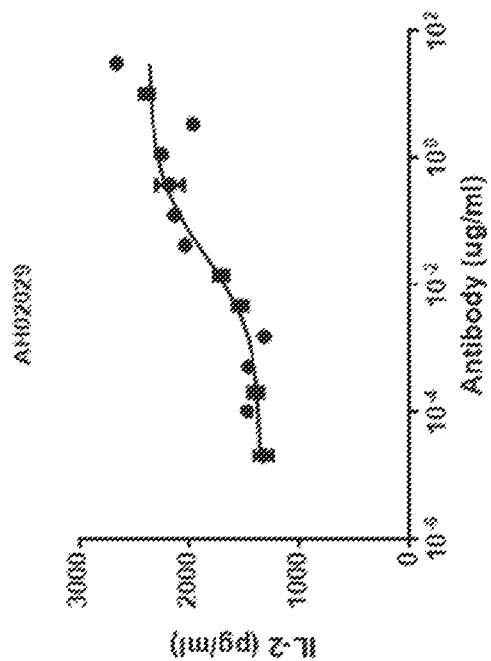
Figure 2E:
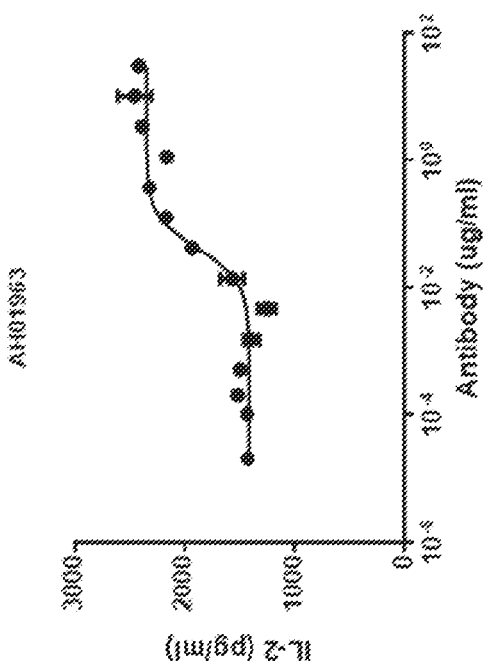
Figure 3B:
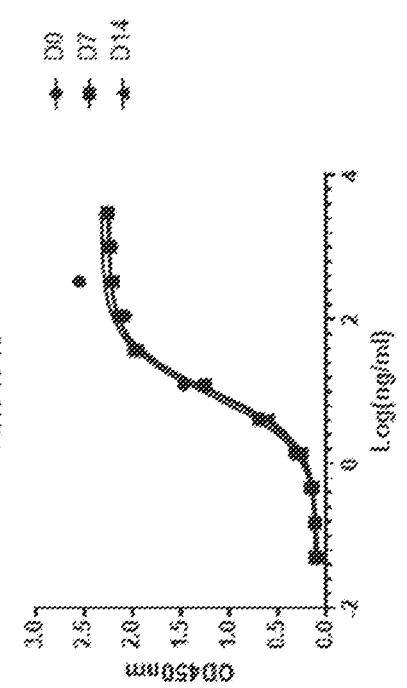
FIGS. 3A-3E show the thermal stability analysis of purified monoclonal antibodies, specifically thermal stability analysis by ELISA of humanized anti-human PD-L1 monoclonal antibodies (treated at 40° C. for 1-2 weeks), including chimeric antibody-0/7/14 days-ELISA (FIG. 3A), AH01946-0/7/14 days-ELISA (FIG. 3B), AH01950-0/7/14 days-ELISA (FIG. 3C), AH01963-0/7/14 days-ELISA (FIG. 3D), and AH02029-0/7/14 days-ELISA (FIG. 3E)
Figure 3D:
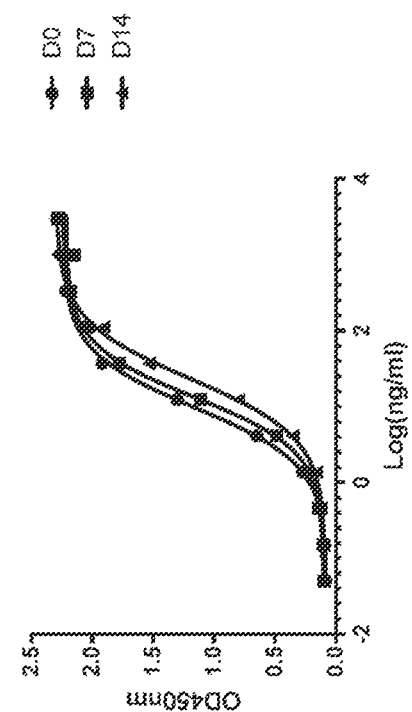
Figure 3A:
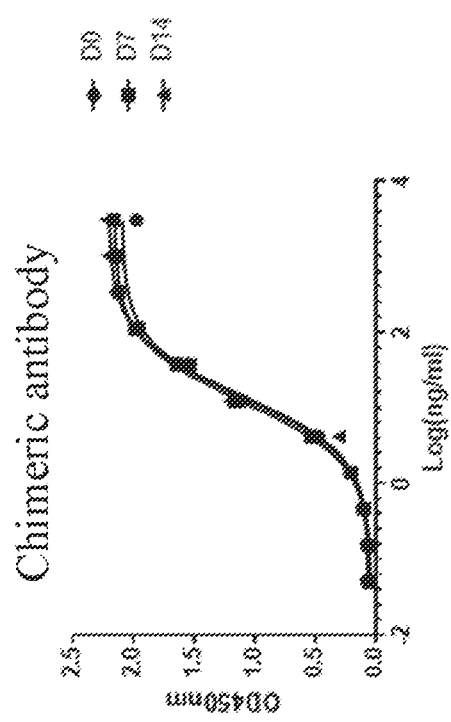
Figure 3C:
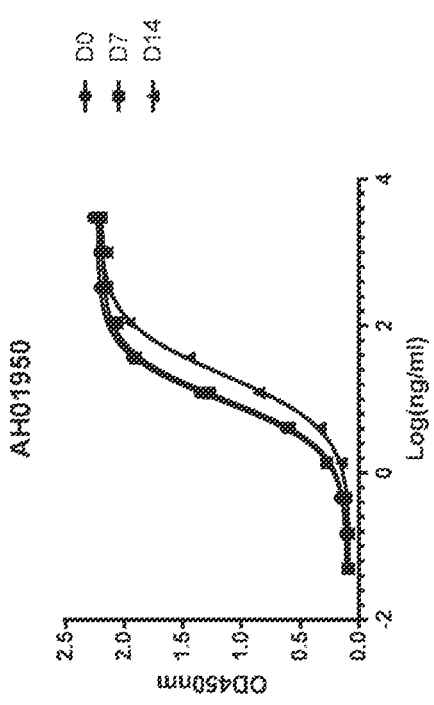
Figure 3E:
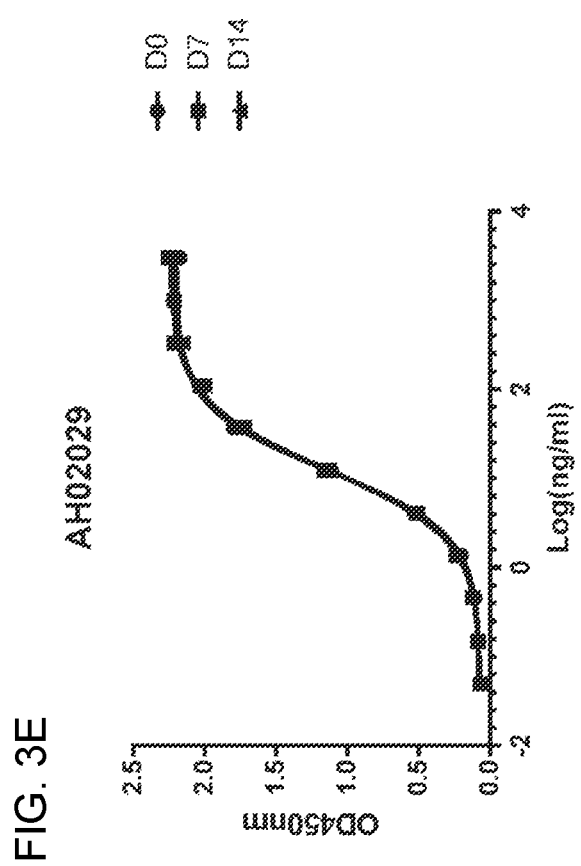
Figure 4B:
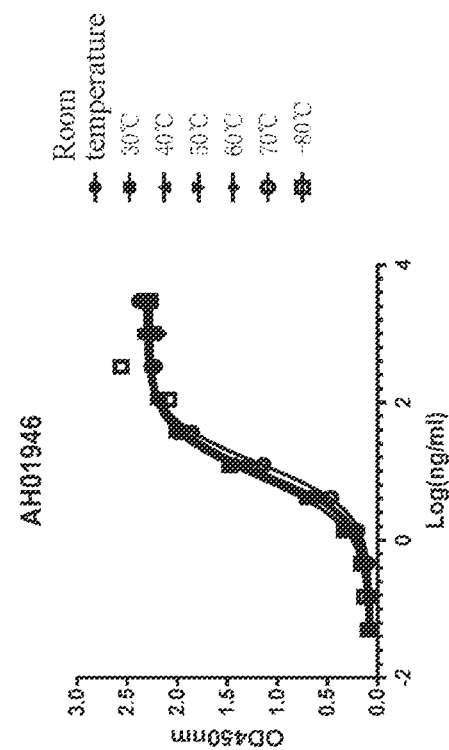
FIGS. 4A-4E show the thermal stability analysis of purified monoclonal antibodies, specifically thermal stability analysis by ELISA of humanized anti-human PD-L1 monoclonal antibodies (treated for 20 min under various temperature conditions), including chimeric antibody-ELISA (FIG. 4A), AH01946-ELISA (FIG. 4B), AH01950-ELISA (FIG. 4C), AH01963-ELISA (FIG. 4D), and AH02029-ELISA (FIG. 4E)
Figure 4D:
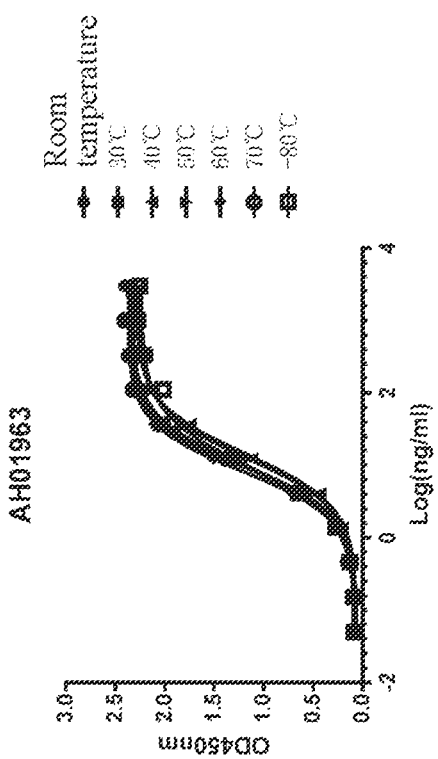
Figure 4A:
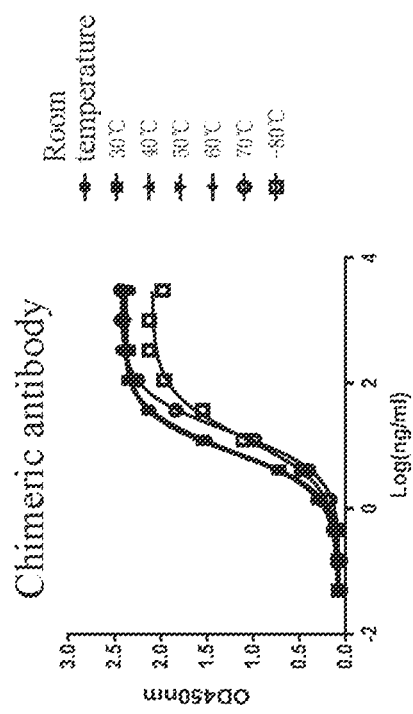
Figure 4C:
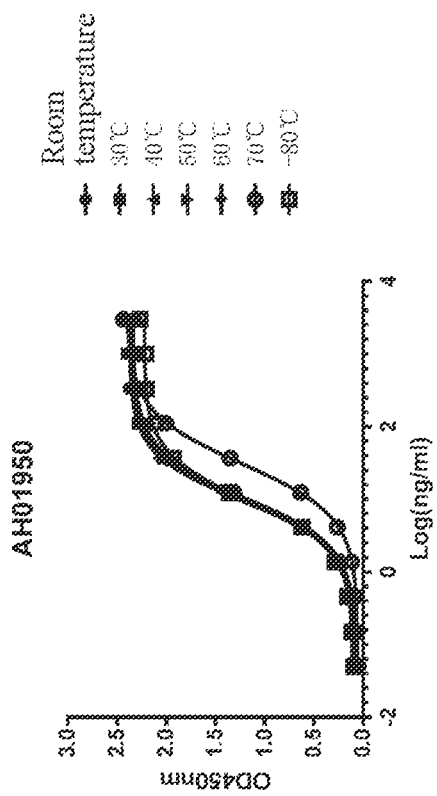
Figure 4E:
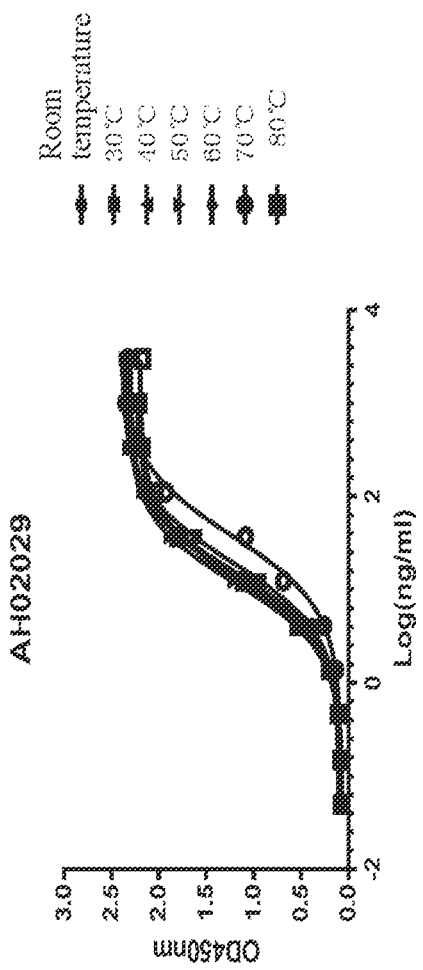

Unless otherwise specified, the technical and scientific terms used in the present invention have the meanings commonly understood by those skilled in the art to which the present invention belongs.

As used herein, the term "antibody" refers to an immunoglobulin molecule, which is usually a tetramer consisting of two identical heavy chains and two identical light chains connected to each other by disulfide bonds. According to conservative differences in amino acid sequences, the heavy chain and the light chain are divided into a variable region (V) at the amino terminal and a constant region (C) at the carboxyl terminal. In the variable regions of the heavy chain and the light chain, there are three partial regions with a higher degree of variation in the amino acid composition and arrangement order, which are the key positions for the antibody to bind to the antigen, and such region is also called a complementary determining region (CDR). Herein, the three heavy chain complementary determining regions are called HCDR1, HCDR2 and HCDR3 respectively, and the three light chain complementary determining regions are called LCDR1, LCDR2 and LCDR3 respectively. The variable regions of a heavy chain and a light chain interact to form an antigen binding site (Fv). According to amino acid sequences of the heavy chain constant regions, antibodies can be divided into different classes. There are five main types of intact antibodies: IgA, IgD, IgE, IgG and IgM, and some of these antibodies can be further divided into subclasses, for example, IgG1, IgG2, IgG3, IgG4, IgA1 and IgA2. The subunit structures and three-dimensional conformations of different classes of immunoglobulins are known in the art. The present invention is intended to include antibodies of any of the classes or subclasses.

The term "antibody fragment" as used herein refers to an antigen-binding fragment of an antibody and an antibody analog, which usually includes at least a part of the antigen-binding region or variable region (for example, one or more CDRs) of the parental antibody. The antibody fragment retains at least some of the binding specificity of the parent antibody. For example, antibody fragments capable of binding PD-L1 or a moiety thereof, include, but are not limited to, sdAb (single-domain antibody), Fab (for example, obtained by papain digestion of an antibody), F(ab') 2 (for example, obtained by pepsin digestion), Fv or scFv (for example, obtained by molecular biology techniques).

As used herein, the term "monoclonal antibody" refers to a uniform antibody that only targets a specific epitope. Compared with ordinary polyclonal antibody preparations which typically include different antibodies against different antigenic determinants (epitopes), each monoclonal antibody is directed against a single antigenic determinant on an antigen. The modifier "monoclonal" refers to the uniform characteristics of an antibody, and is not interpreted as an antibody that needs to be produced by any specific method. The monoclonal antibodies of the present invention are preferably produced by a DNA recombination method or obtained by a screening method described elsewhere herein.

As used herein, the term "isolated polynucleotide" refers to a polynucleotide that does not occur naturally in nature, including polynucleotides isolated from nature (including organisms) through biological techniques and artificially synthesized polynucleotides. The isolated polynucleotide may be genomic DNA, cDNA, mRNA or other synthetic RNA, or a combination thereof. Herein provided is a number of nucleotide sequences encoding the heavy chain variable region and the light chain variable region of a humanized anti-PD-L1 monoclonal antibody. It should be noted that those skilled in the art can design nucleotide sequences that are not completely identical to the nucleotide sequences provided above, but both encode the same amino acid sequence according to the amino acid sequences of the heavy chain variable region and the light chain variable region provided herein on the basis of codon degeneracy. These modified nucleotide sequences are also included in the scope of the present invention.

As used herein, the "modification" of an amino acid residue/position refers to a primary amino acid sequence change relative to an original amino acid sequence, wherein the change comes from a change in the sequence involving an amino acid residue/position. For example, typical modifications include substituting (such as conservative or non-conservative substitution) a residue (at the position) with another amino acid, inserting one or more (generally less than 5 or 3) amino acids into a position adjacent to the residue/position and deleting the residue/position. "Amino acid substitution" or a change thereof refers to substitution of an existing amino acid residue with different amino acid residues in a predetermined (original) amino acid sequence. Relative to a polypeptide containing an original (or "wild-type") amino acid sequence, the modification generally preferably produces at least one physiological and biochemical activity change of a variant polypeptide. For example, for antibodies, the changed physiological and biochemical activity may be the binding affinity, binding capacity and/or binding effect for a target molecule. "Conservative amino acid substitutions" refer to amino acid substitutions known to those skilled in the art, which can be made without changing the biological activity of the resulting molecule. Generally speaking, those skilled in the art can recognize that a single amino acid substitution in a non-essential region of a polypeptide does not substantially change the biological activity (see, for example, Watson et al., Molecular Biology of the Gene, The Benjamin/Cummings Pub. Co., p. 224 (fourth edition, 1987)). Such exemplary substitutions are preferably carried out in accordance with the substitutions shown below:

| Exemplary conservative amino acid substitutions | |
|---|---|
| Original residue | Conservative substitution |
| Ala(A) | Gly; Ser |
| Arg(R) | Lys; His |
| Asn(N) | Gln; His |
| Asp(D) | Glu; Asn |
| Cys(C) | Ser; Ala |
| Gln(Q) | Asn |
| Glu(E) | Asp; Gln |
| Gly(G) | Ala |
| His(H) | Asn; Gln |
| Ile(I) | Leu; Val |
| Leu(L) | Ile; Val |
| Lys(K) | Arg; His |
| Met(M) | Leu; Ile; Tyr |
| Phe(F) | Tyr; Met; Leu |

The "percent (%) amino acid sequence identity" of a peptide or polypeptide sequence is defined as the percentage of amino acid residues in a candidate sequence identical to the amino acid residues in a specific peptide or polypeptide sequence after the sequences are compared and gaps are introduced when necessary to obtain the maximum percent sequence identity without considering any conservative substitutions as part of the sequence identity. Sequence comparison can be performed in a variety of ways within the skill of the art to determine percent amino acid sequence identity, for example, publicly available computer software such as BLAST, BLAST-2, ALIGN or Megalign (DNASTAR) software is used. Those skilled in the art can determine appropriate parameters for measuring the comparison, including any algorithm required to obtain the maximum comparison over the entire length of the sequences being compared.

When referring to polynucleotide, the term "vector" as used herein refers to any molecule (such as nucleic acid, plasmid or virus) used to transfer nucleotide coding information into a host cell. The term "expression vector" or "expression cassette" refers to a vector suitable for expressing a target gene (nucleotide sequence to be expressed) in a host cell, and usually includes a target gene, a promoter, a terminator, a marker gene and other parts.

The term "host cell" as used herein refers to a cell that has been or is capable of being transformed with a nucleic acid sequence and thereby expressing a selected target gene. The term includes the offspring of a parent cell, regardless of whether the offspring and the original parent cell are the same in morphology or genetic composition, as long as the offspring has the selected target gene. Commonly used host cells include bacteria, yeast, mammalian cells and the like.

The term "transfection" as used herein refers to the uptake of foreign or exogenous DNA by cells, and this technique can be used to introduce one or more foreign DNA portions into a suitable host cell. Physical and chemical methods (such as calcium chloride treatment) can be used to induce cells to stay in a physiological state that is optimal for ingesting and accommodating foreign DNA, that is, "competence".

When referring to a ligand/receptor, antibody/antigen or other binding pairs herein, "specific" binding refers to determining whether a binding reaction of a protein such as PD-1 is present in a heterogeneous population of the protein and/or other biological reagents. Therefore, under specified conditions, a specific ligand/antigen binds to a specific receptor/antibody without substantially binding to other proteins present in a sample.

When "administering" and "treating" is used with reference to animals, humans, test subjects, cells, tissues, organs, or biological fluids, it means that an exogenous drug, therapeutic agent, diagnostic agent or composition is brought into contact with animals, humans, subjects, cells, tissues, organs or biological fluids. "Administration" and "treatment" can refer to, for example, a treatment method, a pharmacokinetic method, a diagnostic method, a research method, and an experimental method. Treating cells includes contacting the agent with the cells and contacting the agent with a fluid, where the fluid is in contact with the cells. "Administration" and "treatment" also means in-vitro and ex-vivo treatment of cells, for example, by an agent, a diagnostic agent, a binding composition, or other cells.

When referring to a pharmaceutical composition, the term "effective amount" as used herein refers to an amount that can produce function or activity on humans and/or animals and can be accepted by humans and/or animals. "Pharmaceutically acceptable carrier" refers to a carrier for administration, including various excipients, diluents, buffers and the like. These substances are suitable for administration to humans and/or animals without excessive side effects, and at the same time, the substances are suitable for maintaining the vitality of the drugs or active agents therein.

Unless specifically stated otherwise, the use of singular forms includes the plural forms. Unless specifically stated otherwise, the words "a" or "an" means "at least one." The use of "or" means "and/or" unless stated otherwise. The meaning of the phrase "at least one" is equivalent to the meaning of the phrase "one or more". In addition, the use of the term "including" and other forms such as "includes" and "included" is not limiting. In addition, unless specifically stated otherwise, the terms such as "element" or "component" include element or component that includes one unit and element or component that includes more than one units.

The term "about" as used herein means that the value is within an acceptable error range of a specific value determined by a person of ordinary skill in the art, and the value partly depends on how to measure or determine it (i.e. the limit of the measurement system). For example, in every practice in the art, "about" means the value is within a standard deviation of 1 or more than 1. Alternatively, "about" or "substantially comprise" may mean a range of up to 20%, preferably a range of up to 10%. Furthermore, especially for biological systems or processes, the term means at most an order of magnitude or at most 5 times the value. Unless otherwise specified, when a specific value appears in this application and the claims, the meaning of "about" or "substantially includes" should be assumed to be within an acceptable error range of a specific value.

Some aspects of the present invention will be described in detail below in conjunction with specific examples. Unless otherwise specified, the methods and materials in the examples described below are commercially available and conventional products.

Example 1: Humanization of Murine Anti-Human PD-L1 Antibody

1) A polynucleotide sequence was isolated from hybridoma cells, and sequenced to obtain the murine anti-human PD-L1 antibody mPD-L1Ab antibody sequence (where the CDR regions were underlined) (see, for example, SEQ ID NOs: 1-2).

```
mPD-L1Ab-VH
                                                    SEQ ID NO: 1
DVQLQESGPDLVKPSQSLSLTCTVTGYSITSGYTWHWIRQFPGNKLEWMG

YIHYSGSTKYNPSLKSRFSITRDTSKNQFFLQLNSMTAEDTATYYCARNS

LFASWGHGTLVTVSA, mPD-L1Ab-VL
                                                    SEQ ID NO: 2
DIVLTQSPASLAVSLGQRATISCRASESVDTYGDSFMHWFQQKPGQPPKL

LIYRASNLESGIPARFSGSGSRTDFTLTINPVEADDVATYYCQQSNEAPY

TFGGGTKLEIK,
```

2) Construction of CDR-grafted plasmid of anti-human PD-L1 antibody

From the IMGT human V gene (F+ORF+in-frameP) database, the human Germline antibody sequence with the highest homology was selected as the receiving vector for humanization based on the alignment. The three heavy chain complementarity determining regions HCDR1, HCDR2 and HCDR3 and the three light chain complementarity determining regions LCDR1, LCDR2 and LCDR3 in the murine antibody were transferred to corresponding positions respectively, and the sites of post-translational modification (PTM) were analyzed. The result is shown in Table 1. Sequence analysis shows that the three sites N99, W35, and M37 are hot sites for post-translational modification (see, for example, SEQ ID NOs: 3-4).

mPD-L1Ab-VH-GRAFTED
SEQ ID NO: 3
QVQLQESGPGLVKPSQTLSLTCTVSGYSITSGYTWHWIRQHPGKGLEWIG

YIHYSGSTKYNPSLKSRVTISVDTSKNQFSLKLSSVTAADTAVYYCARNS

LFASWGQGTLVTVSS, mPD-L1Ab-VL-GRAFTED
SEQ ID NO: 4
DIVMTQSPDSLAVSLGERATINCRASESVDTYGDSFMHWYQQKPGQPPKL

LIYRASNLESGVPDRFSGSGSGTDFTLTISSLQAEDVAVYYCQQSNEAPY

TFGGGTKLEIK,

TABLE 1

Risk analysis of sites of post-translational modification

| | mPD-L1Ab | |
|---|---|---|
| | VH | VL |
| Homology to human germline (%) | 75.50% IGHV4-30-4*01 | 65.30% IGKV4-1*01 |
| Additional cysteine | No | No |
| N-glycosylation | No | No |
| Asparagine Deamidation | N99 | No |
| Aspartate isomerization | No | No |
| Oxidation | W35 | M37 |
| Hydrolysis | No | No |

3) The phage libraries CBM, and 5BM (gray shading) were designed, and the Phage-Fab and FASEBA-Fab plasmids of the anti-human PD-L1 antibody mPD-L1Ab VH-VL were constructed, and the back mutation sites in the humanized antibody were screened (see, for example, SEQ ID NOs:5-8).

mPD-L1Ab_CBM
mPD-L1Ab-VH-CBM
SEQ ID NO: 5
QVQLQESGPGLVKPSQTLSLTCTVSGYSITSGYTWHWIRQHPGKGLEWMG

YIHYSGSTKYNPSLKSRFTISRDTSKNQFSLKLSSMTAADTAVYYCARNS

LFASWGQGTLVTVSS, mPD-L1Ab-VL-CBM
SEQ ID NO: 6
DIVLTQSPDSLAVSLGERATINCRASESVDTYGDSFMHWFQQKPGQPPKL

LIYRASNLESGVPDRFSGSGSGTDFTLTISSVQAEDVAVYYCQQSNEAPY

TFGGGTKLEIK, mPD-L1Ab_5BM
mPD-L1Ab-VH-5BM
SEQ ID NO: 7
QVQLQESGPGLVKPSQTLSLTCTVTGYSITSGYTWHWIRQHPGKGLEWMG

YIHYSGSTKYNPSLKSRFSITRDTSKNQFSLKLSSVTAADTAVYYCARNS

LFASWGQGTLVTVSS, mPD-L1Ab-VL-5BM
SEQ ID NO: 8
DIVLTQSPDSLAVSLGERATISCRASESVDTYGDSFMHWFQQKPGQPPKL

LIYRASNLESGIPDRFSGSGSGRTDFTLTISSLQAEDVAVYYCQQSNEAP

YTFGGGTKLEIK,

3) The Biacore 8K assay method was used to rank the affinity of the prokaryotically expressed antibody products and their VH/VL sequences (Table 2), and the anti-human PD-L1 antibody sequence with the highest affinity was used for expression in a eukaryotic system.

TABLE 2

Screening of back mutations in humanized monoclonal antibodies, and ranking of antibodies with the highest affinity

| Ligand | Analyte | ka (1/Ms) | kd (1/s) | KD (M) | Rmax (RU) | Kinetics Chi$^2$ (RU$^2$) | Kinetics model |
|---|---|---|---|---|---|---|---|
| AH02033 | PD-L1/Fc | 4.01E+05 | 2.71E-08 | 6.76E-14 | 66.1 | 4.26E-01 | 1:1 binding |
| AH02030 | | 3.59E+05 | 1.58E-05 | 4.39E-11 | 37.6 | 3.56E-01 | 1:1 binding |
| AH02029 | | 3.39E+05 | 1.93E-05 | 5.68E-11 | 31.6 | 7.31E+00 | 1:1 binding |
| Chimeric antibody | | 3.49E+05 | 2.03E-05 | 5.80E-11 | 69.5 | 1.16E+00 | 1:1 binding |
| AH01946 | | 5.02E+05 | 4.72E-06 | 9.40E-12 | 95.9 | 5.14E-01 | 1:1 binding |
| AH01963 | | 4.74E+05 | 1.63E-05 | 3.44E-11 | 187.8 | 1.40E+00 | 1:1 binding |
| AH01950 | | 5.18E+05 | 1.90E-05 | 3.67E-11 | 88.9 | 5.38E-01 | 1:1 binding |
| AH01964 | | 5.30E+05 | 2.48E-05 | 4.68E-11 | 75.5 | 5.91E-01 | 1:1 binding |
| AH01947 | | 5.33E+05 | 4.38E-05 | 8.22E-11 | 39.3 | 2.81E-01 | 1:1 binding |

10 antibody sequences showing the highest affinity (see, for example, SEQ ID NOs: 9-24):

AH02029-VH
SEQ ID NO: 9
QVQLQESGPGLVKPSQTLSLTCTVTGYSITSGYTWHWIRQHPGKGLEWIG
YIHYSGSTKYNPSLKSRVSISRDTSKNQFSLKLSSVTAADTAVYYCARNS
LFASWGQGTLVTVSS,

AH02030-VH
SEQ ID NO: 10
QVQLQESGPGLVKPSQTLSLTCTVTGYSITSGYTWHWIRQHPGKGLEWIG
YIHYSGSTKYNPSLKSRFTITRDTSKNQFSLKLSSVTAADTAVYYCARNS
LFASWGQGTLVTVSS,

AH02033-VH
SEQ ID NO: 11
QVQLQESGPGLVKPSQTLSLTCTVTGYSITSGYTWHWIRQHPGKGLEWMG
YIHYSGSTKYNPSLKSRFTISRDTSKNQFSLKLSSVTAADTAVYYCARNS
LFASWGQGTLVTVSS,

AH01946-VH
SEQ ID NO: 12
QVQLQESGPGLVKPSQTLSLTCTVSGYSITSGYTWHWIRQHPGKGLEWIG
YIHYSGSTKYNPSLKSRVTISRDTSKNQFSLKLSSMTAADTAVYYCARNS
LFASWGQGTLVTVSS,

AH01947-VH
SEQ ID NO: 13
QVQLQESGPGLVKPSQTLSLTCTVSGYSITSGYTWHWIRQHPGKGLEWIG
YIHYSGSTKYNPSLKSRVTISVDTSKNQFSLKLSSVTAADTAVYYCARNS
LFASWGQGTLVTVSS,

AH01950-VH
SEQ ID NO: 14
QVQLQESGPGLVKPSQTLSLTCTVSGYSITSGYTWHWIRQHPGKGLEWIG
YIHYSGSTKYNPSLKSRVTISRDTSKNQFSLKLSSVTAADTAVYYCARNS
LFASWGQGTLVTVSS,

AH01963-VH
SEQ ID NO: 15
QVQLQESGPGLVKPSQTLSLTCTVSGYSITSGYTWHWIRQHPGKGLEWIG
YIHYSGSTKYNPSLKSRVTISRDTSKNQFSLKLSSVTAADTAVYYCARNS
LFASWGQGTLVTVSS,

AH01964-VH
SEQ ID NO: 16
QVQLQESGPGLVKPSQTLSLTCTVSGYSITSGYTWHWIRQHPGKGLEWIG
YIHYSGSTKYNPSLKSRVTISRDTSKNQFSLKLSSVTAADTAVYYCARNS
LFASWGQGTLVTVSS,

AH02029-VL
SEQ ID NO: 17
DIVLTQSPDSLAVSLGERATINCRASESVDTYGDSFMHWYQQKPGQPPKL
LIYRASNLESGVPDRFSGSGSGTDFTLTISSLQAEDVAVYYCQQSNEAPY
TFGGGTKLEIK,

AH02030-VL
SEQ ID NO: 18
DIVLTQSPDSLAVSLGERATINCRASESVDTYGDSFMHWYQQKPGQPPKL
LIYRASNLESGVPDRFSGSGSRTDFTLTISSLQAEDVAVYYCQQSNEAPY
TFGGGTKLEIK,

AH02033-VL
SEQ ID NO: 19
DIVLTQSPDSLAVSLGERATINCRASESVDTYGDSFMHWFQQKPGQPPKL
LIYRASNLESGIPDRFSGSGSGTDFTLTISSLQAEDVAVYYCQQSNEAPY
TFGGGTKLEIK,

AH01946-VL
SEQ ID NO: 20
DIVLTQSPDSLAVSLGERATINCRASESVDTYGDSFMHWFQQKPGQPPKL
LIYRASNLESGVPDRFSGSGSGTDFTLTISSVQAEDVAVYYCQQSNEAPY
TFGGGTKLEIK,

AH01947-VL
SEQ ID NO: 21
DIVLTQSPDSLAVSLGERATINCRASESVDTYGDSFMHWFQQKPGQPPKL
LIYRASNLESGVPDRFSGSGSGTDFTLTISSLQAEDVAVYYCQQSNEAPY
TFGGGTKLEIK,

AH01950-VL
SEQ ID NO: 22
DIVLTQSPDSLAVSLGERATINCRASESVDTYGDSFMHWFQQKPGQPPKL
LIYRASNLESGVPDRFSGSGSGTDFTLTISSLQAEDVAVYYCQQSNEAPY
TFGGGTKLEIK,

AH01963-VL
SEQ ID NO: 23
DIVLTQSPDSLAVSLGERATINCRASESVDTYGDSFMHWYQQKPGQPPKL
LIYRASNLESGVPDRFSGSGSGTDFTLTISSVQAEDVAVYYCQQSNEAPY
TFGGGTKLEIK,

AH01964-VL
SEQ ID NO: 24
DIVMTQSPDSLAVSLGERATINCRASESVDTYGDSFMHWYQQKPGQPPKL
LIYRASNLESGVPDRFSGSGSGTDFTLTISSLQAEDVAVYYCQQSNEAPY
TFGGGTKL,

Example 2: Recombinant Production of Humanized Antibodies

The VH and VL sequences of the selected antibody were codon optimized, a secretion signal peptide was linked to the 5' end, and then the heavy chain and kappa light chain constant region sequences of human antibody IgG1 were linked. Then the products were respectively cloned into the pTT5 expression vector to prepare a human antibody DNA sequence expressed and secreted in mammalian cells. The plasmid was co-transfected by PEI into HEK293-6E cells cultured in suspension for transient expression. During transfection, the cell density was maintained at $1\times10^6$ cells/mL, and the ratio of PEI:DNA was 3:1. The cells were cultured in an incubator at 37° C. and 5% $CO_2$ with shaking at 105 rpm. After 24 hrs of transfection, 0.5% Trypton N-1 was added. After 5 days, the cell culture supernatant was collected for antibody purification. Before purification, the tubing and protein A column were depyrogenated with 0.2M NaOH. The column was re-equilibrated with a buffer containing 0.05M Tris and 1.5M NaCl (pH 8.0). Subsequently, the harvested cell culture supernatant was diluted 1:1 with 2× the above buffer and sterilized by filtration. The filtered supernatant was incubated with the protein A column at room temperature for 2 hrs. After washing the column with 1× the above buffer, IgG was eluted off with sterile 0.1M sodium citrate (pH 3.5). The eluate was collected and neutralized with one-ninth volume of sterile 1M Tris-HCl (pH9). Under sterile conditions, the product buffer was changed to PBS (pH 7.4) to remove any elution buffer and the sample was concentrated. After concentration, the antibody was quantified by OD280 nm using an extinction coefficient Ec (0.1%) of 1.43.

The purified antibody was analyzed by SDS-PAGE using 10% precast gel (GenScript) in the BioRad electrophoresis system. The gel was stained with Estain 2.0 (GenScript) and the molecular weight and purity were estimated by comparing the stained band with Protein Ladder (GenScript) (Table 3).

injected for about 420 sec at a flow rate of 10 μl/min for coupling, and finally ethanolamine was injected for 420 sec at a flow rate of 10 μl/min to block the surface.

Three pre-cycles were performed with the HBS-EP buffer as a sample to balance the chip to stabilize the baseline. The antibody diluted in HBS-EP buffer was injected for 30 sec at a flow rate of 10 μl/min (where the antibody-antigen binding signal was controlled to about 100RU by adjusting the capture time between 0-5 min), and then the chip was equilibrated with the buffer for 1 min. The low-concentration antigen 2.5 nM PD-L1-HIS was injected at a flow rate of 30 μl/min for 240/300 seconds, to allow the antigen to bind to the antibody, and then the buffer was injected at a flow rate of 30 μl/min for 720/600 seconds for dissociation. 50 mM HCl were injected three times each for 15 s at a flow rate of 100 μl/min for regeneration, to complete one cycle. The antigen concentration was changed (such as 5 nM PD-L1-HIS) to carry out the cycle for measurement at a next gradient concentration until all gradient concentrations (2.5 nM, 5 nM, 10 nM, 20 nM, 40 nM, 80 nM PD-L1-HIS) and the replicate (such as 10 nM PD-L1-HIS) were tested.

The experimental data was double subtracted (minus the background values of the control channel and zero concentration), and fitted to the "1:1 binding" model in the Biacore 8K evaluation software. Biacore 8K was used to determine the affinity of the antibody to the PD-L1-HIS recombinant protein.

TABLE 3

Recombinant production of humanized antibodies

| Sample No. | Clone No. | Transfection system | Antibody concentration (mg/ml) | Antibody volume (ml) | Total antibody amount (mg) | Antibody purity (%) |
|---|---|---|---|---|---|---|
| mPD-L1Ab-CBM | AH01946 | 50 ml | 0.436 | 3.8 | 1.66 | 90% |
| mPD-L1Ab-CBM | AH01947 | 50 ml | 0.071 | 3.8 | 0.27 | 97% |
| mPD-L1Ab-CBM | AH01950 | 50 ml | 0.109 | 3.8 | 0.41 | 95% |
| mPD-L1Ab-CBM | AH01963 | 50 ml | 0.488 | 3.8 | 1.85 | 90% |
| mPD-L1Ab-CBM | AH01964 | 50 ml | 0.045 | 3.8 | 0.17 | 98% |
| mPD-L1Ab-5BM | AH02029 | 50 ml | 0.117 | 3.7 | 0.43 | 91% |
| mPD-L1Ab-5BM | AH02030 | 50 ml | 0.442 | 0.2 | 0.09 | 99% |
| mPD-L1Ab-5BM | AH02033 | 50 ml | 0.018 | 3.8 | 0.07 | 98% |
| mPD-L1Ab-Chim | Chimeric antibody | 50 ml | 0.404 | 0.8 | 0.32 | 94% |

Example 3: Affinity Determination of Humanized Monoclonal Antibody

The chip surface was equilibrated with HBS-EP buffer at a flow rate of 10 μl/min for 5 min, and then a 1:1 mixture of "NHS+EDC" was injected at a flow rate of 10 μl/min for 420 sec to activate the chip. The capture antibody (goat anti-murine IgG) diluted in 10 mM sodium acetate buffer was As shown in FIG. 1 and Table 4, the affinity to PD-L1-HIS of humanized monoclonal antibodies (AH01946, AH01947, AH01950, AH01963, AH01964, AH02029, AH02030, and AH02033) specific to human PD-L1 is measured by Biacore to reach the nM level. These results indicate that the antibodies screened by the present invention have very high affinity.

TABLE 4

Affinity determination of humanized anti-human PD-L1-HIS monoclonal antibody

| Ligand | Analyte | $k_a$ (1/Ms) | $k_a$ (1/s) | $K_D$ (M) | Rmax (RU) | Chi$^2$ (RU$^2$) |
|---|---|---|---|---|---|---|
| AH01950 | | 1.85E+05 | 1.52E−04 | 8.20E−10 | 49.8 | 4.93E−02 |
| AH01946 | | 1.86E+05 | 1.55E−04 | 8.35E−10 | 42.8 | 3.51E−02 |
| AH02033 | | 1.84E+05 | 1.66E−04 | 9.03E−10 | 46.4 | 4.04E−02 |
| AH02030 | | 1.85E+05 | 2.16E−04 | 1.17E−09 | 24.1 | 2.76E−02 |
| Chimeric antibody | PD-L1/His | 1.72E+05 | 2.19E−04 | 1.27E−09 | 26.9 | 2.29E−02 |
| AH01963 | | 2.16E+05 | 2.74E−04 | 1.27E−09 | 25.9 | 1.78E−02 |
| AH02029 | | 2.13E+05 | 3.34E−04 | 1.57E−09 | 43.4 | 4.15E−02 |
| AH01964 | | 2.10E+05 | 3.70E−04 | 1.76E−09 | 45.9 | 4.38E−02 |
| AH01947 | | 2.30E+05 | 7.14E−04 | 3.11E−09 | 33.6 | 2.60E−02 |

Example 4: Verification of Cell Activity Function in the Presence of Humanized Anti-Human PD-L1 Monoclonal Antibody In the mixed lymphocyte reaction, a kit (Miltenyl Biotec) was used to separate the monocytes and CD4+ T cells from human peripheral blood mononuclear cells, and the monocytes were induced into dendritic cells. In the experiment, each well contained $10^4$ allogeneic dendritic cells, $5×10^4$ CD4+ T cells, and a different concentration of antibody sample working solution, and the final working volume was 200 μl. The well without antibody was used as a background control, irrelevant human IgG1 antibody was used as a negative control, and anti-PD-L1 antibody was used as a positive control. After 72 hrs of incubation at 37° C. and 5% $CO_2$, the supernatant was taken from each well to detect the IL-2 content (Cisbio's HTRF detection kit).

As shown in FIG. 2, after adding different gradient dilutions of anti-PD-L1 antibody clone to the co-culture system, the anti-PD-L1 antibody clone binds to PD-L1 expressed the target cells without directly affecting the PD-1/PD-L1 interaction, to activate CD4+ T cells to release the cytokine IL-2. Compared with Tecentriq, these tested clones all have comparable or higher functions (Table 5).

TABLE 5

Cellular activation response of humanized anti-human PD-L1 monoclonal cells

| | Best-fit values | | | | | |
|---|---|---|---|---|---|---|
| Sample | Bottom | Top | LogEC$_{50}$ | Hill Slope | Span | EC$_{50}$ (μg/ml) |
| Tecentriq | 1199 | 1870 | −1.517 | 1.854 | 670.6 | 0.03038 |
| IgG1 | 619.7 | 719 | ~0.2785 | ~11.17 | 99.28 | ~1.899 |
| AH01946 | 1168 | 2034 | −1.53 | 1.869 | 866.1 | 0.02953 |
| AH01950 | 1142 | 2091 | −1.507 | 0.8789 | 949.8 | 0.03111 |
| AH01963 | 1420 | 2351 | −1.391 | 1.634 | 930.4 | 0.04062 |
| AH02029 | 1353 | 2371 | −1.534 | 0.676 | 1018 | 0.02926 |

Example 5: Evaluation of the Druggability of Humanized Anti-Human PD-L1 Monoclonal Antibody AH01946, AH01950, AH01963, AH02029 and chimeric antibody were expressed in a 200 ml system to obtain a purified antibody sample of more than 5 mg and having an endotoxin content controlled at the level of 3 EU/mg for subsequent experiments.

1. Thermal Stability Test 1.1. Differential Scanning Fluorimetry to Detect the Denaturation Temperature Tm of the Sample

TABLE 6

Detection of Tm of humanized anti-human PD-L1 monoclonal antibody

| Sample | Concentration (mg/ml) | Tm Onset | Tagg | Tm |
|---|---|---|---|---|
| AH01946 | 0.67 | 50.4° C. | 76.2° C. | 70.2° C. |
| AH01950 | 0.67 | 52.1° C. | 54.0° C. | 70.2° C. |
| AH01963 | 0.85 | 51.4° C. | 76.8° C. | 70.0° C. |
| AH02029 | 0.8 | 61.2° C. | 77.1° C. | 77.9° C. |
| Chimeric antibody | 2 | 67.4° C. | 82.8° C. | 70.7° C. |

The test results show (Table 6) that the Tm of AH01946, AH01950, AH01963, and AH02029 are all above 70° C., and the Tm of AH02029 is 77.9° C.

1.2. Experimental Settings for Thermal Stability Test

A. The Durability Test was Conducted with an Antibody Sample Concentration of >5 mg/ml.

The antibody samples were treated separately at 40° C., and then centrifuged to remove the pellet. Then the amount of remaining antibody was evaluated by ELISA. (test after treatment at 40° C. for 7 days (D7) and 14 days (D14) separately; for each test, the untreated sample (D0) stored at −80° C. is used as a control) (FIG. 3)

B. The High-Temperature Test was Conducted with a Sample Concentration of >5 mg/ml.

The antibody samples were treated for 20 min at various temperature gradients respectively, and then centrifuged to remove the pellet. Then the amount of remaining antibody was evaluated by ELISA. (The temperature gradient includes: room temperature, 30° C., 40° C., 50° C., 60° C., 70° C., −80° C.) (FIG. 4)

ELISA results show that AH01946, AH01950, AH01963, and AH02029 all have good thermal stability. The antibody after treatment has a high degree of agreement with respect to the curve compared with the control, and the recognition ability of human PD-L1 protein is not affected. Especially for AH01946 and AH02029 in the durability test, and AH01946 and AH01963 in the high-temperature test, the samples treated under different conditions show a very high agreement with the control D0 or ELISA curve a at −80° C.

C. The Treated Sample in the Durability Test was Subjected to SEC-HPLC and Nr-SDS Test.

Figure 5A:
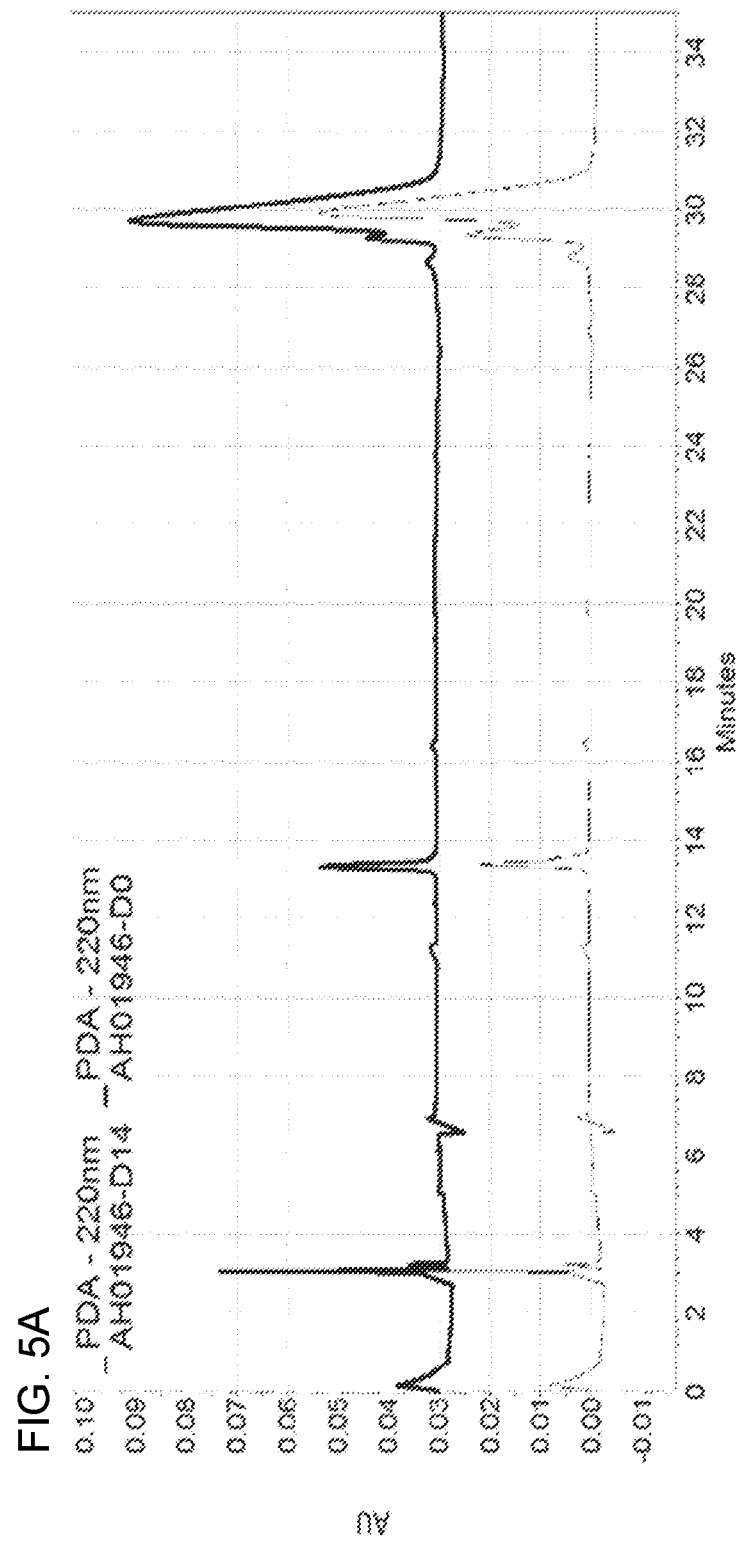
Figure 5C:
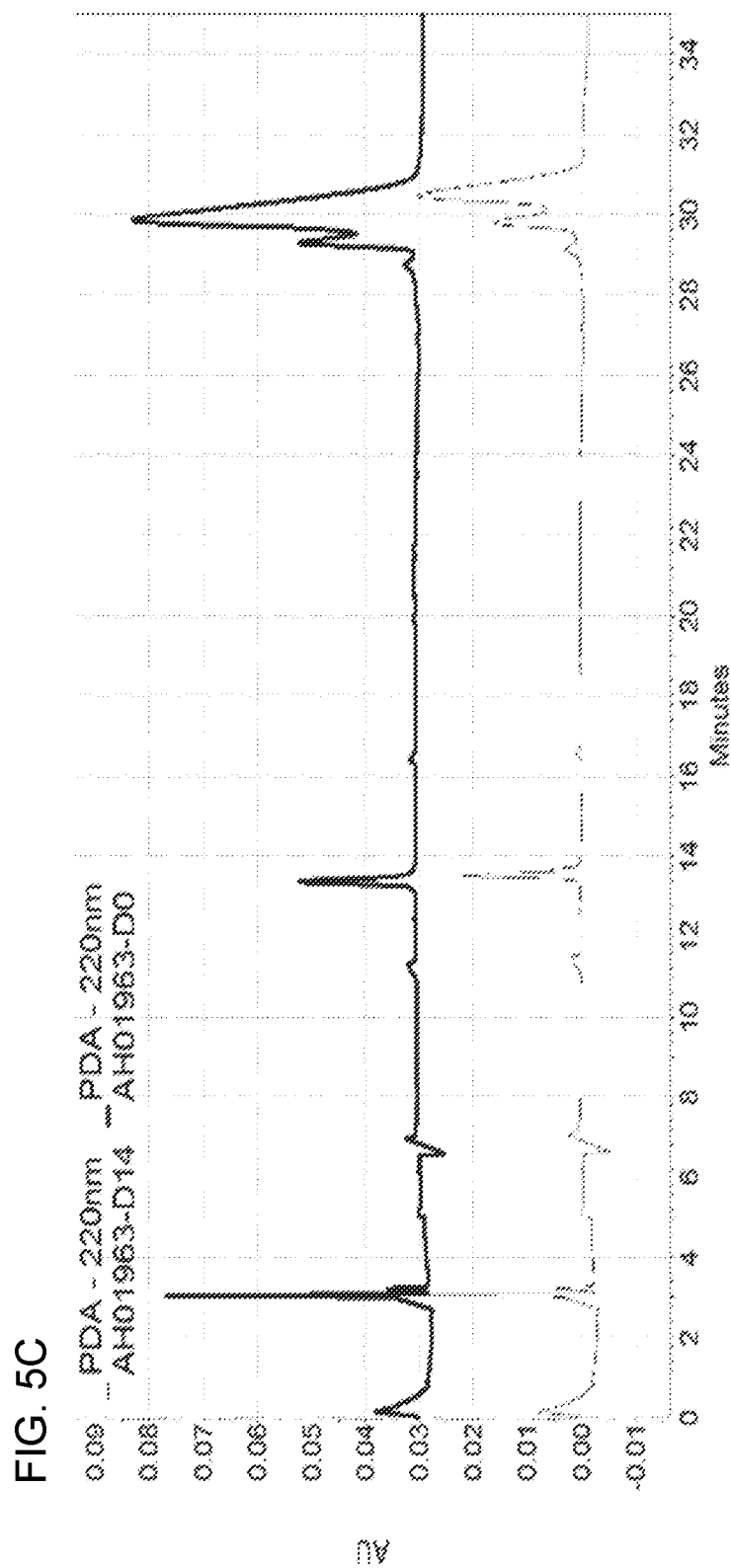
Figure 5D:
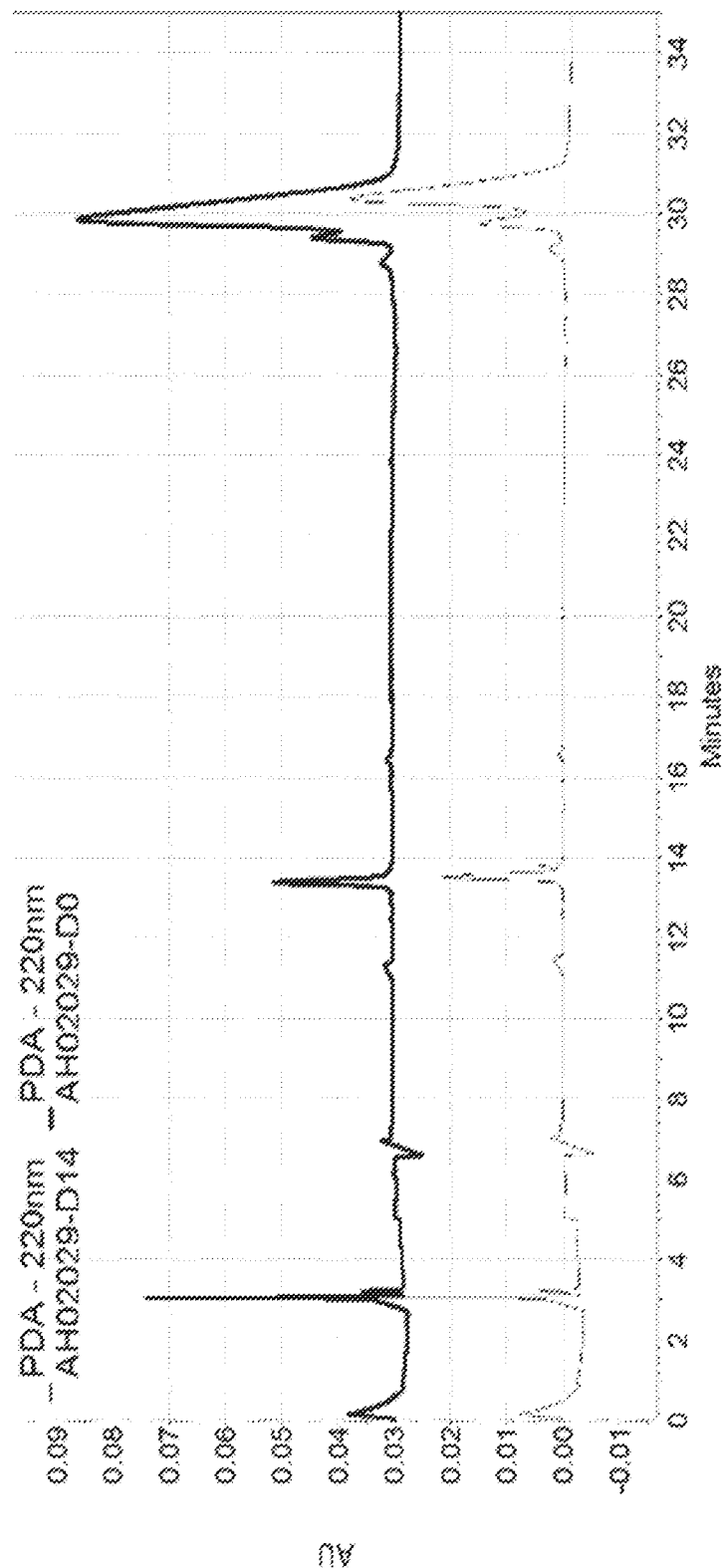
Figure 6A:
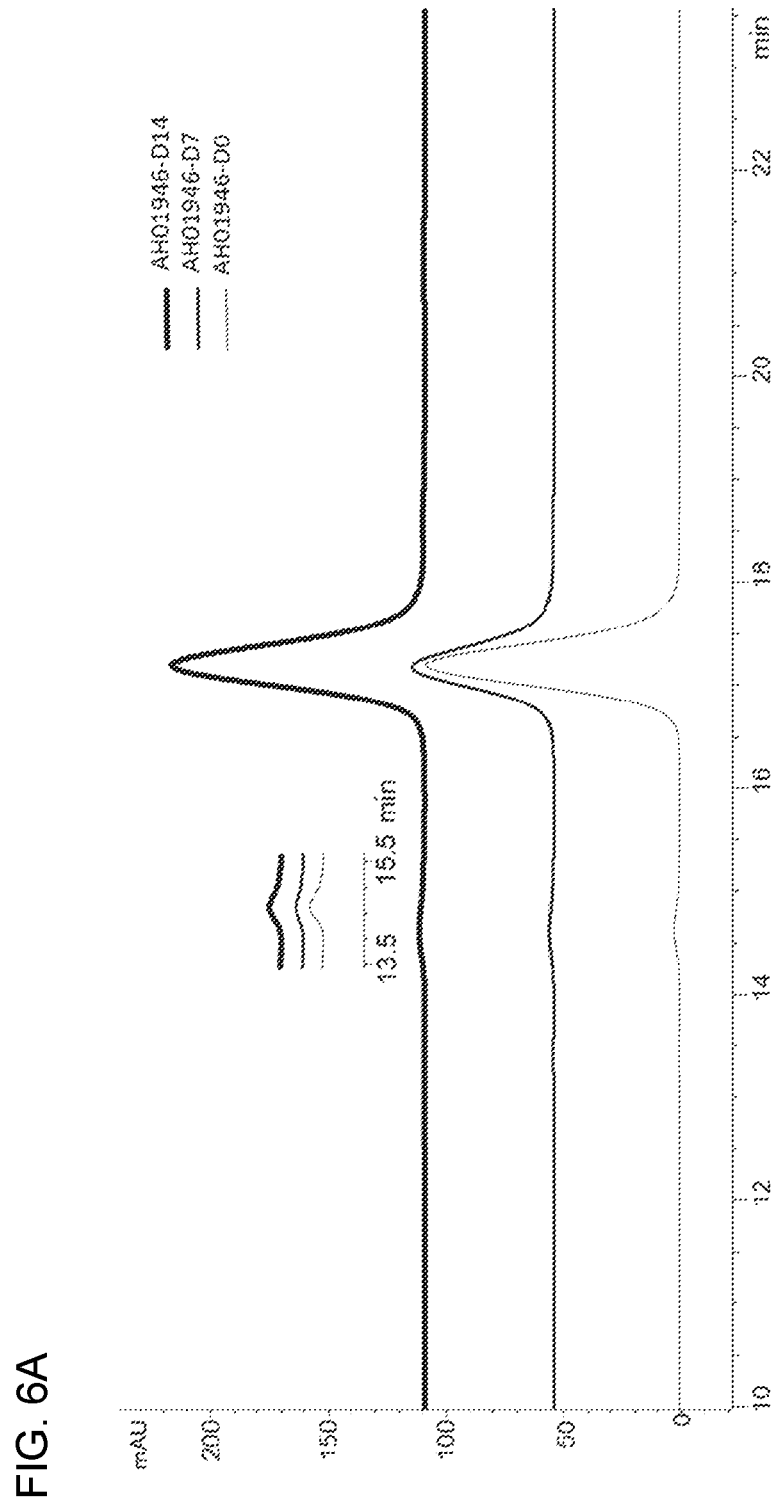
FIGS. 6A-6D show the thermal stability analysis of purified monoclonal antibodies, specifically thermal stability analysis by SEC-HPLC of humanized anti-human PD-L1 monoclonal antibodies (treated at 40° C. for 1-2 weeks), including AH01946-0/7/14 days (FIG. 6A), AH01950-0/7/14 days (FIG. 6B), AH01963-0/7/14 days (FIG. 6C), and AH02029-0/7/14 days (FIG. 6D)
Figure 6B:
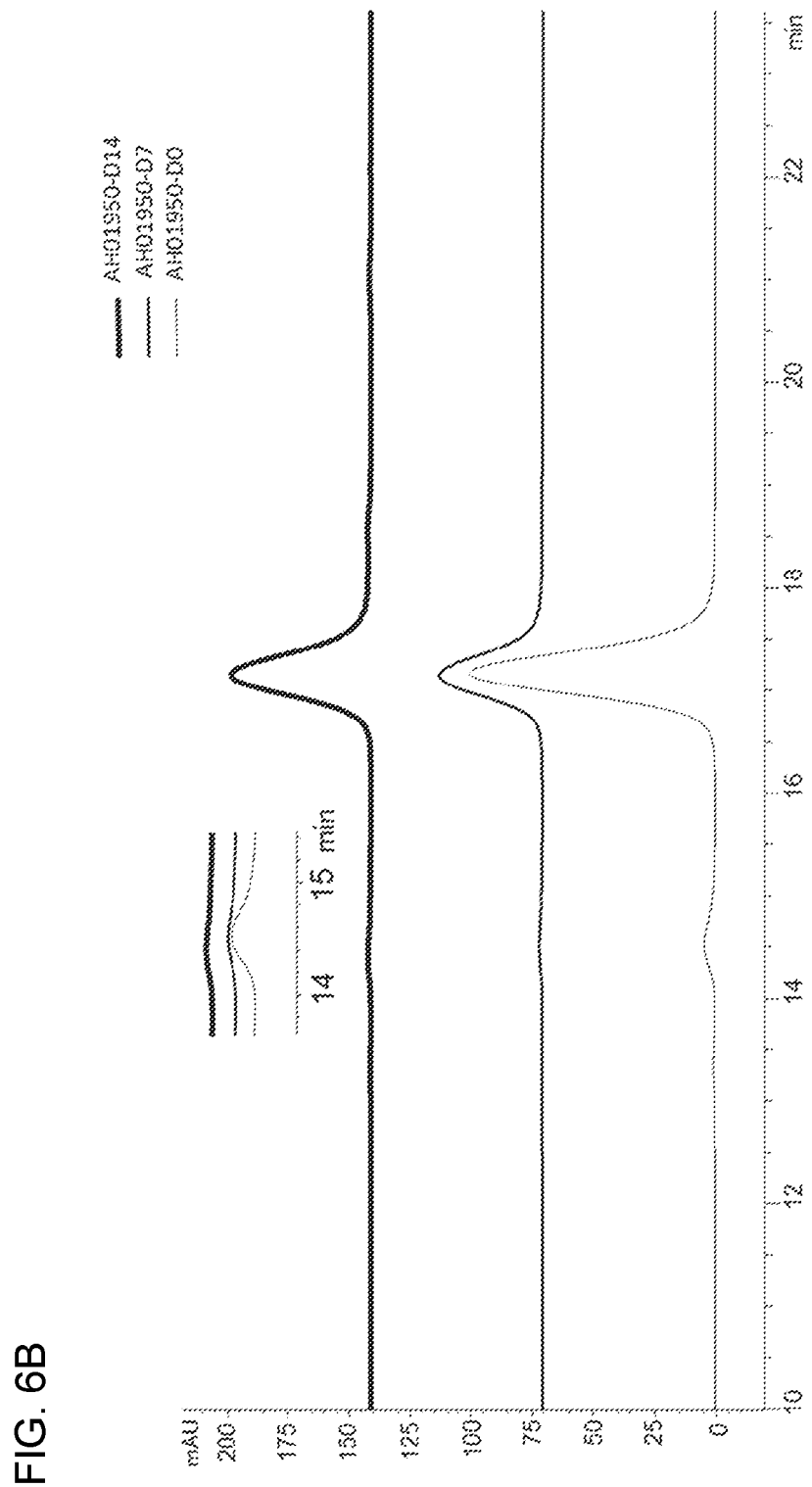
Figure 6C:
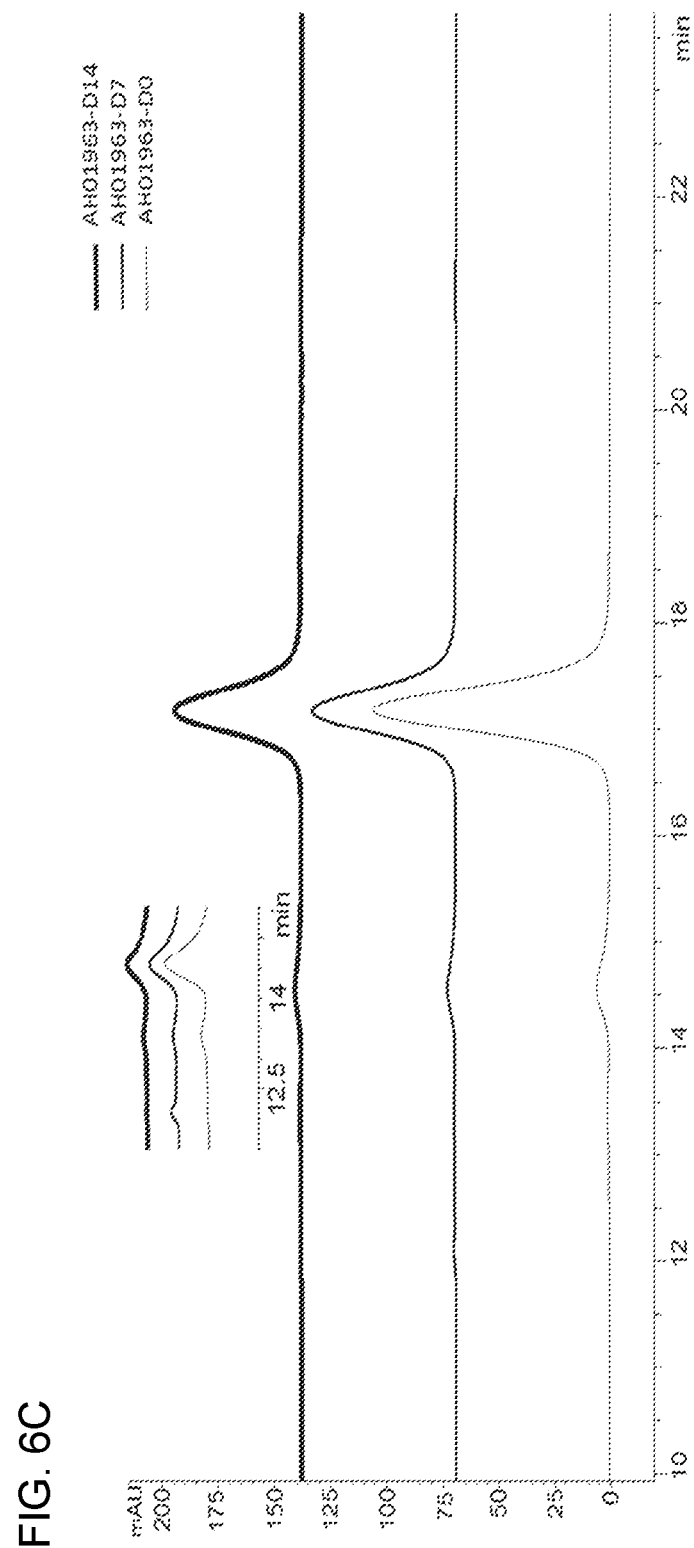
Figure 6D:
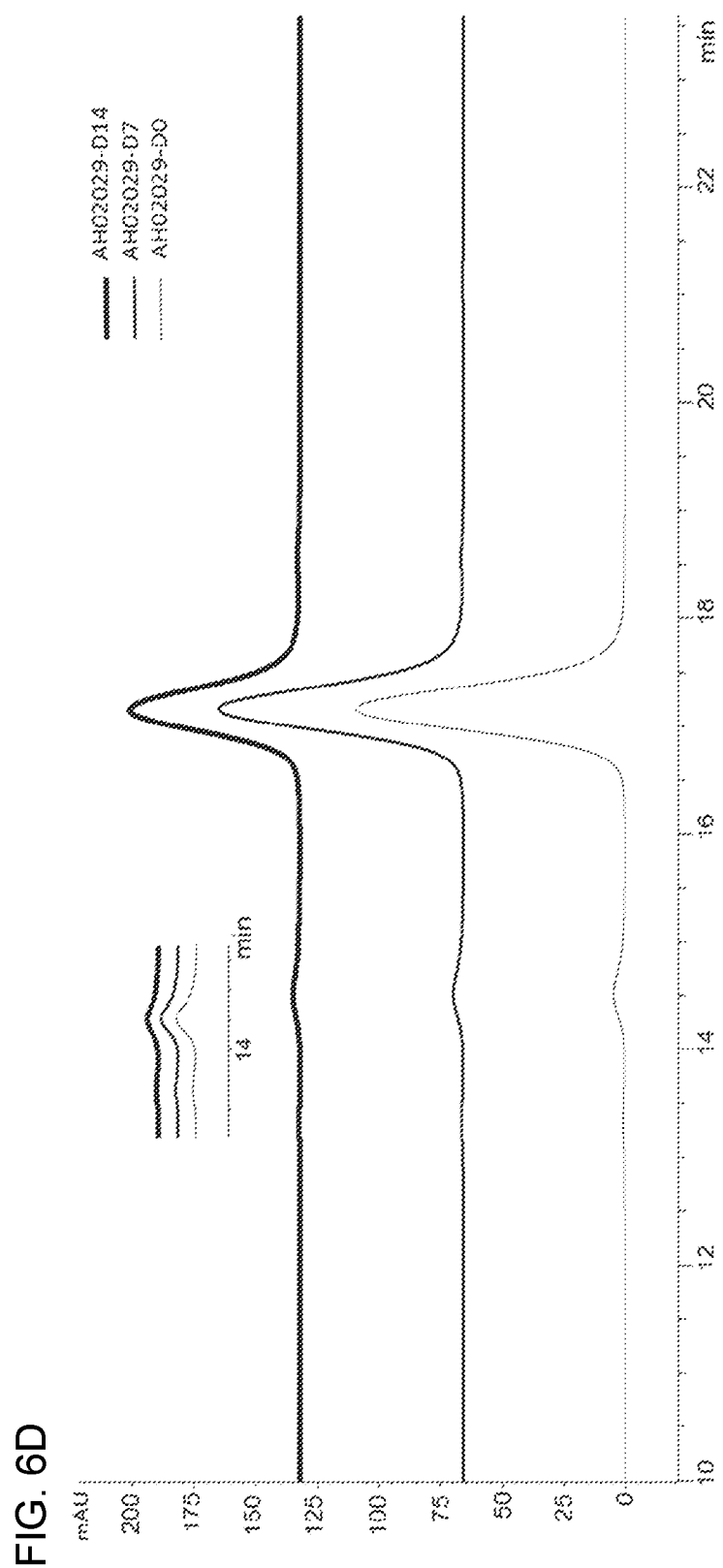
Figure 7A:
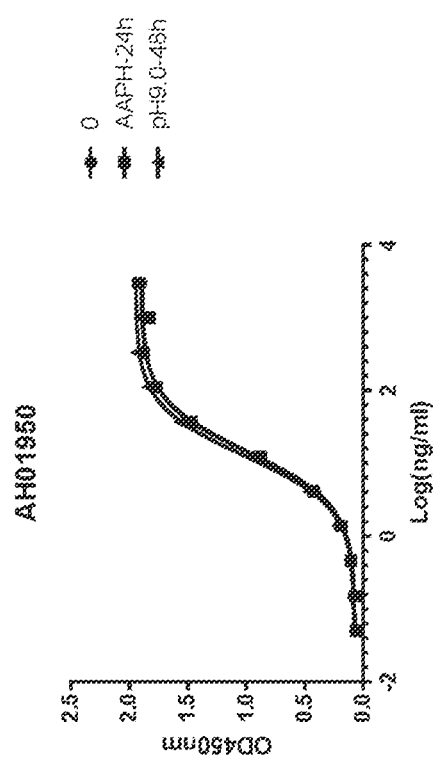
FIGS. 7A-7D show the detection and analysis of the druggability of purified monoclonal antibodies, specifically ELISA analysis of humanized anti-human PD-L1 monoclonal antibodies after oxidative stress/deamidation stress test, including AH01946 (FIG. 7A), AH01950 (FIG. 7B), AH01963 (FIG. 7A), AH01950 (FIG. 7B), AH01963 (FIG. 7A) 7C), and AH02029 (FIG. 7D)
Figure 7B:
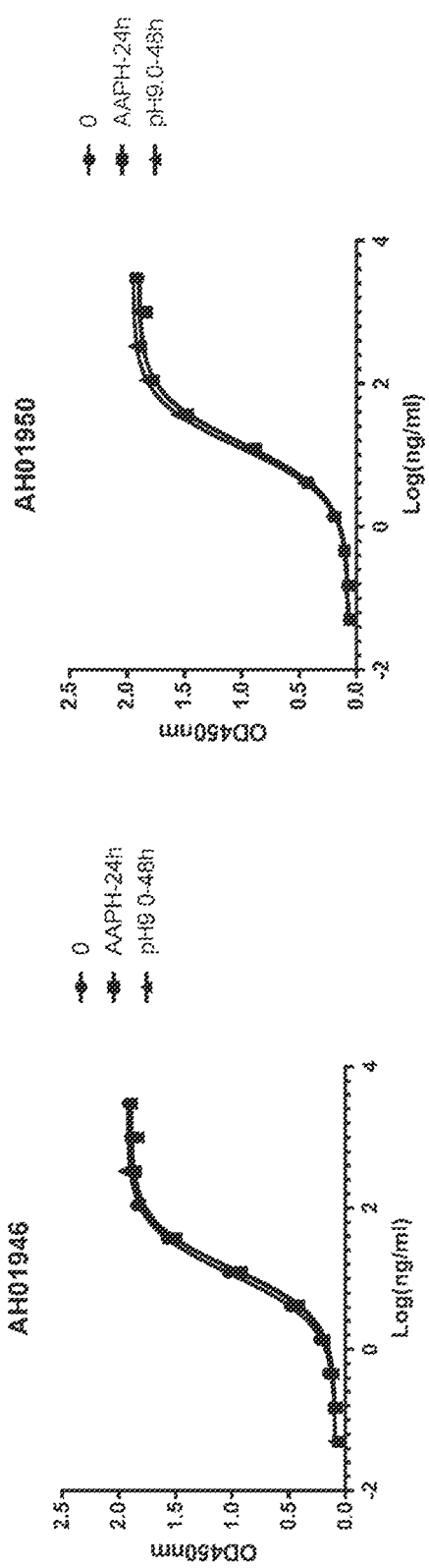
Figure 7C:
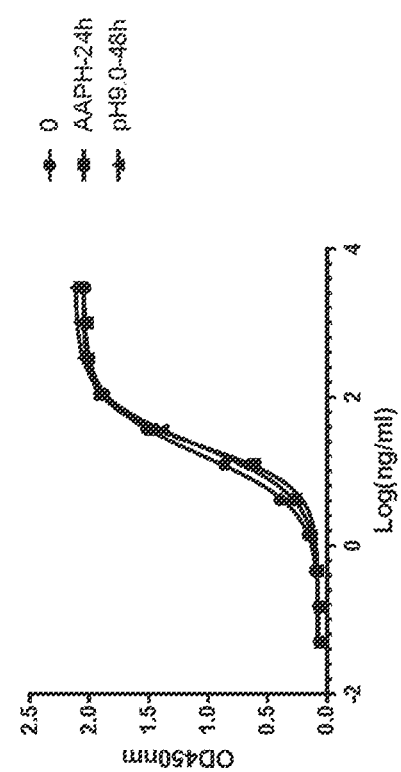
Figure 7D:
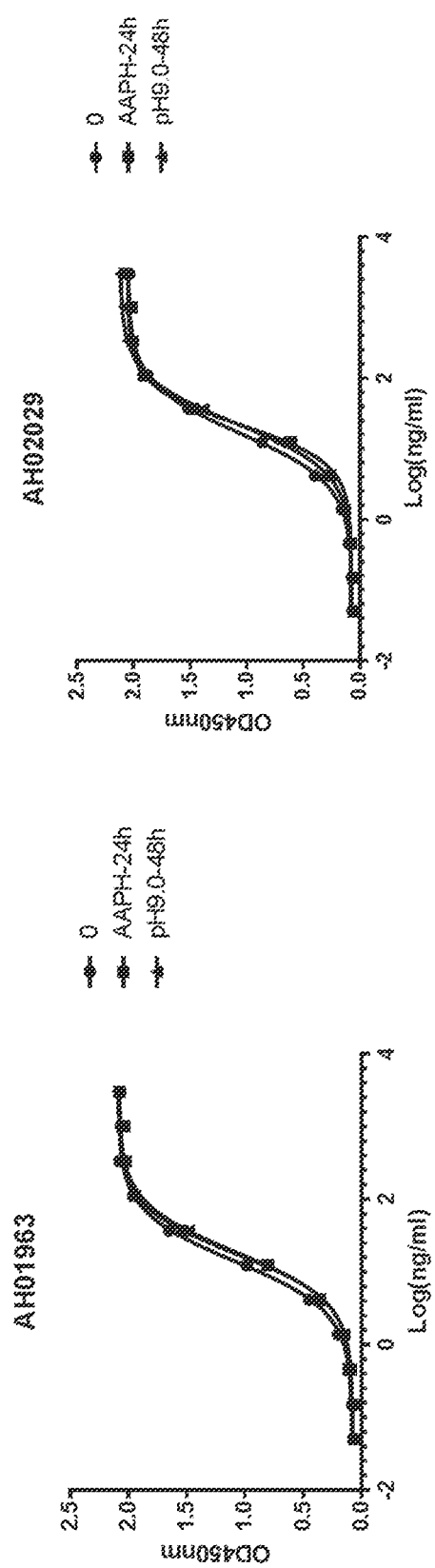
Figure 8A:
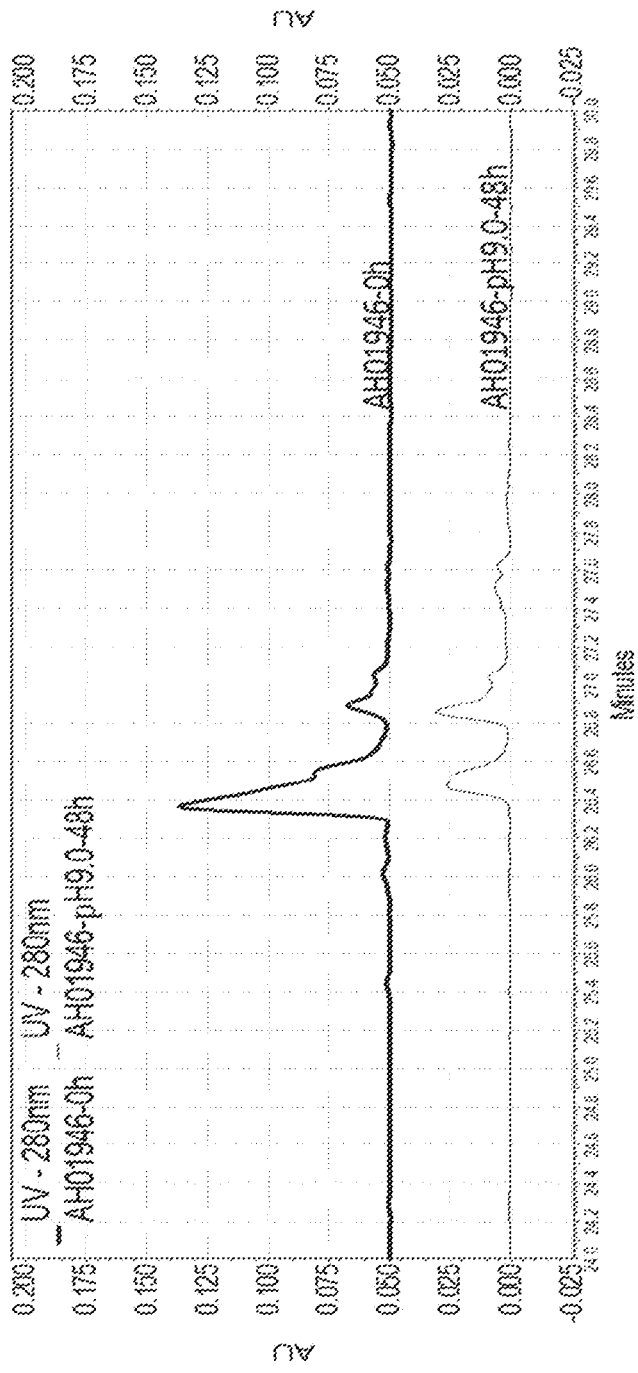
FIGS. 8A-8D show the detection and analysis of the druggability of purified monoclonal antibodies, specifically c-IEF analysis of humanized anti-human PD-L1 monoclonal antibodies after deamidation stress test, including AH01946 (FIG. 8A), AH01950 (FIG. 8B), AH01963 (FIG. 8C), and AH02029 (FIG. 8D)
Figure 8B:
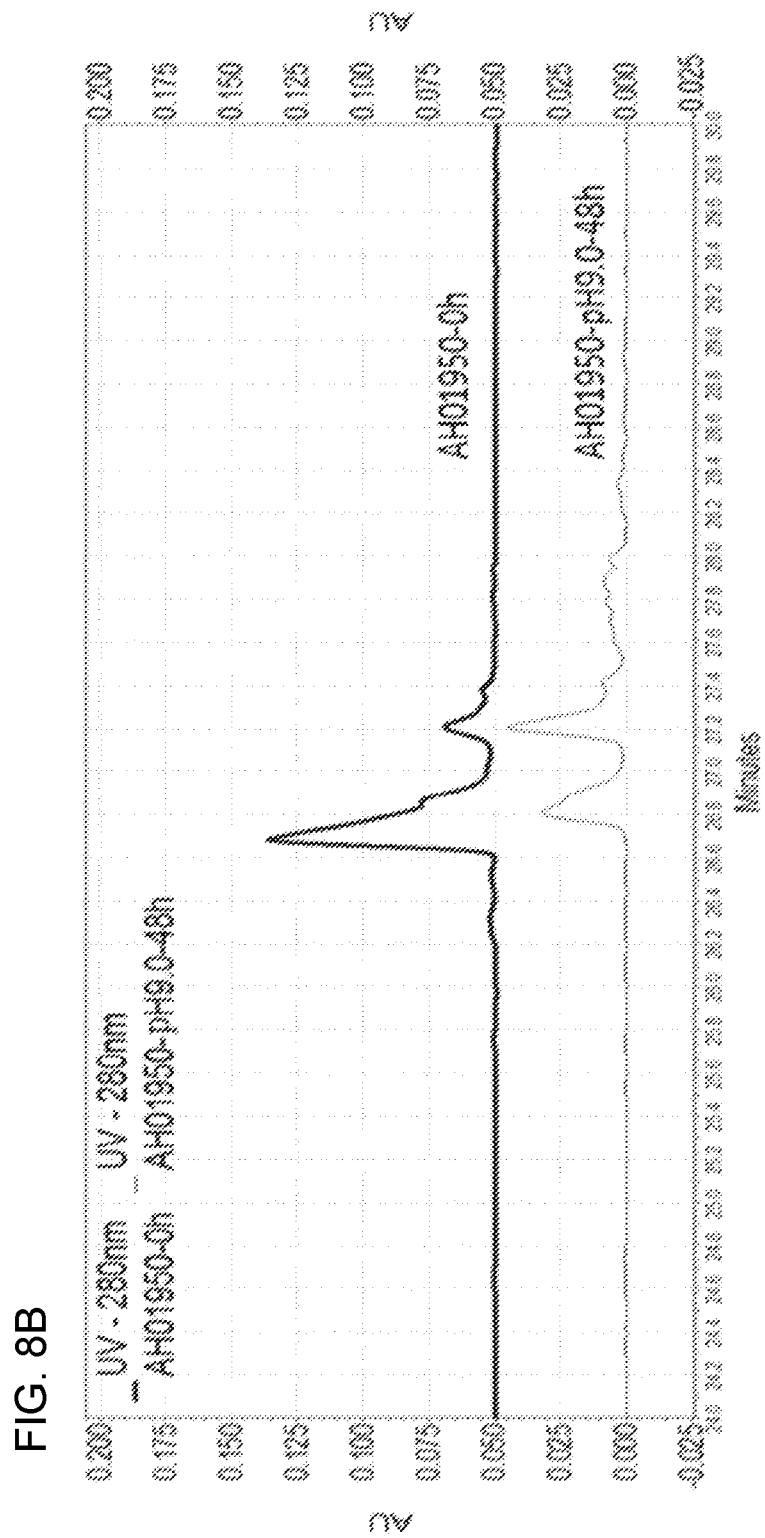
Figure 8C:
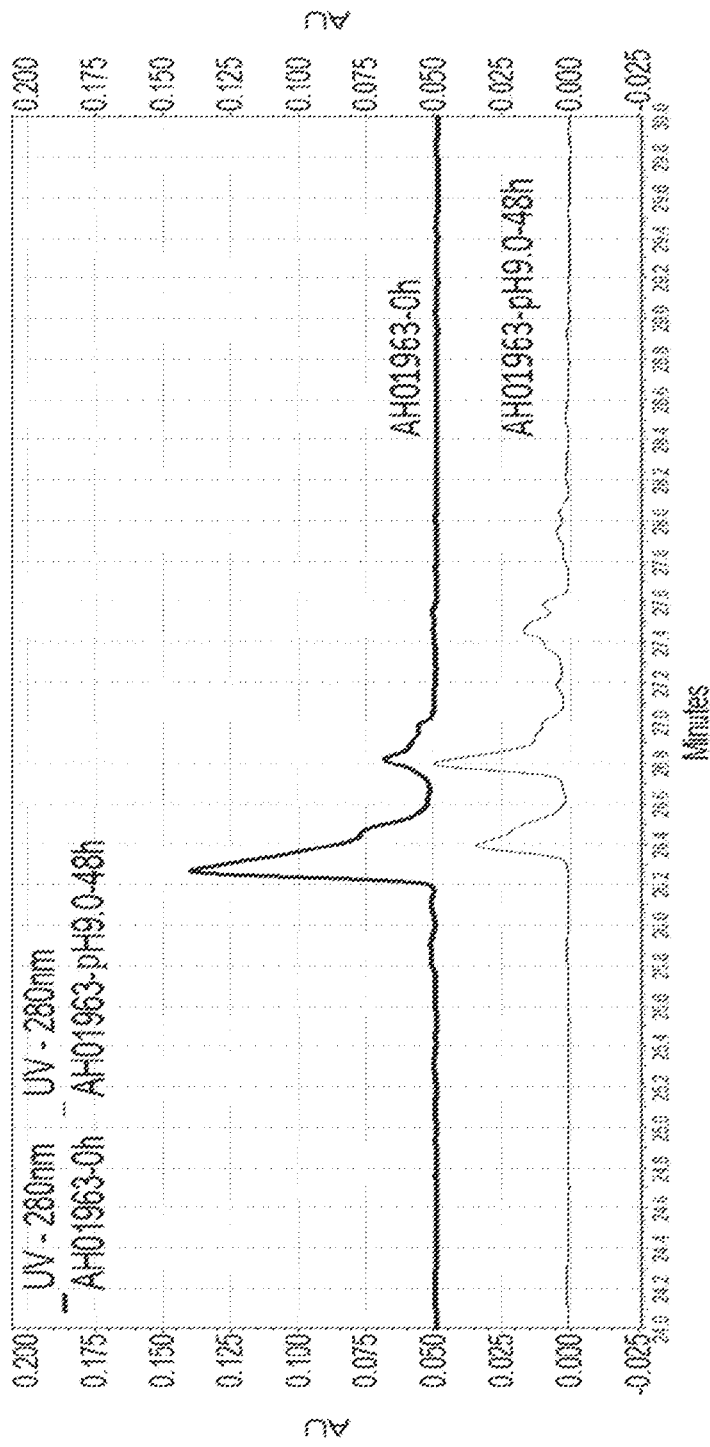
Figure 8D:
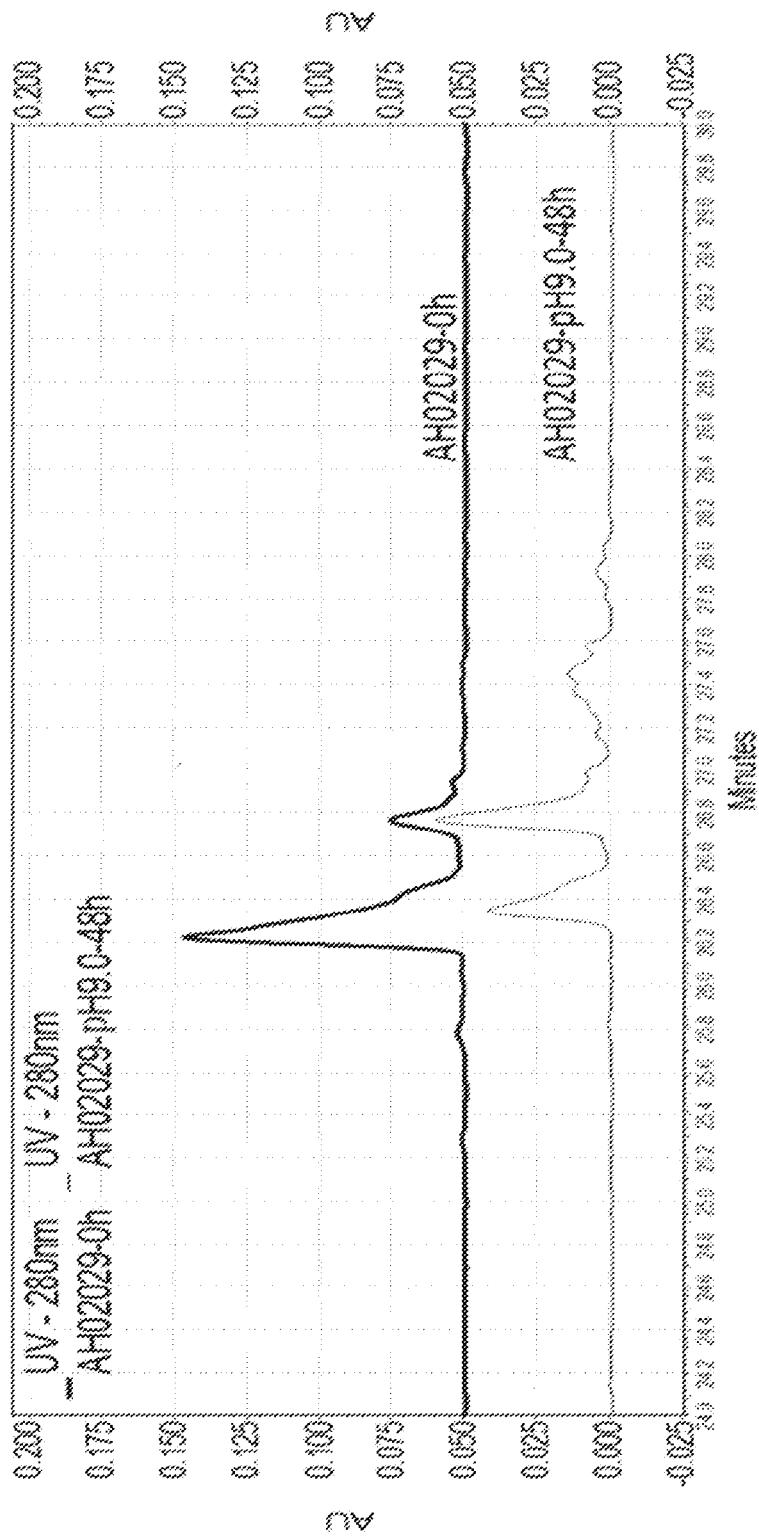

The results are shown in Table 7 and FIG. 5. The purity test by nr-SDS of each antibody sample after heat treatment does not show a large amount of fragments, and the main antibody peak of the sample after the AH01946 and AH02029 antibodies are treated is more than 77%. Table 8 and FIG. 6 show that the purity test by SEC-HPLC of antibody samples does not find that the heat treatment results in large antibody aggregation.

TABLE 7

Purity detection by nr-SDS of humanized anti-human PD-L1 monoclonal antibody before and after heat treatment

| Sample name | Before antibody peak (%) | Antibody peak (%) |
| --- | --- | --- |
| AH01946-D0 | 9.68 | 90.32 |
| AH01946-D14 | 22.54 | 77.46 |
| AH01950-D0 | 11.00 | 89.00 |
| AH01950-D14 | 33.78 | 66.22 |
| AH01963-D0 | 16.54 | 83.46 |
| AH01963-D14 | 30.50 | 69.50 |
| AH02029-D0 | 11.10 | 88.89 |
| AH02029-D14 | 21.93 | 78.06 |

TABLE 8

Purity detection by SEC-HPLC of humanized anti-human PD-L1 monoclonal antibody before and after heat treatment

| Sample name | Main peak (%) | Aggregate (%) | Degradation (%) |
| --- | --- | --- | --- |
| AH01946-D0 | 96.44 | 3.31 | 0.26 |
| AH01946-D7 | 96.03 | 3.35 | 0.62 |
| AH01946-D14 | 95.82 | 3.15 | 1.03 |
| AH01950-D0 | 94.00 | 6.00 | 0.00 |
| AH01950-D7 | 94.06 | 4.98 | 0.96 |
| AH01950-D14 | 93.08 | 3.24 | 3.68 |
| AH01963-D0 | 92.22 | 7.78 | 0.00 |
| AH01963-D7 | 90.62 | 8.44 | 0.95 |
| AH01963-D14 | 91.54 | 7.08 | 1.38 |
| AH02029-D0 | 94.05 | 5.70 | 0.25 |
| AH02029-D7 | 93.98 | 4.95 | 1.07 |
| AH02029-D14 | 93.61 | 4.90 | 1.49 |

2. Druggability Test

Based on the analysis of the amino acid sequence of the antibody and the prediction of hot sites for post-translational modification, the CDR region of the anti-human PD-L1 monoclonal antibody is predicted to have three hot sites for post-translational modification, that is, N99 (VH, asparagine deamidation), W35 (VH, oxidative), and M37 (VL, oxidative) (Table 1). The humanized anti-human PD-L1 monoclonal antibodies were respectively subjected to the following stress tests:

A. Oxidative stress test: The antibody molecules were transferred to a 20 mM ammonium acetate solution (pH 5.0), added with AAPH (2,2'-azobis(2-amidinopropane)) (50:1) and treated at 40° C. for 24 hrs in the dark.

B. Deamidation stress test: The antibody molecules were placed in a PBS solution (pH9) at 40° C. for 48 hrs.

The effect of oxidative modification/deamidation modification on the antigen recognizing ability of the antibody molecules was determined.

The results show (Table 9-10) that the coverage rate of MS detection reaches about 95%, and reliable results are obtained. In the four groups of samples of AH01946, AH01950, AH01963 and AH02029, no oxidative modifications are detected at the W35 (VH) and M37 (VL) sites before and after the oxidative stress test. In the deamidation stress test of the four groups of samples of AH01946, AH01950, AH01963 and AH02029, a higher proportion of N at position 99 was detected to have deamidation modification in the sample of the control group (0 h); and in the test groups (pH9-48 h), only deamidated peptides are detected at the N99 site, and no modified peptides are detected. It proves that there is a high possibility of deamidation modification at the N99 site.

TABLE 9

Druggability detection and analysis: MS detection of humanized anti-human PD-L1 monoclonal antibody after oxidative stress test

| Sample name | Peptide fragment | Sequence | Modification | Modification percentage | XIC area |
| --- | --- | --- | --- | --- | --- |
| AH01946-0h | C76-77 | SCSVMHEALHNHY (SEQ ID NO: 25) | Carbamidomethylation @2(423) | | 4.54E+06 |
| AH01946-AAPH-24h | C76-77 | SCSVMHEALHNHY (SEQ ID NO: 25) | Carbamidomethylation @2(423), oxidative @5(426) | 42.06% | 3.42E+06 |
| AH01946-AAPH-24h | C76-77 | SCSVMHEALHNHY (SEQ ID NO: 25) | Carbamidomethylation @2(423) | 57.96% | 4.71E+06 |
| AH01946-0h | C21-23 | SLKLSSMTAADTAVY (SEQ ID NO: 26) | | | 5.75E+06 |

TABLE 9-continued

Druggability detection and analysis: MS detection of humanized anti-human PD-L1 monoclonal antibody after oxidative stress test

| Sample name | Peptide fragment | Sequence | Modification | Modification percentage | XIC area |
|---|---|---|---|---|---|
| AH01946-AAPH-24h | C21-23 | SLKLSSMTAADTAVY (SEQ ID NO: 26) | Oxidative @7(86) | 4.64% | 1.15E+06 |
| AH01946-AAPH-24h | C21-23 | SLKLSSMTAADTAVY (SEQ ID NO: 26) | Oxidative @7(86) | 95.36% | 2.33E+07 |
| AH01946-0h | C54-57 | TVLHQDWLNGKEY (SEQ ID NO: 27) | | | 1.81E+07 |
| AH01946-AAPH-24h | C54-57 | TVLHQDWLNGKEY (SEQ ID NO: 27) | Oxiation @7(311) | 10.58% | 1.74E+05 |
| AH01946-AAPH-24h | C54-57 | TVLHQDWLNGKEY (SEQ ID NO: 27) | Oxiation @7(311) | 89.42% | 1.47E+06 |
| AH01950-0h | C76-77 | SCSVMHEALHNHY (SEQ ID NO: 25) | Carbamidomethylation @2(423) | | 7.49E+06 |
| AH01950-AAPH-24h | C76-77 | SCSVMHEALHNHY (SEQ ID NO: 25) | Carbamidomethylation @2(423), oxidation @5(426) | 56.33% | 2.39E+06 |
| AH01950-AAPH-24h | C76-77 | SCSVMHEALHNHY (SEQ ID NO: 25) | Carbamidomethylation @2(423) | 43.675 | 1.85E+06 |
| AH01963-0h | C46-47 | FPPKPKDTLMI (SEQ ID NO: 28) | | | 2.22E+06 |
| AH01963-AAPH-24h | C47-48 | MISRTPEVTCVVVDVS HEDPEVKF (SEQ ID NO: 29) | Oxidative @1(250), Carbamidomethylation @10(259) | 48.23% | 1.24E+06 |
| AH01963-AAPH-24h | C47-48 | MISRTPEVTCVVVDVS HEDPEVKF (SEQ ID NO: 29) | Carbamidomethylation @10(259) | 51.77% | 1.33E+06 |
| AH01963-0h | C53-57 | RVVSVLTVLHQDWLN GKEY (SEQ ID NO: 30) | | | 6.25E+05 |
| AH01963-AAPH-24h | C53-57 | RVVSVLTVLHQDWLN GKEY (SEQ ID NO: 30) | Oxidative @13(311) | 2.60% | 1.64E+04 |
| AH01963-AAPH-24h | C53-57 | RVVSVLTVLHQDWLN GKEY (SEQ ID NO: 30) | | 97.40% | 6.14E+05 |
| AH01963-0h | C76-77 | SCSVMHEALHNHY (SEQ ID NO: 25) | Carbamidomethylation @2(423) | | 6.08E+06 |
| AH01963-AAPH-24h | C76-77 | SCSVMHEALHNHY (SEQ ID NO: 25) | Carbamidomethylation @2(423), oxidative @5(426) | 39.06% | 2.20E+06 |
| AH01963-AAPH-24h | C76-77 | SCSVMHEALHNHY (SEQ ID NO: 25) | Carbamidomethylation @2(423) | 60.94% | 3.42E+06 |
| AH02029-0h | C76-77 | SCSVMHEALHNHY (SEQ ID NO: 25) | Carbamidomethylation @2(423) | | 3.88E+06 |
| AH02029-AAPH-24h | C76-77 | SCSVMHEALHNHY (SEQ ID NO: 25) | Carbamidomethylation @2(423), oxidative @5(426) | 62.38% | 3.74E+06 |
| AH02029-AAPH-24h | C76-77 | SCSVMHEALHNHY (SEQ ID NO: 25) | Carbamidomethylation @2(423) | 37.625 | 2.26E+06 |

TABLE 10

Druggability detection and analysis: MS detection of humanized anti-human PD-L1 monoclonal antibody after deamidation stress test

| Sample name | Peptide fragment | Sequence | Modification | Modification percentage | XIC area |
|---|---|---|---|---|---|
| AH01946-0h | T32-35 | YCARNSLF (SEQ ID NO: 31) | Carbamidomethylation @2(96) | 42.40% | 1.99E+05 |
| | T32-35 | YCARNSLF (SEQ ID NO: 31) | Carbamidomethylation @2(96), deamidization @5(99) | 57.60% | 2.69E+05 |
| AH01946-pH9.0-48h | T33-35 | CARNSLF (SEQ ID NO: 32) | Carbamidomethylation @1(96), deamidization @4(99) | 100.00% | 4.59E+05 |
| | T33-36 | CARNSLFASW (SEQ ID NO: 33) | Carbamidomethylation @1(96), deamidization @4(99) | | 6.48E+04 |
| | T32-35 | YCARNSLF (SEQ ID NO: 31) | Carbamidomethylation @2(96), deamidization @5(99) | | 7.38E+05 |
| AH01950-0h | T95-97 | NQVSLTCLVK (SEQ ID NO: 34) | Carbamidomethylation @7(365) | 99.40% | 2.09E+07 |
| | T95-97 | NQVSLTCLVK (SEQ ID NO: 34) | Deamidization @1(359), carbamidomethylation @7(365) | 0.60% | 1.30E+05 |
| | T32-35 | YCARNSLF (SEQ ID NO: 31) | Carbamidomethylation @2(96) | 31.20% | 1.05E+05 |

TABLE 10-continued

Druggability detection and analysis: MS detection of humanized anti-human PD-L1 monoclonal antibody after deamidation stress test

| Sample name | Peptide fragment | Sequence | Modification | Modification percentage | XIC area |
|---|---|---|---|---|---|
| | T32-35 | YCARNSLF (SEQ ID NO: 31) | Carbamidomethylation @2(96), deamidization @5(99) | 68.80% | 2.30E+05 |
| AH01950-pH9.0-48h | T33-35 | CARNSLF (SEQ ID NO: 32) | Carbamidomethylation @1(96), deamidization @4(99) | 100.00% | 7.07E+05 |
| | T33-36 | CARNSLFASW (SEQ ID NO: 33) | Carbamidomethylation @1(96), deamidization @4(99) | | 8.91E+04 |
| | T32-35 | YCARNSLF (SEQ ID NO: 31) | Carbamidomethylation @2(96), deamidization @5(99) | | 1.16E+06 |
| | T95-97 | NQVSLTCLVK (SEQ ID NO: 34) | Carbamidomethylation @7(365) | 99.10% | 1.88E+07 |
| | T95-97 | NQVSLTCLVK (SEQ ID NO: 34) | Deamidization @1(359), carbamidomethylation @7(365) | 0.90% | 1.63E+05 |
| AH01963-0h | T33-35 | CARNSLF (SEQ ID NO: 32) | Carbamidomethylation @1(96) | 32.80% | 1.82E+05 |
| | T32-35 | YCARNSLF (SEQ ID NO: 31) | Carbamidomethylation @2(96), deamidization @5(99) | 67.20% | 3.72E+05 |
| AH01963-pH9.0-48h | T33-36 | CARNSLFASW (SEQ ID NO: 33) | Carbamidomethylation @1(96), deamidization @4(99) | 100.00% | 5.16E+04 |
| | T32-35 | YCARNSLF (SEQ ID NO: 31) | Carbamidomethylation @2(96), deamidization @5(99) | | 5.99E+05 |
| AH02029-0h | T33-35 | CARNSLF (SEQ ID NO: 32) | Carbamidomethylation @1(96) | | 2.56E+05 |
| | T32-35 | YCARNSLF (SEQ ID NO: 31) | Carbamidomethylation @2(96) | 29.30% | 1.68E+05 |
| | T32-35 | YCARNSLF (SEQ ID NO: 31) | Carbamidomethylation @2(96), deamidization @5(99) | 70.70% | 4.07E+05 |
| AH02029-pH9.0-48h | T33-35 | CARNSLF (SEQ ID NO: 32) | Carbamidomethylation @1(96), deamidization @4(99) | | 1.37E+06 |
| | T33-36 | CARNSLFASW (SEQ ID NO: 33) | Carbamidomethylation @1(96), deamidization @4(99) | 100.00% | 1.63E+05 |
| | T32-35 | YCARNSLF (SEQ ID NO: 31) | Carbamidomethylation @2(96), deamidization @5(99) | | 2.46E+06 |

The verification results by ELISA (FIG. 7) show that AH01946, AH01950, AH01963 and AH02029 antibody molecules still retain good antigen binding ability under the conditions of oxidative stress treatment and deamidation treatment.

The antibody samples after deamidation stress treatment were determined by cIEF for the charge change of the antibody molecules after deamidation stress treatment (Table 11 and FIG. 8). The results show that under the extreme conditions of deamidation stress, the charge of the antibody molecule is changed, and the component in the acid peak increases significantly. Combined with the results of mass spectrometry, it is determined that the proportion of deamidation of amino acids in the antibody molecule increases. However, this change does not have a significant impact on the recognition of antigen by the antibody molecules, the ability of antibody to recognize the antigen before and after the treatment does not change, and the ELISA curves have a high degree of agreement.

TABLE 11

Druggability detection and analysis: cIEF detection of humanized anti-human PD-L1 monoclonal antibody after deamidation stress test

| Sample | pI (peak1) | Area percentage of peak1 | pI (peak2) | Area percentage of peak2 | pI (peak3) | Area percentage of peak3 |
|---|---|---|---|---|---|---|
| AH01946-0h | 8 | 83.97% | 7.84 | 14.71% | | |
| AH01946-pH9.0-48h | 7.93 | 40.18% | 7.81 | 42.75% | 7.6 | 17.07% |
| AH01950-0h | 8.01 | 83.79% | 7.85 | 14.51% | | |
| AH01950-pH9.0-48h | 7.94 | 33.43% | 7.82 | 42.37% | 7.61 | 20.14% |
| AH01963-0h | 7.99 | 82.71% | 7.82 | 15.96% | | |
| AH01963-pH9.0-48h | 7.94 | 29.27% | 7.82 | 43.68% | 7.61 | 22.43% |
| AH02029-0h | 7.99 | 80.89% | 7.82 | 17.37% | | |
| AH02029-pH9.0-48h | 7.94 | 30.72% | 7.82 | 42.68% | 7.61 | 22.16% |

Example 6: Detection of Cross-Recognition Ability of Humanized Anti-Human PD-L1 Monoclonal Antibody Through the above comparative analysis, the humanized anti-human PD-L1 monoclonal antibodies AH01946 and AH02029 were selected to produce stable expression cell lines, and the ability of the antibody molecules to recognize PD-L1 derived from humans and monkeys was further confirmed and used as a basis for drug metabolism and toxicity tests in animals.

Figure 9B:
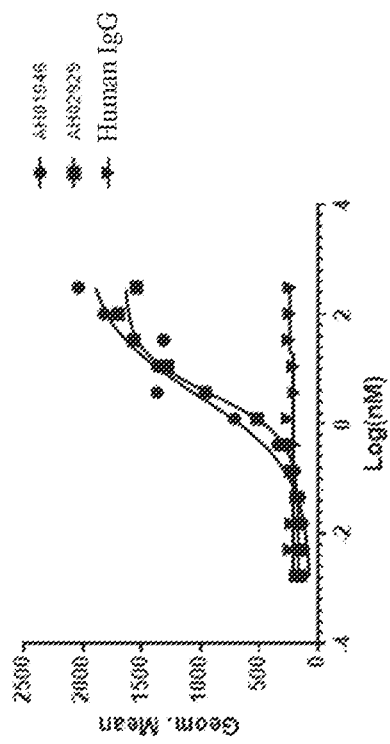
FIGS. 9A-9B show the detection and analysis by FACS of the binding of human/monkey PD-L1 on cell surface to monoclonal antibodies, specifically the analysis of binding of AH01946, AH02029, the negative control antibody human IgG and the positive control antibody Tecentriq to human PD-L1 (FIG. 9A); and the analysis of binding of AH01946, AH02029 and the negative control antibody human IgG to monkey PD-L1 (FIG. 9B)
Figure 9A:
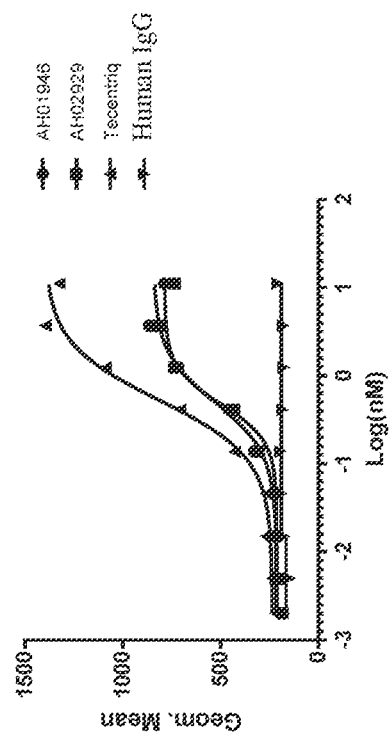

CHO cells expressing human or monkey PD-L1 and parent cells as a negative control were washed 3 times with PBS. $2.5 \times 10^5$ detection cells and 100 µl of 3-fold serial dilutions of purified antibody with an initial concentration of 300 nM were added to a 96-well plate and incubated at 4° C. for 1 hr. Then the cells were washed 3 times with PBS, 100 µl of iFluor-labeled goat anti-human IgG was added, and the cells were incubated at 4° C. for 45 min. Finally, the cells were washed 3 times with PBS, and the signal was read on FACS BD Calibur. As shown in FIG. 9A, the AH01946 and AH02029 antibodies and the human PD-L1 cell line all show a strong binding ability, showing a binding level comparable to Tecentriq control antibody, with an $EC_{50}$ of about 0.5 nM (Table 12).

TABLE 12

FACS test of antibodies binding to human PD-L1 on cell surface

|  | Tecentriq | AH01946 | AH02929 | Human IgG |
|---|---|---|---|---|
| Bottom | 238.1 | 216.7 | 214.7 | 166 |
| Top | 1400 | 843.9 | 787.5 | 190.7 |
| $LogEC_{50}$ | −0.273 | −0.3002 | −0.3205 | ~−1.824 |
| Hill Slope | 1.329 | 1.496 | 2.078 | ~92.15 |
| $EC_{50}$ (nM) | 0.5334 | 0.501 | 0.4781 | ~0.01498 |
| Span | 1162 | 627.2 | 572.7 | 24.67 |

Moreover, CHO cells overexpressing monkey PD-L1 were used to test the cross-recognition binding to monkey PD-L1 by the antibodies. As shown in FIG. 9B, the AH01946 and AH02029 antibodies and the monkey PD-L1 cell line all show a strong binding ability with an $EC_{50}$ of about 3.3 nM.

TABLE 13

FACS test of antibodies binding to monkey PD-L1 on cell surface

|  | AH01946 | AH02929 | Human IgG |
|---|---|---|---|
| Bottom | 63.39 | 166.9 | 215.7 |
| Top | 1991 | 1645 | 247.7 |
| $LogEC_{50}$ | 0.5178 | 0.5319 | ~1.286 |
| Hill Slope | 0.6424 | 1.114 | ~−55.86 |
| $EC_{50}$ (nM) | 3.295 | 3.403 | ~19.32 |
| Span | 1928 | 1478 | 32 |

Figure 10B:
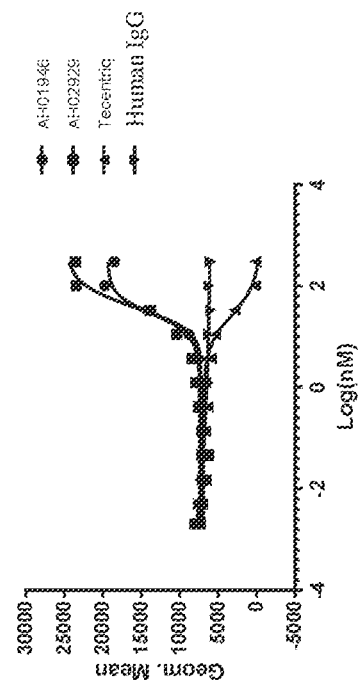
FIGS. 10A-10B shows the analysis of the effect of monoclonal antibodies on PD-1/PD-L1 interaction, specifically the analysis by ELISA of the effect of AH01946, AH02029, the negative control antibody human IgG and the positive control antibody Tecentriq on PD-1/PD-L1 binding (FIG. 10A); and the analysis by FACS of the effect of AH01946, AH02029, the negative control antibody human IgG and the positive control antibody Tecentriq on PD-1/PD-L1 binding (FIG. 10 B)
Figure 10A:
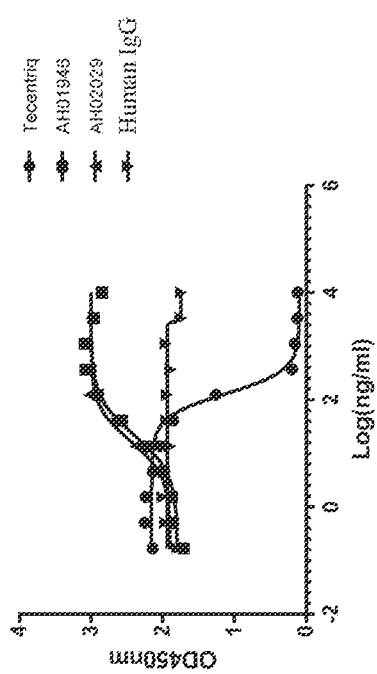

Example 7: Effect of Humanized Anti-Human PD-L1 Monoclonal Antibody on PD-1/PD-L1 Interaction The ELISA plate (Nunc) was coated with 100 µl/well of 0.5 µg/ml recombinant human PD-1 protein in PBS at 4° C. overnight. The plate was washed with PBS-T (0.05% Tween), and blocked with 200 µl/well of PBST containing 1% BSA at 37° C. for 0.5 hr. Then the blocking buffer was discarded, and 50 µl of 10 µg/ml purified antibody to be tested was added to the first test well. 3-fold serial dilutions were made, and a total of 11 test concentration gradients were given. Then 50 µl of biotin-labeled PD-L1-Fc (with a concentration of 0.3 µg/ml) was added to each well, and incubated at 37° C. for 1 hr. The plate was washed 3 times with PBST, and incubated with 100 µl/well of Streptavidin-HRP (SA-HRP, GenScript) at 37° C. for 10 min. Finally, the plate was washed 5 times with PBST, and then a TMB developing solution (GenScript) was added and incubated at room temperature for 15 min in the dark. The reaction was terminated by adding 50 µl of 1M HCl stop solution (Sigma). The plate was read at 450 nm on a microplate reader. As shown in FIG. 10A, the Tecentriq antibody shows an $IC_{50}$ of 129.6 ng/ml; and the AH01946 and AH02029 antibodies do not block, but promote the binding of PD-L1 and PD-1. The $EC_{50}$ of AH01946 antibody is 21.89 ng/ml, and the $EC_{50}$ of AH02029 antibody is 17.05 ng/ml.

TABLE 14

ELISA test of antibodies binding to human PD-1/PD-L1

|  | Tecentriq | AH01946 | AH02029 | Human IgG |
|---|---|---|---|---|
| Bottom | 0.09648 | 1.798 | 1.9 | 1.749 |
| Top | 2.154 | 3.005 | 3.004 | 1.935 |
| $LogEC_{50}$ | 2.113 | 1.34 | 1.232 | ~−3.459 |
| HillSlope | −1.991 | 1.219 | 1.356 | ~−23.09 |
| $EC_{50}$ (ng/ml) | 129.6 | 21.89 | 17.05 | ~2877 |
| Span | 2.058 | 1.207 | 1.104 | 0.1863 |

In the FACS test, CHO cells expressing human PD-1 and parent cells as a negative control were washed 3 times with PBS. $2.5 \times 10^5$ detection cells and 50 µl of 3-fold serial dilutions of purified antibody with an initial concentration of 300 nM were added to a 96-well plate. 50 µl of biotin-labeled PD-L1-Fc (with a concentration of 1.5 µg/ml) was added to each well, and incubated at 4° C. for 1 hr. Then the cells were washed 3 times with PBS, 100 µl of iFluor647-labeled streptavidin (1 µg/ml) was added, and the cells were incubated at 4° C. for 45 min. Finally, the cells were washed 3 times with PBS, and the signal was read on FACS BD Calibur. The result is shown in FIG. 10. The Tecentriq antibody shows an $IC_{50}$ of 26.86 nM at the cellular level; and the AH01946 and AH02029 antibodies promote the binding of PD-L1 and PD-1. The $EC_{50}$ of AH01946 antibody is 28.11 nM, and the $EC_{50}$ of AH02029 antibody is 38.67 nM.

TABLE 15

FACS test of antibodies binding to human PD-1/PD-L1

|  | Tecentriq | AH01946 | AH02929 | Human IgG |
|---|---|---|---|---|
| Bottom | −437.1 | 7232 | 7418 | 5878 |
| Top | 6879 | 19350 | 24811 | ~1.155e+006 |
| $LogEC_{50}$ | 1.429 | 1.449 | 1.587 | ~−17.52 |
| Hill Slope | −1.35 | 2.335 | 1.786 | ~−0.1871 |
| $EC_{50}$ (nM) | 26.86 | 28.11 | 38.67 | ~0.0 |
| Span | 7316 | 12118 | 17393 | ~1.149e+006 |

Unlike Tecentriq, these two antibodies do not have an inhibitory effect on the PD1-PD-L1 binding, but instead promote the PD1-PDL1 binding as the concentration increases. This is verified by both ELISA and FACS. After such an antibody binds to PD-L1, PD-L1 is seemed to be locked in a disabled state. PD-L1 is easy to bind to PD1, but not activated, and occupies the binding position at the same time to block the inhibitory effect.

Example 8: Verification of Cell Activity Function in the Presence of Humanized Anti-Human PD-L1 Monoclonal Antibody Combined with Tecentriq Human peripheral blood mononuclear cells (PBMC) were isolated, and then monocytes and CD4+ T cells were extracted using pan monocyte isolation kit and CD4+ T cell isolation kit (Miltenyi Biotech Inc.), respectively. The monocytes were differentiated into dendritic cells and treated with LPS until mature. The mature DC was coated on a 96-well plate, Tecentriq, AH01946, AH01950, AH01963, and AH02029 at a concentration of 0.03 µg/ml or a mixture of Tecentriq with a corresponding antibody were added respectively. After 72 hrs of incubation, the IL-2 and IFN-gamma kits based on HTRF principle from Cisbio were used to detect the content of IL-2 and IFN-gamma in the mixed cell supernatant.

Figure 11A:
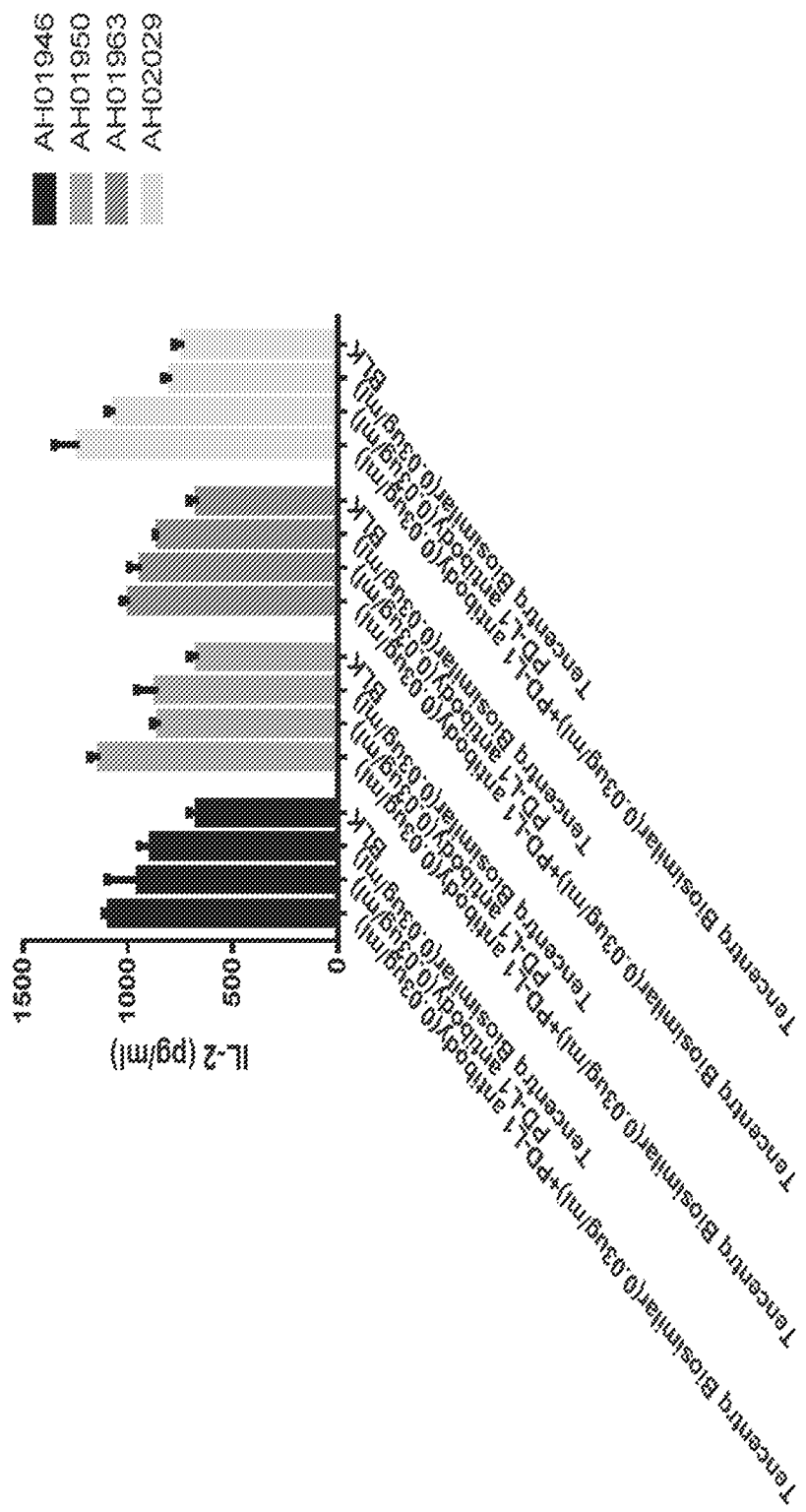
FIGS. 11A-11B shows the verification of cell activity function in the presence of a humanized anti-human PD-L1 monoclonal antibody in combination with Tecentriq, specifically secretion of IL-2 (FIG. 11A) and IFN-γ (FIG. 11 B) by T cells induced by AH01946, AH01950, AH01963, or AH02029 combined with Tecentriq vs each antibody molecule used alone, where BLK is the negative control group, that is, no antibody is added to the sample.
Figure 11B:
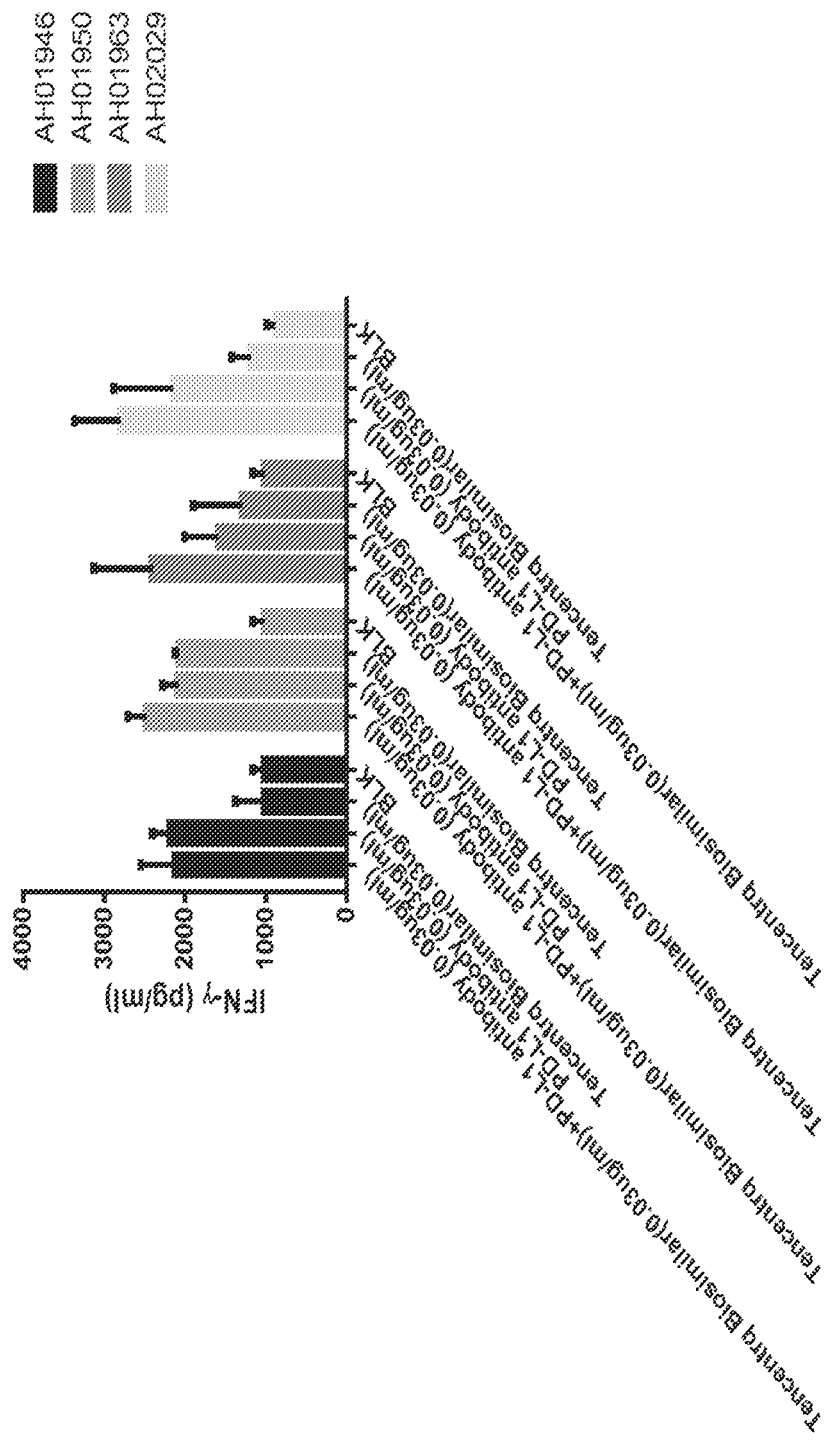

FIGS. 11A and B show that compared with Tecentriq alone or anti-PD-L1 antibody alone, Tecentriq, combined with AH01946, AH01950, AH01963 and AH02029, respectively, stimulates the increase of IL-2 and IFN-gamma secretion in cells, and has a certain synergistic effect. Particularly the combination of Tecentriq and AH02029 has a better synergistic effect in stimulation of cells.

Following the above experimental method, the concentration of Tecentriq was fixed at 0.01 µg/ml, and then different concentrations of anti-PD-L1 antibody clone AH02029 were added. The wells with different concentrations of Tecentriq and AH02029 added alone were used as controls. The cell activity function was verified, and the contents of IL-2 and IFN-gamma in the mixed cell supernatant was detected.

Figure 12A:
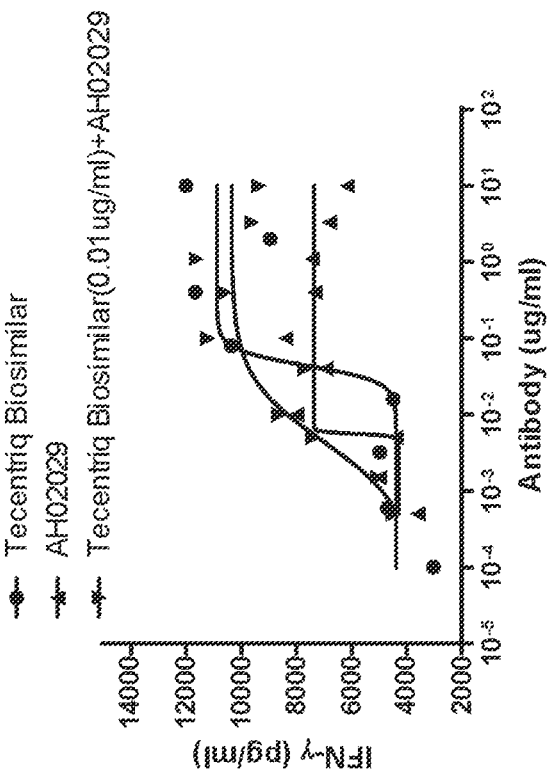
FIGS. 12A-12B shows the verification of cell activity function in the presence of a humanized anti-human PD-L1 monoclonal antibody in combination with Tecentriq, specifically secretion of IL-2 (FIG. 12A) and IFN-γ (FIG. 12 B) by T cells induced by a series of gradient concentrations of AH02029 combined with a fixed concentration of Tecentriq vs each antibody molecule used alone.
Figure 12B:
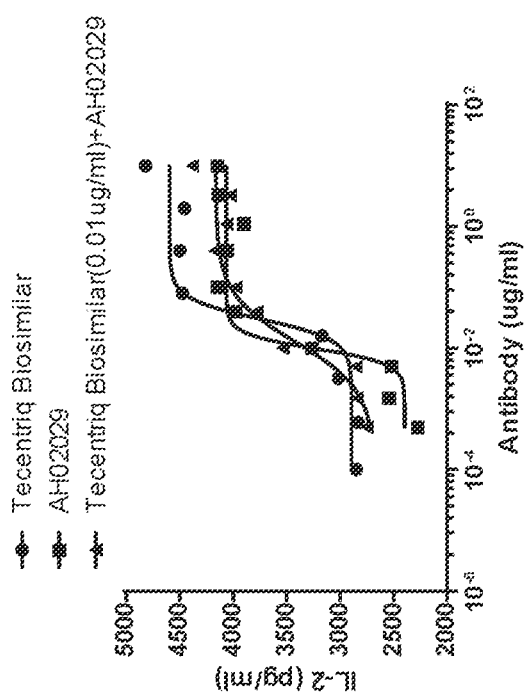

As shown in FIGS. 12A and B, fixing Tecentriq at a low concentration is not enough to activate the release of cytokines in MLR. The use of anti-PD-L1 antibody AH02029 contributes to the production and release of cytokines IL-2 and IFN-gamma. In Tables 16 and 17, the $EC_{50}$ of AH02029 in combination with 0.01 µg/ml Tecentriq in stimulating IL-2 and IFN-gamma is 0.013 µg/ml and 0.0045 µg/ml respectively, and both of them enable the effect of 0.01 µg/ml Tecentriq in stimulating the secretion of IL-2 and IFN-gamma to increase from a bottom value to a top value.

TABLE 16

Analysis of AH02029 combined with Tecentriq to stimulate cells to secrete IL-2

|  | AH02029 | Tecentriq Biosimilar | Tecentriq Biosimilar (0.01 ug/ml) + AH02029 |
|---|---|---|---|
| Bottom | 2,401 | 2898 | 2685 |
| Top | 4067 | 4596 | 4164 |
| LogEC50 | −2.007 | −1.522 | −1.895 |
| HillSlope | 3.503 | 2.548 | 1.099 |
| EC50 (ug/ml) | 0.010 | 0.030 | 0.013 |
| Span | 1666 | 1699 | 1480 |

TABLE 17

Analysis of AH02029 combined with Tecentriq to stimulate cells to secrete IFN-γ

|  | AH02029 | Tecentriq Biosimilar | Tecentriq Biosimilar (0.01 ug/ml) + AH02029 |
|---|---|---|---|
| Bottom | 4297 | 4391 | 3729 |
| Top | 7365 | 10881 | 10364 |
| LogEC50 | ~−2.251 | −1.357 | −2.347 |

TABLE 17-continued

Analysis of AH02029 combined with Tecentriq to stimulate cells to secrete IFN-γ

|  | AH02029 | Tecentriq Biosimilar | Tecentriq Biosimilar (0.01 ug/ml) + AH02029 |
|---|---|---|---|
| HillSlope | ~30.89 | 4.102 | 1.021 |
| EC50 (ug/ml) | ~0.005608 | 0.044 | 0.004501 |
| Span | 3069 | 6490 | 6634 |

Example 9: Pharmacodynamic Test of PD-L1 Antibody, PD-L1 Antibody Combined with PD1 Antibody or Another PD-L1 Antibody in hPD1/PD-L1 Dual Humanized Mouse Animal Model of MC38-hPD-L1 Colon Cancer The MC38-hPD-L1 cells were inoculated subcutaneously on the right side of hPD1/PD-L1 dual humanized mice. When the tumors were grown to about 60-90 mm³, the animals were selected according to the tumor volume and randomly grouped into 7 groups in total, each having 6 animals. The groups included a 1 mg/kg hIgG group, a 10 mg/kg AH01946 group, a 10 mg/kg 53C1F3D4 (prepared following the method in Chinese Patent No. CN108239149A) group, a 10 mg/kg 53C1F3D4+10 mg/kgAH01946 group, a 10 mg/kg Tecentriq+10 mg/kg AH01946 group, a 5 mg/kg Keytruda (Merck & Co., Inc.; batch number: R030484) group, and a 5 mg/kg Keytruda+10 mg/kg AH01946 1 group. The mice were injected intraperitoneally, once every 4 days, for 4 consecutive doses, and the experiment was ended 7 days after the last dose. During the administration and observation period, the body weight and tumor volume of mice were measured twice a week, the measured values were recorded, and the tumor volume growth inhibition rate was calculated.

In the experiment, all the animals were in good activity and eating state during the administration, and tolerated each test product well. At the end of the experiment, the tumor volume growth inhibition rate $TGI_{TV}$ in the hIgG group, AH01946 group, 53CIF3D4 group, 53C1F3D4+AH01946 group, Tecentriq+AH01946 group, Keytruda group, and Keytruda+AH01946 group was 23.1%, 39.6%, 86.8%, 53.4%, 72.5% and 84.2% respectively.

A single administration of 10 mg/kg AH01946 or 10 mg/kg 53C1F3D4 does not have a significant efficacy. However, 10 mg/kg AH01946 can synergize the efficacy of 53C1F3D4 and Tecentriq, and the combination of AH01946 with 53C1F3D4 and the combination of AH01946 with Keytruda show significant efficacy in the hPD1/PD-L1 dual humanized mouse animal model of MC38-hPD-L1 colon cancer (p<0.001).

Example 10: Pharmacodynamic Test of Low-Dose PD-L1 Antibody Combined with PD1 Antibody and PD-L1 Antibody in PD1/PD-L1 Dual Humanized Mouse Animal Model of MC38-hPD-L1 Colon Cancer The MC38-hPD-L1 cells were inoculated subcutaneously on the right side of hPD1/PD-L1 dual humanized mice. When the tumors were grown to about 60-90 mm³, the animals were selected according to the tumor volume and randomly grouped into 6 groups in total, each having 6 animals. The groups included a 1 mg/kg hIgG group, a 1 mg/kg Keytrud group, a 1 mg/kg Keytruda+1 mg/kg AH01946 group, a 1 mg/kg Keytruda+10 mg/kg AH01946 group, a 10 mg/kg Tecentriq group, a 10 mg/kg Tecentriq+1 mg/kgAH01946 group. The mice were injected intraperitoneally, once every 4 days, for 4 consecutive doses, and the experiment was ended 7 days after the last dose. During the administration and observation period, the body weight and tumor volume of mice were measured twice a week, the measured values were recorded, and the tumor volume growth inhibition rate was calculated.

In the experiment, all the animals were in good activity and eating state during the administration, and tolerated each test product well. At the end of the experiment, the tumor volume growth inhibition rate $TG_{ITV}$ in the hIgG group, the Keytruda group, the Keytruda+1 mg/kg AH01946 group, the Keytruda+10 mg/kg AH01946 group, the Tecentriq group, and the Tecentriq+1 mg/kg AH01946 group are respectively 8.0%, 5.47%, 60.2%, 79.1% and 82.5%.

A single administration of 1 mg/kg Keytruda or 1 mg/kg Keytruda+1 mg/kg AH01946 does not have a significant efficacy. However, 10 mg/kg AH01946 can synergize the efficacy of 1 mg/kg Keytruda, to exert a certain efficacy in the hPD1/PD-L1 dual humanized mouse animal model of MC38-hPD-L1 colon cancer (p=0.07).

What is claimed is:

1. A humanized anti-human PD-L1 monoclonal antibody or antigen-binding fragment thereof, which specifically binds to PD-L1, and relieves the immunosuppression by indirectly blocking the interaction between PD1 and PD-L1, which comprises CDR-H1 having the amino acid sequence of SGYTWH (SEQ ID NO:35), CDR-H2 having the amino acid sequence of YIHYSGSTKYNPSLKS (SEQ ID NO:36), CDR-H3 having the amino acid sequence of NSLFAS (SEQ ID NO:37), CDR-L1 having the amino acid sequence of RASESVDTYGDSFMH (SEQ ID NO:38), CDR-L2 having the amino acid sequence of RASNLES (SEQ ID NO:39), and CDR-L3 having the amino acid sequence of QQSNEAPYT (SEQ ID NO:40), and which comprises a heavy chain variable region and a light chain variable region selected from a combination of:

a heavy chain variable region as shown in SEQ ID NO:9 and a light chain variable region as shown in SEQ ID NO:17;

a heavy chain variable region as shown in SEQ ID NO: 10 and a light chain variable region as shown in SEQ ID NO: 18;

a heavy chain variable region as shown in SEQ ID NO:11 and a light chain variable region as shown in SEQ ID NO:19;

a heavy chain variable region as shown in SEQ ID NO: 12 and a light chain variable region as shown in SEQ ID NO:20;

a heavy chain variable region as shown in SEQ ID NO:13 and a light chain variable region as shown in SEQ ID NO:21;

a heavy chain variable region as shown in SEQ ID NO: 14 and a light chain variable region as shown in SEQ ID NO:22;

a heavy chain variable region as shown in SEQ ID NO:15 and a light chain variable region as shown in SEQ ID NO:23;

a heavy chain variable region as shown in SEQ ID NO: 16 and a light chain variable region as shown in SEQ ID NO:24; or amino acid sequences having up to 6 conservative amino acid substitution(s) in each group of the foregoing sequences.

2. The humanized anti-human PD-L1 monoclonal antibody or antigen-binding fragment thereof according to claim 1, wherein the heavy chain variable region and the light chain variable region are selected from a combination of:

a heavy chain variable region as shown in SEQ ID NO:9 and a light chain variable region as shown in SEQ ID NO:17;

a heavy chain variable region as shown in SEQ ID NO: 10 and a light chain variable region as shown in SEQ ID NO:18;

a heavy chain variable region as shown in SEQ ID NO:11 and a light chain variable region as shown in SEQ ID NO:19;

a heavy chain variable region as shown in SEQ ID NO: 12 and a light chain variable region as shown in SEQ ID NO:20;

a heavy chain variable region as shown in SEQ ID NO:13 and a light chain variable region as shown in SEQ ID NO:21;

a heavy chain variable region as shown in SEQ ID NO:14 and a light chain variable region as shown in SEQ ID NO:22;

a heavy chain variable region as shown in SEQ ID NO:15 and a light chain variable region as shown in SEQ ID NO:23; or a heavy chain variable region as shown in SEQ ID NO: 16 and a light chain variable region as shown in SEQ ID NO:24.

3. The humanized anti-human PD-L1 monoclonal antibody or antigen-binding fragment thereof according to claim 1, having a disassociation constant $K_D$ from PD-L1 of less than about 3 nM.

4. An isolated polynucleotide, encoding the humanized anti-human PD-L1 monoclonal antibody or antigen-binding fragment thereof according to claim 1.

5. The polynucleotide according to claim 4, comprising a heavy chain coding sequence encoding the heavy chain variable region of the humanized anti-human PD-L1 monoclonal antibody, and a light chain coding sequence encoding the light chain variable region of the humanized anti-human PD-L1 monoclonal antibody.

6. An expression vector, comprising the polynucleotide according to claim 4.

7. A host cell, comprising the expression vector according to claim 6.

8. A method for enhancing an anti-tumor response, alleviating tumors or inhibiting the growth of tumor cells, or treating tumors, in a subject in need thereof, wherein the method comprises administering to the subject a therapeutically effective amount of the humanized anti-human PD-L1 monoclonal antibody or antigen-binding fragment thereof according to claim 1.

9. An anti-tumor pharmaceutical composition, comprising an effective amount of the humanized anti-human PD-L1 monoclonal antibody or antigen-binding fragment thereof according to claim 1, and a pharmaceutically acceptable carrier.

10. The pharmaceutical composition according to claim 9, wherein the tumor is selected from colon cancer, pancreatic cancer, gastric cancer, non-small cell lung cancer, melanoma, bladder cancer, or kidney cancer.

11. The method according to claim 8, wherein the antibody or antigen-binding fragment thereof is administered in combination with another PD-L1 antibody to synergistically stimulate an immune response.

12. The method according to claim 8, wherein a low dose of the antibody or antigen-binding fragment thereof is administered in combination with a low dose of another PD-L1 antibody or PD-1 antibody to synergistically inhibit the tumor growth.

13. A method for preparing the humanized anti-human PD-L1 monoclonal antibody or antigen-binding fragment thereof according to claim 1, comprising:

(1) humanizing the murine antibody, and obtaining variable region coding sequences of the light chain and the heavy chain of the humanized anti-human PD-L1 monoclonal antibody or antigen-binding fragment thereof; and (2) using the variable region coding sequences in recombinant antibody production to obtain the functional humanized anti-human PD-L1 monoclonal antibody or antigen-binding fragment thereof.

14. The method according to claim 8, wherein the antibody or antigen-binding fragment thereof is administered in combination with atezolizumab to synergistically stimulate the immune response to activate T cells to secrete cytokines.

15. The method according to claim 8, wherein the tumor is selected from colon cancer, pancreatic cancer, gastric cancer, non-small cell lung cancer, melanoma, bladder cancer, or kidney cancer.

* * * * *

SEQUENCE LISTING

```
<160> NUMBER OF SEQ ID NOS: 40

<210> SEQ ID NO 1
<211> LENGTH: 115
<212> TYPE: PRT
<213> ORGANISM: Mus musculus

<400> SEQUENCE: 1

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Thr Trp His Trp Ile Arg Gln Phe Pro Gly Asn Lys Leu Glu Trp
        35                  40                  45

Met Gly Tyr Ile His Tyr Ser Gly Ser Thr Lys Tyr Asn Pro Ser Leu
    50                  55                  60

Lys Ser Arg Phe Ser Ile Thr Arg Asp Thr Ser Lys Asn Gln Phe Phe
65                  70                  75                  80

Leu Gln Leu Asn Ser Met Thr Ala Glu Asp Thr Ala Thr Tyr Tyr Cys
                85                  90                  95

Ala Arg Asn Ser Leu Phe Ala Ser Trp Gly His Gly Thr Leu Val Thr
            100                 105                 110

Val Ser Ala
        115

<210> SEQ ID NO 2
<211> LENGTH: 111
<212> TYPE: PRT
<213> ORGANISM: Mus musculus

<400> SEQUENCE: 2

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Thr Tyr
            20                  25                  30

Gly Asp Ser Phe Met His Trp Phe Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Ala Pro Tyr Thr Phe Gly Gly Gly Thr Lys Leu Glu Ile Lys
            100                 105                 110
```

<210> SEQ ID NO 3
<211> LENGTH: 115
<212> TYPE: PRT
<213> ORGANISM: Artificial Sequence
<220> FEATURE:
<223> OTHER INFORMATION: mPD-L1Ab-VH-GRAFTED

<400> SEQUENCE: 3

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Thr Trp His Trp Ile Arg Gln His Pro Gly Lys Gly Leu Glu Trp
        35                  40                  45

Ile Gly Tyr Ile His Tyr Ser Gly Ser Thr Lys Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asn Ser Leu Phe Ala Ser Trp Gly Gln Gly Thr Leu Val Thr
            100                 105                 110

Val Ser Ser
        115
```

<210> SEQ ID NO 4
<211> LENGTH: 111
<212> TYPE: PRT
<213> ORGANISM: Artificial Sequence
<220> FEATURE:
<223> OTHER INFORMATION: mPD-L1Ab-VL-GRAFTED

<400> SEQUENCE: 4

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Tyr
            20                  25                  30

Gly Asp Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Ala Pro Tyr Thr Phe Gly Gly Gly Thr Lys Leu Glu Ile Lys
            100                 105                 110
```

<210> SEQ ID NO 5
<211> LENGTH: 115
<212> TYPE: PRT
<213> ORGANISM: Artificial Sequence
<220> FEATURE:
<223> OTHER INFORMATION: mPD-L1Ab-VH-CBM

<400> SEQUENCE: 5

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
```

```
            20                  25                  30
Tyr Thr Trp His Trp Ile Arg Gln His Pro Gly Lys Gly Leu Glu Trp
            35                  40                  45

Met Gly Tyr Ile His Tyr Ser Gly Ser Thr Lys Tyr Asn Pro Ser Leu
    50                  55                  60

Lys Ser Arg Phe Thr Ile Ser Arg Asp Thr Ser Lys Asn Gln Phe Ser
65                  70                  75                  80

Leu Lys Leu Ser Ser Met Thr Ala Ala Asp Thr Ala Val Tyr Tyr Cys
                85                  90                  95

Ala Arg Asn Ser Leu Phe Ala Ser Trp Gly Gln Gly Thr Leu Val Thr
            100                 105                 110

Val Ser Ser
        115

<210> SEQ ID NO 6
<211> LENGTH: 111
<212> TYPE: PRT
<213> ORGANISM: Artificial Sequence
<220> FEATURE:
<223> OTHER INFORMATION: mPD-L1Ab-VL-CBM

<400> SEQUENCE: 6

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Tyr
            20                  25                  30

Gly Asp Ser Phe Met His Trp Phe Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Val Tyr Tyr Cys Gln Gln Ser Asn
                85                  90                  95

Glu Ala Pro Tyr Thr Phe Gly Gly Gly Thr Lys Leu Glu Ile Lys
            100                 105                 110

<210> SEQ ID NO 7
<211> LENGTH: 115
<212> TYPE: PRT
<213> ORGANISM: Artificial Sequence
<220> FEATURE:
<223> OTHER INFORMATION: mPD-L1Ab-VH-5BM

<400> SEQUENCE: 7

Gln Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Gly
            20                  25                  30

Tyr Thr Trp His Trp Ile Arg Gln His Pro Gly Lys Gly Leu Glu Trp
            35                  40                  45

Met Gly Tyr Ile His Tyr Ser Gly Ser Thr Lys Tyr Asn Pro Ser Leu
    50                  55                  60

Lys Ser Arg Phe Ser Ile Thr Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95
```

Ala Arg Asn Ser Leu Phe Ala Ser Trp Gly Gln Gly Thr Leu Val Thr
            100                 105                 110

Val Ser Ser
    115

<210> SEQ ID NO 8
<211> LENGTH: 112
<212> TYPE: PRT
<213> ORGANISM: Artificial Sequence
<220> FEATURE:
<223> OTHER INFORMATION: mPD-L1Ab-VL-5BM

<400> SEQUENCE: 8

Asp Ile Val Leu Thr Gln Ser Pro Asp Ser Leu Ala Val Ser Leu Gly
1               5                   10                  15

Glu Arg Ala Thr Ile Ser Cys Arg Ala Ser Glu Ser Val Asp Thr Tyr
            20                  25                  30

Gly Asp Ser Phe Met His Trp Phe Gln Gln Lys Pro Gly Gln Pro Pro
        35                  40                  45

Lys Leu Leu Ile Tyr Arg Ala Ser Asn Leu Glu Ser Gly Ile Pro Asp
    50                  55                  60

Arg Phe Ser Gly Ser Gly Ser Arg Thr Asp Phe Thr Leu Thr Ile
65                  70                  75                  80

Ser Ser Leu Gln Ala Glu Asp Val Ala Val Tyr Tyr Cys Gln Gln Ser
                85                  90                  95

Asn Glu Ala Pro Tyr Thr Phe Gly Gly Gly Thr Lys Leu Glu Ile Lys
            100                 105                 110

<210> SEQ ID NO 9
<211> LENGTH: 115
<212> TYPE: PRT
<213> ORGANISM: Artificial Sequence
<220> FEATURE:
<223> OTHER INFORMATION: AH02029-VH

<400> SEQUENCE: 9

Gln Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Gly
            20                  25                  30

Tyr Thr Trp His Trp Ile Arg Gln His Pro Gly Lys Gly Leu Glu Trp
        35                  40                  45

Ile Gly Tyr Ile His Tyr Ser Gly Ser Thr Lys Tyr Asn Pro Ser Leu
    50                  55                  60

Lys Ser Arg Val Ser Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asn Ser Leu Phe Ala Ser Trp Gly Gln Gly Thr Leu Val Thr
            100                 105                 110

Val Ser Ser
    115

<210> SEQ ID NO 10
<211> LENGTH: 115
<212> TYPE: PRT
<213> ORGANISM: Artificial Sequence
<220> FEATURE:
<223> OTHER INFORMATION: AH02030-VH

```
<400> SEQUENCE: 10

Gln Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Gly
            20                  25                  30

Tyr Thr Trp His Trp Ile Arg Gln His Pro Gly Lys Gly Leu Glu Trp
            35                  40                  45

Ile Gly Tyr Ile His Tyr Ser Gly Ser Thr Lys Tyr Asn Pro Ser Leu
50                  55                  60

Lys Ser Arg Phe Thr Ile Thr Arg Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Asn Ser Leu Phe Ala Ser Trp Gly Gln Gly Thr Leu Val Thr
            100                 105                 110

Val Ser Ser
        115

<210> SEQ ID NO 11
<211> LENGTH: 115
<212> TYPE: PRT
<213> ORGANISM: Artificial Sequence
<220> FEATURE:
<223> OTHER INFORMATION: AH02033-VH

<400> SEQUENCE: 11

Gln Val Gln Leu Gln Glu Ser Gly Pro Gly Leu Val Lys Pro Ser Gln
1               5                   10                  15

Thr Leu Ser Leu Thr Cys Thr Val Thr Gly Tyr Ser Ile Thr Ser Gly
            20                  25                  30

Tyr Thr Trp His Trp Ile Arg Gln His Pro Gly Lys Gly Leu Glu Trp
            35                  40                  45

Met Gly Tyr Ile His Tyr Ser Gly Ser Thr Lys Tyr Asn Pro Ser Leu
50                  55                  60

Lys Ser Arg Phe Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg Asn Ser Leu Phe Ala Ser Trp Gly Gln Gly Thr Leu Val Thr
            100                 105                 110

Val Ser Ser
        115

<210> SEQ ID NO 12
<211> LENGTH: 115
<212> TYPE: PRT
<213> ORGANISM: Artificial Sequence
<220> FEATURE:
<223> OTHER INFORMATION: AH01946-VH

<400> SEQUENCE: 12

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Thr Trp His Trp Ile Arg Gln His Pro Gly Lys Gly Leu Glu Trp
            35                  40                  45
```

```
Ile Gly Tyr Ile His Tyr Ser Gly Ser Thr Lys Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Met Thr Ala Ala Asp Thr Ala Val Tyr Tyr Cys
                85                  90                  95

Ala Arg Asn Ser Leu Phe Ala Ser Trp Gly Gln Gly Thr Leu Val Thr
                100                 105                 110

Val Ser Ser
        115

<210> SEQ ID NO 13
<211> LENGTH: 115
<212> TYPE: PRT
<213> ORGANISM: Artificial Sequence
<220> FEATURE:
<223> OTHER INFORMATION: AH01947-VH

<400> SEQUENCE: 13

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
                20                  25                  30

Tyr Thr Trp His Trp Ile Arg Gln His Pro Gly Lys Gly Leu Glu Trp
            35                  40                  45

Ile Gly Tyr Ile His Tyr Ser Gly Ser Thr Lys Tyr Asn Pro Ser Leu
        50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asn Ser Leu Phe Ala Ser Trp Gly Gln Gly Thr Leu Val Thr
                100                 105                 110

Val Ser Ser
        115

<210> SEQ ID NO 14
<211> LENGTH: 115
<212> TYPE: PRT
<213> ORGANISM: Artificial Sequence
<220> FEATURE:
<223> OTHER INFORMATION: AH01950-VH

<400> SEQUENCE: 14

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
                20                  25                  30

Tyr Thr Trp His Trp Ile Arg Gln His Pro Gly Lys Gly Leu Glu Trp
            35                  40                  45

Ile Gly Tyr Ile His Tyr Ser Gly Ser Thr Lys Tyr Asn Pro Ser Leu
        50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asn Ser Leu Phe Ala Ser Trp Gly Gln Gly Thr Leu Val Thr
                100                 105                 110
```

```
Val Ser Ser
        115

<210> SEQ ID NO 15
<211> LENGTH: 115
<212> TYPE: PRT
<213> ORGANISM: Artificial Sequence
<220> FEATURE:
<223> OTHER INFORMATION: AH01963-VH

<400> SEQUENCE: 15

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Thr Trp His Trp Ile Arg Gln His Pro Gly Lys Gly Leu Glu Trp
        35                  40                  45

Ile Gly Tyr Ile His Tyr Ser Gly Ser Thr Lys Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asn Ser Leu Phe Ala Ser Trp Gly Gln Gly Thr Leu Val Thr
            100                 105                 110

Val Ser Ser
        115

<210> SEQ ID NO 16
<211> LENGTH: 115
<212> TYPE: PRT
<213> ORGANISM: Artificial Sequence
<220> FEATURE:
<223> OTHER INFORMATION: AH01964-VH

<400> SEQUENCE: 16

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Gly
            20                  25                  30

Tyr Thr Trp His Trp Ile Arg Gln His Pro Gly Lys Gly Leu Glu Trp
        35                  40                  45

Ile Gly Tyr Ile His Tyr Ser Gly Ser Thr Lys Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asn Ser Leu Phe Ala Ser Trp Gly Gln Gly Thr Leu Val Thr
            100                 105                 110

Val Ser Ser
        115

<210> SEQ ID NO 17
<211> LENGTH: 111
<212> TYPE: PRT
<213> ORGANISM: Artificial Sequence
<220> FEATURE:
<223> OTHER INFORMATION: AH02029-VL
```

<400> SEQUENCE: 17

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Tyr
            20                  25                  30

Gly Asp Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Ala Pro Tyr Thr Phe Gly Gly Gly Thr Lys Leu Glu Ile Lys
            100                 105                 110

<210> SEQ ID NO 18
<211> LENGTH: 111
<212> TYPE: PRT
<213> ORGANISM: Artificial Sequence
<220> FEATURE:
<223> OTHER INFORMATION: AH02030-VL

<400> SEQUENCE: 18

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Tyr
            20                  25                  30

Gly Asp Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Ala Pro Tyr Thr Phe Gly Gly Gly Thr Lys Leu Glu Ile Lys
            100                 105                 110

<210> SEQ ID NO 19
<211> LENGTH: 111
<212> TYPE: PRT
<213> ORGANISM: Artificial Sequence
<220> FEATURE:
<223> OTHER INFORMATION: AH02033-VL

<400> SEQUENCE: 19

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Tyr
            20                  25                  30

Gly Asp Ser Phe Met His Trp Phe Gln Gln Lys Pro Gly Gln Pro Pro
        35                  40                  45

Lys Leu Leu Ile Tyr Arg Ala Ser Asn Leu Glu Ser Gly Ile Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Ala Pro Tyr Thr Phe Gly Gly Gly Thr Lys Leu Glu Ile Lys
            100                 105                 110

<210> SEQ ID NO 20
<211> LENGTH: 111
<212> TYPE: PRT
<213> ORGANISM: Artificial Sequence
<220> FEATURE:
<223> OTHER INFORMATION: AH01946-VL

<400> SEQUENCE: 20

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Tyr
            20                  25                  30

Gly Asp Ser Phe Met His Trp Phe Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Val Tyr Tyr Cys Gln Gln Ser Asn
                85                  90                  95

Glu Ala Pro Tyr Thr Phe Gly Gly Gly Thr Lys Leu Glu Ile Lys
            100                 105                 110

<210> SEQ ID NO 21
<211> LENGTH: 111
<212> TYPE: PRT
<213> ORGANISM: Artificial Sequence
<220> FEATURE:
<223> OTHER INFORMATION: AH01947-VL

<400> SEQUENCE: 21

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Tyr
            20                  25                  30

Gly Asp Ser Phe Met His Trp Phe Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Ala Pro Tyr Thr Phe Gly Gly Gly Thr Lys Leu Glu Ile Lys
            100                 105                 110

<210> SEQ ID NO 22
<211> LENGTH: 111
<212> TYPE: PRT
<213> ORGANISM: Artificial Sequence
<220> FEATURE:
<223> OTHER INFORMATION: AH01950-VL

<400> SEQUENCE: 22

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Tyr
            20                  25                  30

Gly Asp Ser Phe Met His Trp Phe Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Ala Pro Tyr Thr Phe Gly Gly Gly Thr Lys Leu Glu Ile Lys
            100                 105                 110

<210> SEQ ID NO 23
<211> LENGTH: 111
<212> TYPE: PRT
<213> ORGANISM: Artificial Sequence
<220> FEATURE:
<223> OTHER INFORMATION: AH01963-VL

<400> SEQUENCE: 23

Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Tyr
            20                  25                  30

Gly Asp Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Val Gln Ala Glu Asp Val Ala Val Tyr Tyr Cys Gln Gln Ser Asn
                85                  90                  95

Glu Ala Pro Tyr Thr Phe Gly Gly Gly Thr Lys Leu Glu Ile Lys
            100                 105                 110

<210> SEQ ID NO 24
<211> LENGTH: 108
<212> TYPE: PRT
<213> ORGANISM: Artificial Sequence
<220> FEATURE:
<223> OTHER INFORMATION: AH01964-VL

<400> SEQUENCE: 24

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Thr Tyr
            20                  25                  30

Gly Asp Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Ala Pro Tyr Thr Phe Gly Gly Gly Thr Lys Leu
            100                 105

<210> SEQ ID NO 25
<211> LENGTH: 13
<212> TYPE: PRT
<213> ORGANISM: Artificial Sequence
<220> FEATURE:
<223> OTHER INFORMATION: C76-77 Peptide Fragment

<400> SEQUENCE: 25

Ser Cys Ser Val Met His Glu Ala Leu His Asn His Tyr
1               5                   10

<210> SEQ ID NO 26
<211> LENGTH: 15
<212> TYPE: PRT
<213> ORGANISM: Artificial Sequence
<220> FEATURE:
<223> OTHER INFORMATION: C21-23 Peptide Fragment

<400> SEQUENCE: 26

Ser Leu Lys Leu Ser Ser Met Thr Ala Ala Asp Thr Ala Val Tyr
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: C54-57 Peptide Fragment

<400> SEQUENCE: 27

Thr Val Leu His Gln Asp Trp Leu Asn Gly Lys Glu Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: C46-47 Peptide Fragment

<400> SEQUENCE: 28

Phe Pro Pro Lys Pro Lys Asp Thr Leu Met Ile
1               5                   10

<210> SEQ ID NO 29
<211> LENGTH: 24
<212> TYPE: PRT
<213> ORGANISM: Artificial Sequence
<220> FEATURE:
<223> OTHER INFORMATION: C47-48 Peptide Fragment

<400> SEQUENCE: 29

Met Ile Ser Arg Thr Pro Glu Val Thr Cys Val Val Val Asp Val Ser
1               5                   10                  15

His Glu Asp Pro Glu Val Lys Phe
            20

<210> SEQ ID NO 30
<211> LENGTH: 19
<212> TYPE: PRT
<213> ORGANISM: Artificial Sequence
<220> FEATURE:
<223> OTHER INFORMATION: C53-57 Peptide Fragment

```
<400> SEQUENCE: 30

Arg Val Val Ser Val Leu Thr Val Leu His Gln Asp Trp Leu Asn Gly
1               5                   10                  15

Lys Glu Tyr

<210> SEQ ID NO 31
<211> LENGTH: 8
<212> TYPE: PRT
<213> ORGANISM: Artificial Sequence
<220> FEATURE:
<223> OTHER INFORMATION: T32-35 Peptide Fragment

<400> SEQUENCE: 31

Tyr Cys Ala Arg Asn Ser Leu Phe
1               5

<210> SEQ ID NO 32
<211> LENGTH: 7
<212> TYPE: PRT
<213> ORGANISM: Artificial Sequence
<220> FEATURE:
<223> OTHER INFORMATION: T33-35 Peptide Fragment

<400> SEQUENCE: 32

Cys Ala Arg Asn Ser Leu Phe
1               5

<210> SEQ ID NO 33
<211> LENGTH: 10
<212> TYPE: PRT
<213> ORGANISM: Artificial Sequence
<220> FEATURE:
<223> OTHER INFORMATION: T33-36 Peptide Fragment

<400> SEQUENCE: 33

Cys Ala Arg Asn Ser Leu Phe Ala Ser Trp
1               5                   10

<210> SEQ ID NO 34
<211> LENGTH: 10
<212> TYPE: PRT
<213> ORGANISM: Artificial Sequence
<220> FEATURE:
<223> OTHER INFORMATION: T95-97 Peptide Fragment

<400> SEQUENCE: 34

Asn Gln Val Ser Leu Thr Cys Leu Val Lys
1               5                   10

<210> SEQ ID NO 35
<211> LENGTH: 6
<212> TYPE: PRT
<213> ORGANISM: Artificial Sequence
<220> FEATURE:
<223> OTHER INFORMATION: CDR-H1

<400> SEQUENCE: 35

Ser Gly Tyr Thr Trp His
1               5

<210> SEQ ID NO 36
<211> LENGTH: 16
<212> TYPE: PRT
<213> ORGANISM: Artificial Sequence
<220> FEATURE:
```

```
<223> OTHER INFORMATION: CDR-H2

<400> SEQUENCE: 36

Tyr Ile His Tyr Ser Gly Ser Thr Lys Tyr Asn Pro Ser Leu Lys Ser
1               5                   10                  15

<210> SEQ ID NO 37
<211> LENGTH: 6
<212> TYPE: PRT
<213> ORGANISM: Artificial Sequence
<220> FEATURE:
<223> OTHER INFORMATION: CDR-H3

<400> SEQUENCE: 37

Asn Ser Leu Phe Ala Ser
1               5

<210> SEQ ID NO 38
<211> LENGTH: 15
<212> TYPE: PRT
<213> ORGANISM: Artificial Sequence
<220> FEATURE:
<223> OTHER INFORMATION: CDR-L1

<400> SEQUENCE: 38

Arg Ala Ser Glu Ser Val Asp Thr Tyr Gly Asp Ser Phe Met His
1               5                   10                  15

<210> SEQ ID NO 39
<211> LENGTH: 7
<212> TYPE: PRT
<213> ORGANISM: Artificial Sequence
<220> FEATURE:
<223> OTHER INFORMATION: CDR-L2

<400> SEQUENCE: 39

Arg Ala Ser Asn Leu Glu Ser
1               5

<210> SEQ ID NO 40
<211> LENGTH: 9
<212> TYPE: PRT
<213> ORGANISM: Artificial Sequence
<220> FEATURE:
<223> OTHER INFORMATION: CDR-L3

<400> SEQUENCE: 40

Gln Gln Ser Asn Glu Ala Pro Tyr Thr
1               5
```